US007677409B2

(12) United States Patent
Reynolds

(10) Patent No.: US 7,677,409 B2
(45) Date of Patent: Mar. 16, 2010

(54) TEST SENSOR CARTRIDGES AND SENSOR-DISPENSING INSTRUMENTS

(75) Inventor: Jeffery S. Reynolds, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 110 days.

(21) Appl. No.: 11/794,968

(22) PCT Filed: Jan. 13, 2006

(86) PCT No.: PCT/US2006/001617

§ 371 (c)(1),
(2), (4) Date: Jul. 10, 2007

(87) PCT Pub. No.: WO2006/076721

PCT Pub. Date: Jul. 20, 2006

(65) Prior Publication Data

US 2008/0094804 A1    Apr. 24, 2008

Related U.S. Application Data

(60) Provisional application No. 60/643,801, filed on Jan. 14, 2005, provisional application No. 60/684,129, filed on May 24, 2005.

(51) Int. Cl.
*H05K 7/14*    (2006.01)
(52) U.S. Cl. .................. 221/232; 221/208; 221/259
(58) Field of Classification Search ........... 221/1, 221/12, 13, 20, 29, 45, 50, 52, 55, 56, 58, 221/59, 62, 63, 74, 78, 79, 80, 87, 90, 91, 221/151, 152, 154, 175, 176, 177, 191, 192, 221/193, 195, 197, 198, 205, 208, 210, 212, 221/216, 226, 228, 229, 230, 232, 234, 235, 221/238, 246, 247, 248, 249, 250, 255, 268, 221/270, 271, 272, 273, 276, 279, 280, 282, 221/287, 289, 30, 303, 306, 309, 310
See application file for complete search history.

(56) References Cited

U.S. PATENT DOCUMENTS

| 1,445,563 | A | * | 2/1923 | Spencer | 221/248 |
| 2,551,425 | A | * | 5/1951 | Drexel | 221/155 |
| 3,831,986 | A | * | 8/1974 | Kobayashi | 292/201 |
| 4,164,301 | A | * | 8/1979 | Thayer | 220/253 |
| 4,911,344 | A | * | 3/1990 | Kahler | 221/135 |

(Continued)

FOREIGN PATENT DOCUMENTS

| EP | 1 321 769 A1 | 6/2003 |
| EP | 1 329 395 A1 | 7/2003 |
| EP | 1 352 611 A1 | 10/2003 |
| WO | WO 03/083469 A2 | 10/2003 |
| WO | WO 2004/063747 A1 | 7/2004 |

OTHER PUBLICATIONS

Written Opinion of the International Searching Authority corresponding to co-pending International Patent Application No. PCT/US2006/001617, European Patent Office, dated Aug. 21, 2006, 9 pages.
International Search Report corresponding to co-pending International Patent Application No. PCT/US2006/001617, European Patent Office, dated Aug. 21, 2006, 7 pages.

*Primary Examiner*—Gene Crawford
*Assistant Examiner*—Kelvin L Randall, Jr.
(74) *Attorney, Agent, or Firm*—Nixon Peabody LLP

(57) ABSTRACT

The cartridge comprises a housing, a plurality of test sensors, a mechanical mechanism, and a pusher assembly. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. One of the plurality of test sensors is positioned for extraction from the cartridge. The pusher assembly is adapted to push one of the plurality of test sensors from the cartridge. The pusher assembly includes a ferromagnetic material or a magnet.

16 Claims, 35 Drawing Sheets

U.S. PATENT DOCUMENTS

| | | |
|---|---|---|
| 5,510,266 A * | 4/1996 | Bonner et al. .................. 436/43 |
| 5,971,941 A | 10/1999 | Simons et al. .............. 600/573 |
| 6,135,314 A * | 10/2000 | Menes ......................... 221/232 |
| 6,220,435 B1 * | 4/2001 | Nobile et al. ................ 206/409 |
| 6,827,899 B2 | 12/2004 | Maisey et al. .................. 422/61 |
| 6,872,358 B2 * | 3/2005 | Hagen et al. .................. 422/61 |
| 6,908,008 B2 | 6/2005 | Pugh ........................... 221/135 |
| 6,997,343 B2 | 2/2006 | May et al. .................... 221/232 |
| 7,063,234 B2 | 6/2006 | Giraud ........................ 221/271 |
| 7,138,089 B2 | 11/2006 | Aitken et al. .............. 422/82.01 |
| 7,264,139 B2 * | 9/2007 | Brickwood et al. .......... 221/270 |
| 2003/0116583 A1 * | 6/2003 | Pugh ........................... 221/268 |
| 2003/0132276 A1 * | 7/2003 | Metzler et al. .......... 229/125.37 |
| 2003/0186446 A1 | 10/2003 | Pugh ............................ 436/46 |
| 2003/0191415 A1 | 10/2003 | Moerman et al. ........... 600/584 |
| 2003/0212345 A1 | 11/2003 | McAllister et al. .......... 600/584 |
| 2003/0223906 A1 | 12/2003 | McAllister et al. ............ 422/58 |
| 2008/0181818 A1 * | 7/2008 | Ruan ......................... 422/68.1 |

* cited by examiner

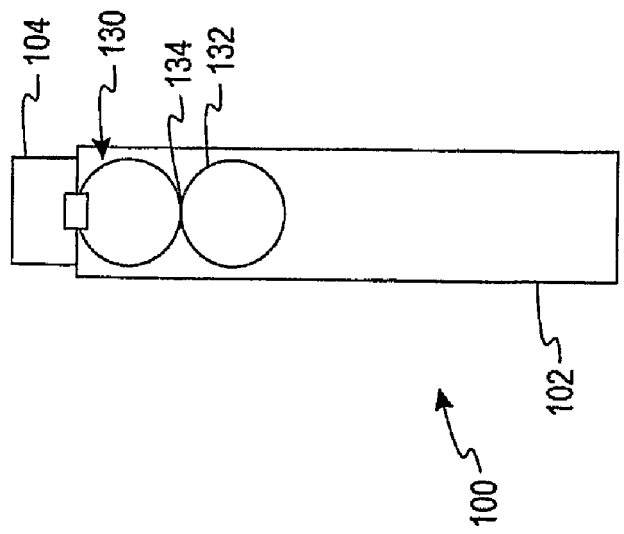
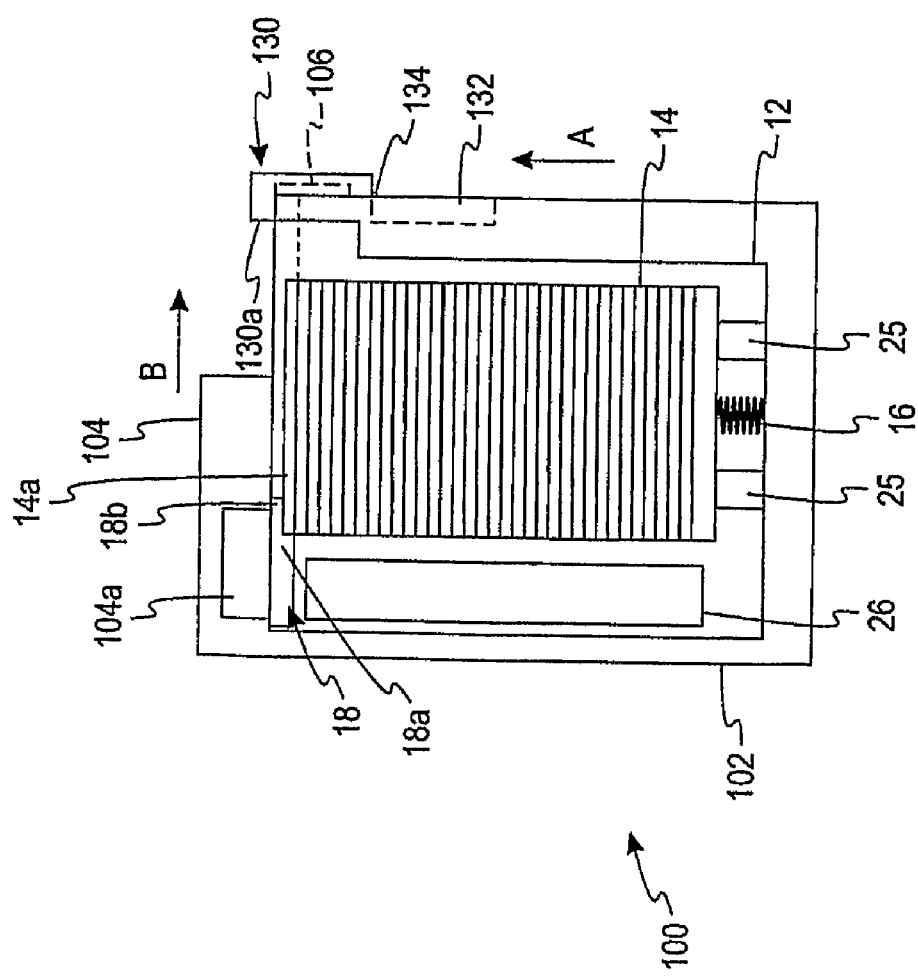

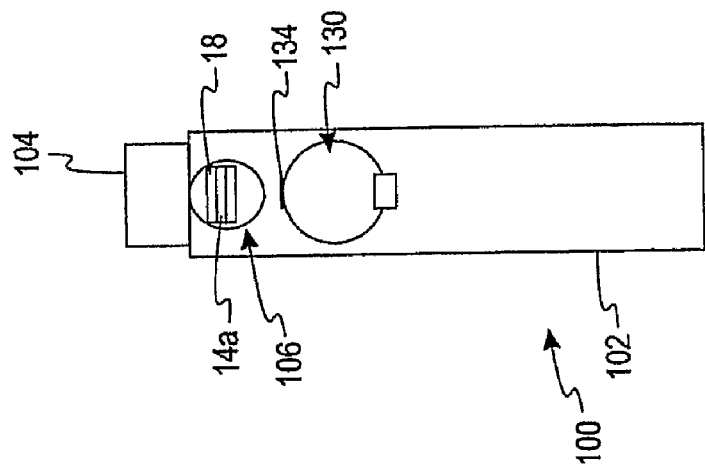
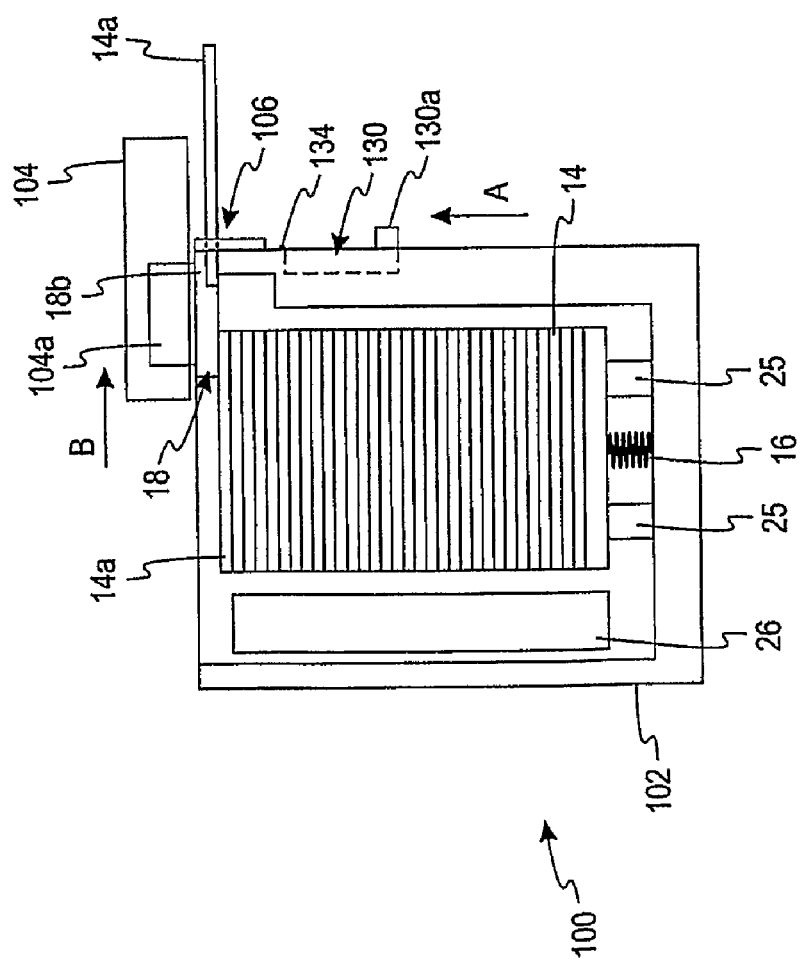

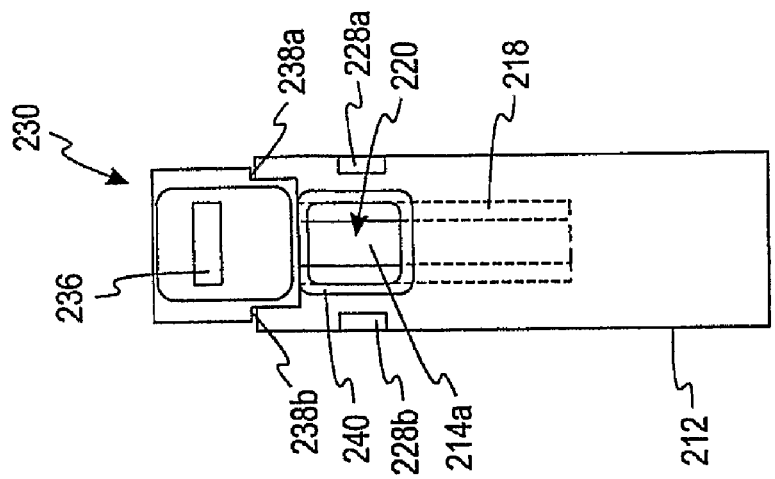
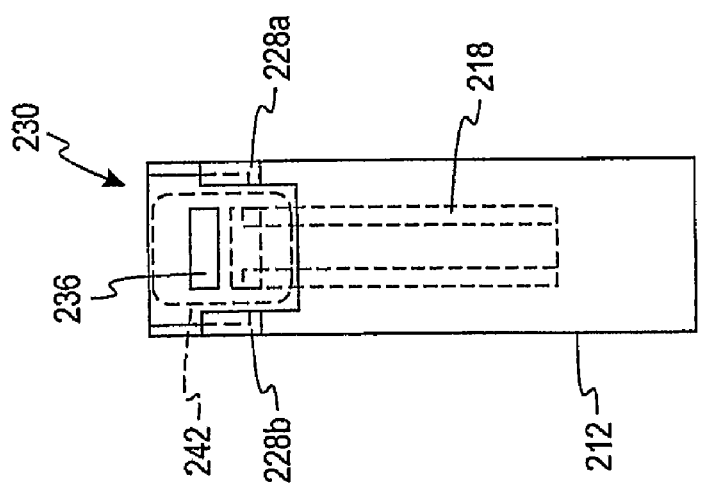

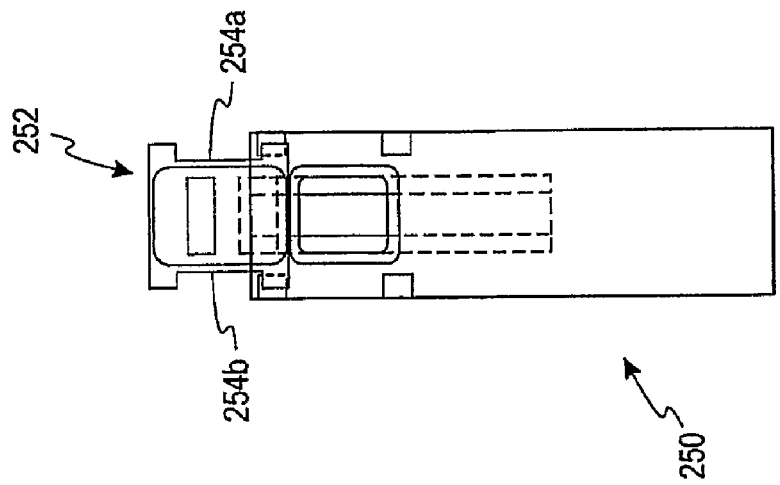
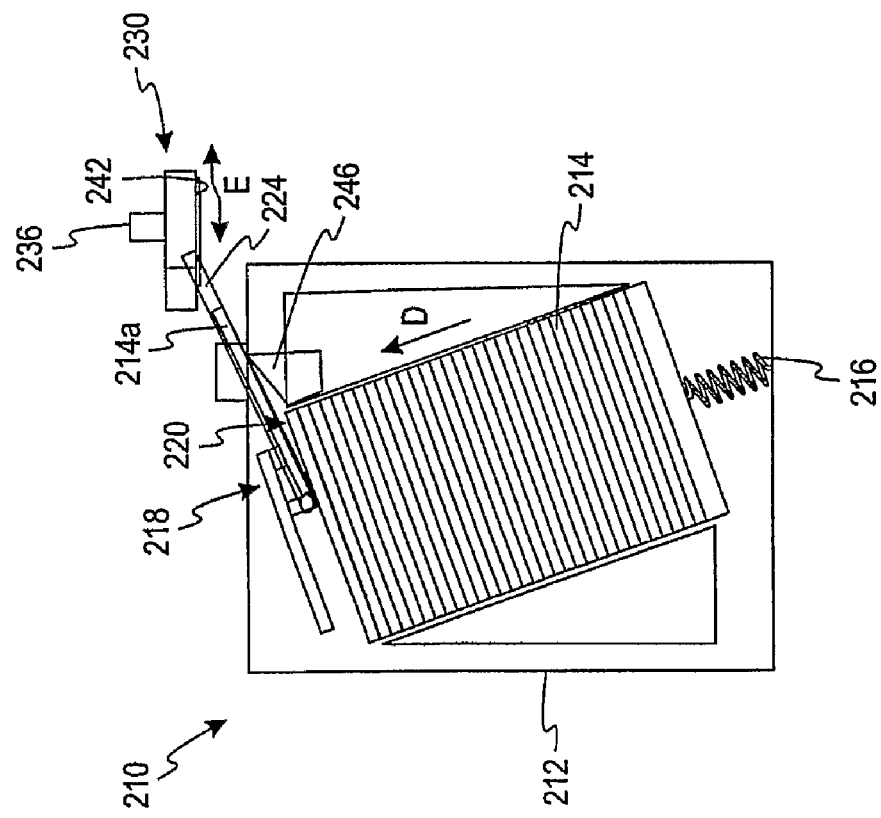
Fig. 5d
Fig. 5c

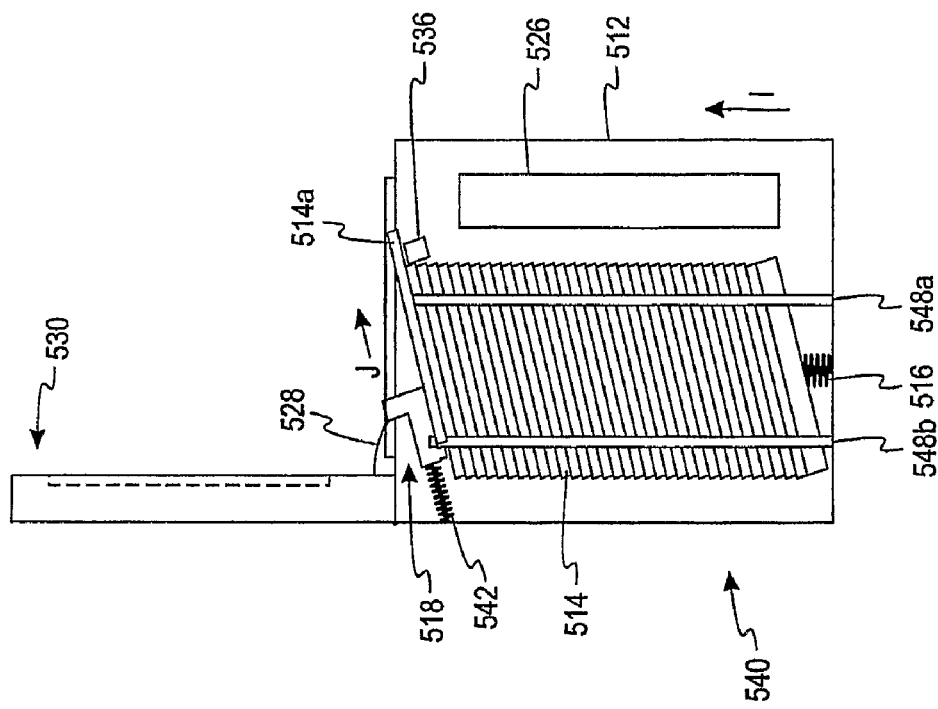
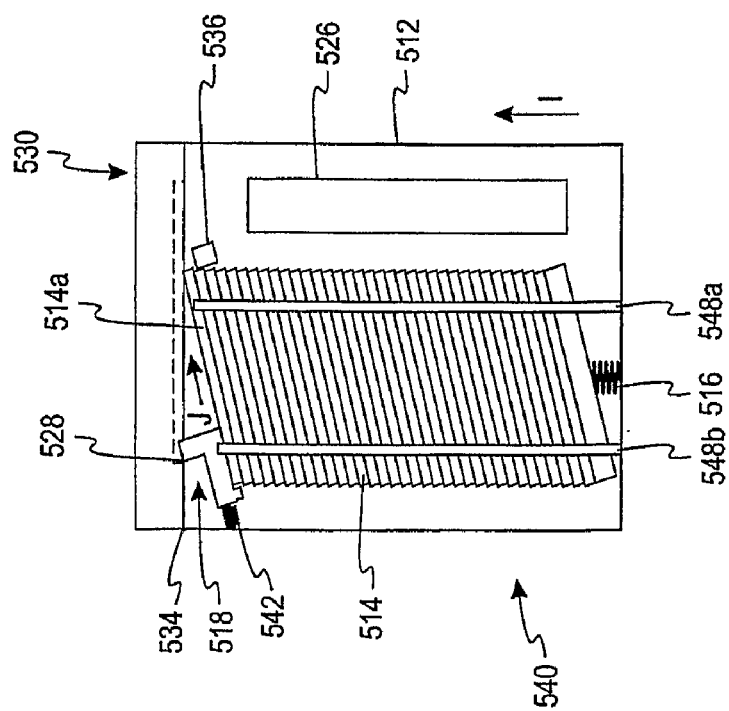
Fig. 9c
Fig. 9d

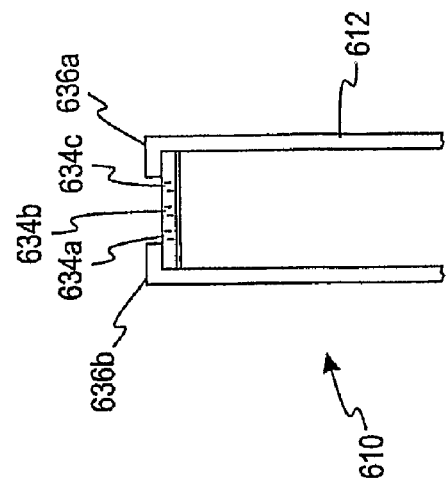
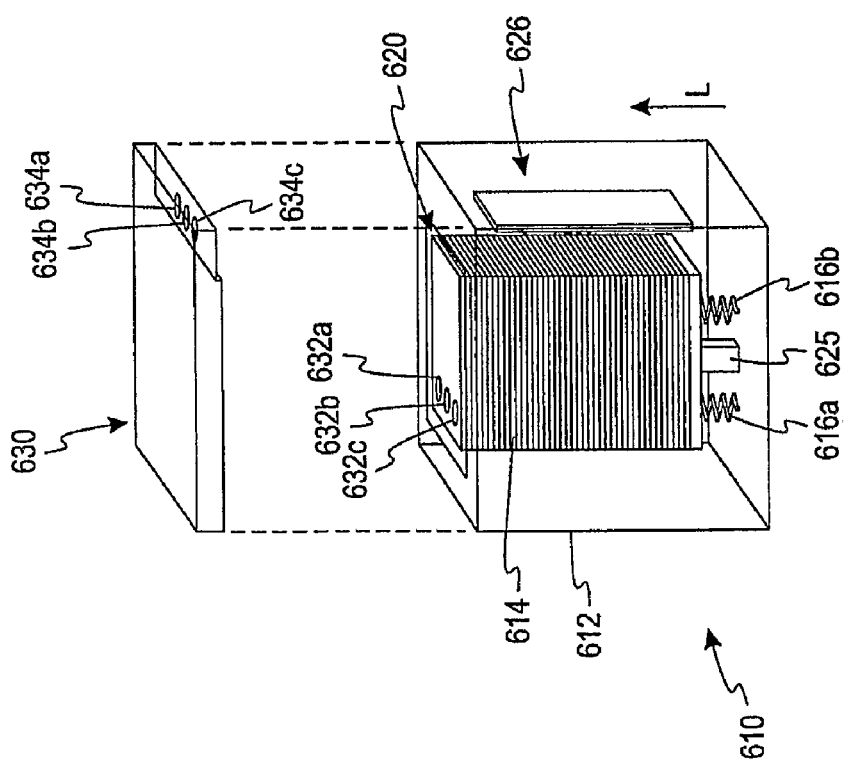
Fig. 11b
Fig. 11a

TEST SENSOR CARTRIDGES AND SENSOR-DISPENSING INSTRUMENTS

CROSS-REFERENCE TO RELATED APPLICATIONS

This application claims priority to Application No. 60/643,801 filed on Jan. 14, 2005 and Application No. 60/684,129 filed on May 24, 2005 both of which are incorporated by reference in their entirety.

FIELD OF THE INVENTION

The present invention generally relates to cartridges and sensor-dispensing instruments and, more particularly, to cartridges with a plurality of test sensors that is used in analyzing, for example, blood glucose or other analytes contained therein.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets. While the remainder of the disclosure herein will be directed towards determining glucose, it is to be understood that the present invention may be used for determining other analytes on selection of an appropriate enzyme.

The results of such tests can be used to determine what, if any, insulin or other medication needs to be administered. In one type of blood-glucose testing system, sensors are used to test a sample of blood.

A test sensor contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested is supplied to contact areas located near the rear or contact end of the sensor.

Such a test sensor is often sensitive to the effects of ambient humidity. One way to reduce or eliminate the effects of ambient humidity is to individually package each of the sensors with desiccant. Such a method has a drawback of requiring the unpacking of a strip before each use. Thus, it would be desirable to have a cartridge that contains a plurality of test sensors that would not require unpacking each strip before using. Also, for the convenience and ease of use, it would also be desirable to have a simple mechanism to feed the test sensors, one at a time, for testing by the user. This provides ease of use to normal users and is especially important for those users who may have some physical limitations. It would also be desirable to reliably seal the test sensors within the cartridge.

SUMMARY OF THE INVENTION

According to one embodiment, a cartridge is adapted to be used with a sensor-dispensing instrument. The cartridge comprises a housing, a plurality of test sensors, a mechanical mechanism, and a pusher assembly. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. One of the plurality of test sensors is positioned for extraction from the cartridge. The pusher assembly is adapted to push one of the plurality of test sensors from the cartridge. The pusher assembly includes a ferromagnetic material or a magnet.

According to one embodiment, a sensor-dispensing instrument comprises a cartridge, an instrument housing, a lid and a slider. The cartridge includes a cartridge housing, a plurality of test sensors, a mechanical mechanism, and a pusher assembly. The cartridge housing forms at least one cartridge opening therethrough. The plurality of test sensors is stacked in the cartridge housing. The plurality of test sensors is adapted to assist in testing at least one analyte. The mechanical mechanism is adapted to urge the plurality of test sensors in a first direction. One of the plurality of test sensors is positioned for extraction from the cartridge. The pusher assembly is adapted to push one of the plurality of test sensors from the cartridge. The pusher assembly includes a ferromagnetic material or a magnet. The instrument housing forms a dispensing outlet and is adapted to receive the cartridge. The lid is moveable between a closed position and an open position such that the lid seals at least one of the dispensing outlet and the cartridge opening in the closed position. The slider comprises a ferromagnetic material or a magnet. The slider is adapted to be magnetically coupled to the pusher assembly of the cartridge. The slider is adapted to slide from a first position to a second position. During the movement of the slider from the first position to the second position, the pusher assembly contacts one of the plurality of test sensors and pushes it at least partially through the dispensing opening. At least the pusher assembly or the slider comprises a magnet.

According to one embodiment, a lid mechanism is adapted to be used in a cartridge or a sensor-dispensing instrument that includes a plurality of test sensors to assist in determining the concentration of at least one analyte. The lid mechanism comprises a lid and a plurality of retainer tabs. The lid is adapted to slide between a closed position and an open position such that the lid seals an opening in the closed position. The plurality of retainer tabs to assist in maintaining pressure on the lid in forming a seal.

According to another embodiment, a cartridge comprises a housing, a plurality of test sensors, a mechanical mechanism, a test-sensor extractor and a lid. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. One of the plurality of test sensors is positioned for extraction from the cartridge. The test-sensor extractor is adapted to move between a first position and a second position. The lid is mechanically linked to the test-sensor extractor. The lid is moveable being a closed position and an open position such that the lid seals the opening in the closed position. During the movement of the lid from the closed position to the open position, the test-sensor extractor moves from the first position to the second position and extracts one of the plurality of test sensors at least partially through the opening.

According to another embodiment, a cartridge comprises a housing, a plurality of test sensors, a first mechanical mechanism, a second mechanical mechanism, a test-sensor extractor, and a lid. The housing forms at least one opening therethrough. The plurality of test sensors is stacked in the housing. The plurality of test sensors is adapted to assist in testing at least one analyte. The first mechanical mechanism is adapted to urge the plurality of test sensors in a first direction. One of the plurality of test sensors is positioned for extraction from the cartridge. The second mechanical mechanism is adapted to urge the plurality of test sensors in a second direction. The second direction is located generally perpendicular to the first direction. The test-sensor extractor is moveable between a first position and a second position via the second mechanical mechanism. The lid is moveable between a closed position and an open position such that the lid seals the opening in the closed position. During the movement of the lid from the closed position to the open position, the test-sensor extractor moves from the first position to the second position and extracts one of the plurality of test sensors at least partially through the opening.

According to a further embodiment, a cartridge comprises a housing, a plurality of test sensors, a first mechanical mechanism, a lid, and a pusher assembly. The housing forms at least one opening therethrough. The plurality of test sensors is stacked in the housing on a slant. The plurality of test sensors is adapted to assist in testing at least one analyte. The first mechanical mechanism is adapted to urge the plurality of test sensors in a first direction. One of the plurality of test sensors is positioned for extraction from the cartridge. The lid is moveable between a closed position and an open position such that the lid seals the opening in the closed position. The pusher assembly is connected to the lid. The pusher assembly is moveable between a first position and a second position. During the movement of the lid from the closed position to the open position, the pusher assembly moves from the first position to the second position and extracts one of the plurality of test sensors at least partially through the opening.

According to yet another embodiment, a cartridge comprises a housing, a plurality of test sensors, a mechanical mechanism, and a lid. The housing forms at least one opening therethrough. The plurality of test sensors is stacked in the housing on a slant. The plurality of test sensors is adapted to assist in testing at least one analyte. The mechanical mechanism is adapted to urge the plurality of test sensors in a first direction. One of the plurality of test sensors is positioned for extraction from the cartridge. The lid is moveable between a closed position and an open position. The lid seals the opening in the closed position. The lid in the open position allows the plurality of test sensors, one at a time, to be manually extracted from the cartridge.

According to yet another embodiment, a cartridge comprises a housing, a plurality of test sensors, a mechanical mechanism, and a lid. The housing forms at least one opening therethrough. The plurality of test sensors is stacked in the housing. The plurality of test sensors is adapted to assist in testing at least one analyte. The plurality of test sensors includes at least one sensor electrical contact. The mechanical mechanism is adapted to urge the plurality of test sensors in a first direction. One of the plurality of test sensors is positioned for extraction from the cartridge. The lid is moveable between a closed position and an open position such that the lid seals the opening in the closed position. The lid includes at least one lid electrical contact. During the movement of the lid from the closed position to the open position, the at least one electrical contact contacts the at least one sensor contact of one of the plurality of test sensors. During movement of the lid from the open position to the closed position, the lid extracts one of the plurality of test sensors at least partially through the opening.

According to yet a further embodiment, a cartridge comprises a housing, a plurality of test sensors, a mechanical mechanism, and a rotatable drum. The housing has an interior portion. The plurality of test sensors is stacked in the housing. The plurality of test sensors is adapted to assist in testing at least one analyte. The mechanical mechanism is adapted to urge the plurality of test sensors in a first direction. One of the plurality of test sensors is positioned for extraction from the cartridge. The rotatable drum includes at least one notch formed therein. The drum is coupled to an interior portion of the housing. The at least one notch is adapted to receive exactly one test sensor. During the movement of the drum from a first position to a second position, the plurality of test sensors, one at a time, is extracted from the interior of the cartridge.

According to another embodiment, a cartridge adapted to be used with a sensor-dispensing instrument comprises a housing, a plurality of test sensors, a mechanical mechanism, and a test-sensor extractor. The housing forms at least two openings therethrough. The plurality of test sensors is stacked in the housing. The plurality of test sensors is adapted to assist in testing at least one analyte. The mechanical mechanism is adapted to urge the plurality of test sensors in a first direction. The test-sensor extractor is adapted to carry and extract the plurality of test sensors, one at a time, in a second direction at least partially through one of the at least two openings. The test-sensor extractor has a first portion and a second portion. The first portion and the second portion are connected by at least one hinge. The second direction and the first direction are generally perpendicular to each other.

According to one embodiment, a sensor-dispensing instrument comprises a cartridge, an instrument housing, an ejector mechanism, and at least one deflector. The cartridge includes a cartridge housing, a plurality of test sensors, a mechanical mechanism, and a test-sensor extractor. The cartridge housing forms at least two openings therethrough. The plurality of test sensors is stacked in the housing. The plurality of test sensors is adapted to assist in testing at least one analyte. The mechanical mechanism is adapted to urge the plurality of test sensors in a first direction. The test-sensor extractor is adapted to carry and extract the plurality of test sensors, one at a time, in a second direction at least partially through one of the openings. The test-sensor extractor has a first portion and a second portion. The first portion and the second portion are connected by at least one hinge. The second direction and the first direction being generally perpendicular to each other. The instrument housing forms a dispensing outlet and is adapted to receive the cartridge. The ejector mechanism is adapted to extend through at least one of the openings and contact the test-sensor extractor. The at least one deflector is adapted to contact and deflect the first portion of the test-sensor extractor and assist in extracting the plurality of test sensors, one at a time, at least partially through the dispensing outlet.

According to yet another embodiment, a cartridge adapted to be used with a sensor-dispensing instrument comprises a housing, a base, a plurality of test sensors, and an exterior spring mechanism. The housing forms at least one opening therethrough. The base is adapted to be in sealing engagement with the housing in a first position. The plurality of test sensors is stacked in the housing. The plurality of test sensors is adapted to assist in testing at least one analyte. The exterior spring mechanism is attached to the housing and the base and adapted to assist in sealingly engaging the housing and the base. In a first position, the housing and the base are in sealing engagement and, in a second position, the housing and base are spaced apart.

According to a further embodiment, a sensor-dispensing instrument comprises a cartridge, an instrument housing, and an ejector mechanism. The cartridge includes a cartridge housing, a base, a plurality of test sensors, and an exterior spring mechanism. The cartridge housing forms at least one opening therethrough. The base is adapted to be in sealing engagement with the housing in a first position. The plurality of test sensors is stacked in the housing. The plurality of test sensors is adapted to assist in testing at least one analyte. The exterior spring mechanism is attached to the cartridge housing and the base and adapted to assist in sealingly engaging the cartridge housing and the base. The instrument housing forms a dispensing outlet and is adapted to received the cartridge. The ejector mechanism is adapted to move and be inserted between the cartridge housing and the base such that the cartridge housing and base are spaced apart. The ejector mechanism is adapted to carry and extract the plurality of test sensors, one at a time, in a second direction at least partially from the cartridge. The second direction is generally perpendicular to the first direction. In a first position, the cartridge housing and the base are in sealing engagement and, in a second position, the cartridge housing and base are spaced apart.

According to another embodiment, a cartridge comprises a housing, a plurality of test sensors, a mechanical mechanism and a sliding pusher lid assembly. The housing forms at least one opening therethrough. The plurality of test sensors is stacked in the housing. The plurality of test sensors is adapted to assist in testing at least one analyte. The mechanical mechanism is adapted to urge the plurality of test sensors in a first direction. One of the plurality of test sensors is positioned for extraction from the cartridge. The sliding pusher lid assembly includes a flexible pusher tab. The flexible pusher tab is adapted to contact and push one of the plurality of test sensors from the housing and at least partially through the opening. The flexible pusher tab extends generally outwardly and generally downwardly from the remainder of the sliding pusher lid assembly. In the closed position, the sliding pusher lid assembly is adapted to assist in sealing the cartridge.

According to another embodiment, a sensor-dispensing instrument is adapted to determine a concentration of an analyte and comprises a cartridge and instrument housing. The cartridge includes a cartridge housing, a plurality of test sensors, a mechanical mechanism, and a sliding pusher lid assembly. The cartridge housing forms at least one cartridge opening therethrough. The plurality of test sensors is stacked in the cartridge housing. The plurality of test sensors is adapted to assist in testing at least one analyte. The mechanical mechanism is adapted to urge the plurality of test sensors in a first direction. One of the plurality of test sensors is positioned for extraction from the cartridge. The sliding pusher lid assembly is moveable between a first position and a second position. The sliding pusher lid assembly is adapted to assist in sealing the sensor-dispensing instrument in the second position. The sliding pusher assembly includes a flexible pusher tab. The flexible pusher tab extends generally outwardly and generally downwardly from the remainder of the sliding pusher lid assembly. The instrument housing forms a dispensing outlet and is adapted to receive the cartridge. The flexible pusher tab is adapted to push one of the plurality of test sensors from the cartridge and at least partially through the dispensing outlet.

BRIEF DESCRIPTION OF THE DRAWINGS

FIG. 3a is a front view of the sensor-dispensing instrument of FIG. 2 with the cartridge of FIG. 1 in a closed position.

FIG. 3b is a side view of the sensor-dispensing instrument of FIG. 3a.

FIG. 3c is a front view of the sensor-dispensing instrument of FIG. 2 and the cartridge of FIG. 1 in an open position with a sensor extending therethrough;

FIG. 3d is a side view of the sensor-dispensing instrument of FIG. 3c.

FIG. 4c is a cross-sectional view taken generally along lines 4c-4c of FIG. 4a.

FIG. 5a is a side view of a cartridge in a closed position according to another embodiment.

FIG. 5b is a side view of the cartridge of FIG. 5a in an open position.

FIG. 5c is a front view of the cartridge of FIG. 5b.

FIG. 5d is a side view of a cartridge in a closed position according to yet another embodiment.

FIG. 9c is a front view of a cartridge in a closed position according to another embodiment.

FIG. 9d is a front view of the cartridge of FIG. 9c in an open position.

FIG. 12b is a side view of a cartridge of FIG. 12a.

FIG. 14b is a front perspective view of the cartridge of FIG. 14a in an open position and the ejector mechanism of FIG. 14a.

FIG. 16b is an enlarged top view of the partial cartridge of FIG. 16a.

DETAILED DESCRIPTION OF THE ILLUSTRATED EMBODIMENTS

The present invention is directed to cartridges that contain a plurality of test sensors and sensor-dispensing instruments that use cartridges. The plurality of test sensors is used to determine concentrations of analytes. Analytes that may be measured using the present invention include glucose, lipid profiles (e.g., cholesterol, triglycerides, LDL and HDL), microalbumin, hemoglobin $A_{1C}$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, other body fluids like ISF (interstitial fluid) and urine, and non-body fluids.

Figure 1:
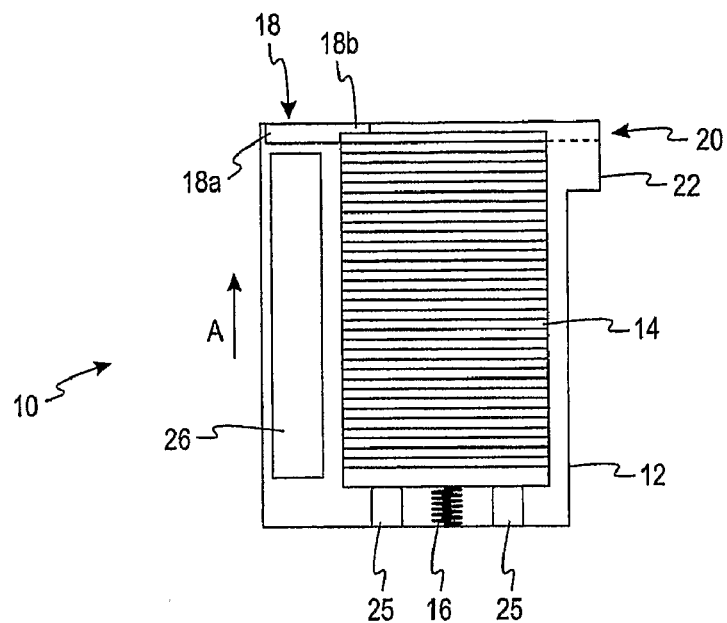
FIG. 1 is a front view of a cartridge according to one embodiment of the present invention.

Referring to the drawings, a cartridge 10 in FIG. 1 is shown that is adapted to be used in a sensor-dispensing instrument. The cartridge 10 of FIG. 1 comprises a housing 12, a plurality of test sensors 14, a mechanical mechanism 16, and a pusher assembly 18. The cartridge 10 is adapted to be disposable after all of the plurality of test sensors 14 have been used. If the cartridge 10 is used in a sensor-dispensing instrument, a spent cartridge may be replaced by a second identical cartridge that includes a plurality of unused test sensors.

Referring to FIG. 1, the housing 12 forms at least one opening 20 therethrough. The opening 20 is sized to allow the plurality of test sensors 14 to move therethrough one at a time and eventually exit the cartridge 10. Additionally, the pusher assembly 18 may be designed to operate such that at least a portion thereof partially extends through the opening 20. Specifically, the plurality of test sensors 14, one at a time, exits the cartridge 10 via the opening 20. It is desirable for the cartridge to include only one opening so as to reduce or eliminate additional exposure of the atmosphere on the plurality of test sensors 14.

The housing 12 may be made of a variety of materials, but is typically made of polymeric material. Some examples of polymeric materials that may be used in forming the housing 12 include polycarbonate, ABS, nylon, polystyrene, polypropylene, or combinations thereof. Other additives may be added in forming the housing such as, for example, TEFLON® for lubrication or glass to provide strength. It is contemplated that other additives may be employed. Polycarbonate is desirable for several reasons including being a durable material and having an ability to prevent or inhibit air (especially moisture) from entering the housing 12.

The housing 12 may be formed by processes known to those skilled in the art including injection-molding processes. It is contemplated that other processes may be used such as a molding process.

As shown in FIG. 1, the plurality of test sensors 14 is stacked in the housing 12. The plurality of test sensors contact a test sensor supports that assists in evenly feeding the test sensors, which is especially important for test sensors that are thinner and more flexible. The plurality of test sensors 14 is adapted to assist in testing at least one analyte. As discussed above, one of the analytes that may be tested is glucose from, for example, a whole blood sample. The test sensors 14 are typically electrochemical sensors or optical sensors. It is contemplated that other types of sensors that assist in testing at least one analyte may be used in the present invention.

In one embodiment, the plurality of test sensors includes an appropriately selected enzyme to react with the desired analyte or analytes to be tested. An enzyme that may be used to react with glucose is glucose oxidase. It is contemplated that other enzymes may be used such as glucose dehydrogenase.

An example of a test sensor 14 is disclosed in U.S. Pat. No. 6,531,040 assigned to Bayer Corporation. It is contemplated that other test sensors may be used in the cartridge 10.

The plurality of test sensors 14 may vary in number than shown in FIG. 1 so as to address the needs of different users and the physical storage requirements of the test sensors. Typically, the cartridge contains from about 10 to about 100 stacked test sensors and, more specifically, from about 25 to about 40 stacked test sensors. Because of limited shelf- and use-life of the test sensors, it is envisioned that a user who tests infrequently would likely desire a cartridge having less test sensors as opposed to a user who tests more frequently.

To urge the stacked test sensors 14 upwardly (in the direction of arrow A in FIG. 1), the mechanical mechanism 16 is used according to one embodiment. The mechanical mechanism 16 assists in positioning one of the plurality of test sensors for eventual ejection from the cartridge 10 via the opening 20. The mechanical mechanism is any device that can urge pressure on the stacked test sensors 14 so as to position one of the plurality of test sensors for ejection. For example, the mechanical mechanism 16 depicted in FIG. 1 is a spring. Various types of springs may be used as the mechanical mechanism to urge the stacked test sensors 14 in the direction of arrow A in FIG. 1. For example, the spring may be a compression spring or a torsion spring. Springs are desirable because of their simplicity and ease of use. It is contemplated that more than one spring may be used to urge the stacked test sensors in the direction of arrow A.

Additionally, the mechanical mechanism 16 may be a ratchet pusher. Using such an embodiment, the ratchet pusher automatically ratchets the stacked test sensors upwardly (i.e., the direction of arrow A in FIG. 1). The ratchet pusher would desirably need to extend the length of the interior of the cartridge such that all of test sensors would eventually be used. It is contemplated that the ratchet pusher may be used in combination with one or more springs.

To assist in guiding the mechanical mechanism 16 upwardly (in the direction of arrow A in FIG. 1), the housing 12 may be formed with a plurality of prongs or extensions 25. The optional prongs or extensions 25 assist in guiding the mechanical mechanism 16 in the direction of arrow A, thus making movement of the plurality of test sensors in this direction easier. Such prongs may be mated with a corresponding guide structure in the housing. For example, the prongs and guide structure may be in a tongue and groove relationship.

The cartridge 10 includes the pusher assembly 18 that is adapted to push one of the plurality of test sensors 14 from the cartridge. As shown in FIG. 1, the pusher assembly 18 is contained within the cartridge 10. The pusher assembly 18 includes a ferromagnetic material or a magnet. As will be discussed in detail below, the pusher assembly is adapted to be magnetically coupled with a slider of the sensor-dispensing instrument in pushing one of the plurality of test sensors 14 from the cartridge via the opening 20. At least one of the slider and the pusher assembly 18 comprises a magnet. For example, the slider and the pusher assembly 18 may comprise a magnet. It is contemplated that the slider may comprise a magnet and the pusher assembly 18 may comprise a ferromagnetic material. It is also contemplated that the slider may comprise a ferromagnetic material and the pusher assembly 18 comprises a magnet.

Examples of ferromagnetic material that may used in forming the pusher assembly 18 include, but are not limited to, iron, nickel, cobalt or combinations thereof. Ferromagnetic materials exhibit high magnetic permeability and increase strength of pull. One example of a magnet is an electromagnet.

To assist in sealing the cartridge against a dispensing outlet of the sensor-dispensing instrument (such as sensor-dispensing instrument 100 in FIG. 2), the cartridge 10 may include a sealing port 22. The sealing port 22 desirably surrounds the opening 20 of the cartridge 10. According to one embodiment, the sealing port 22 is a hollow seated tube that is made of polymeric material. The material forming the sealing port 22 is desirably made of a softer material than the surface of the sensor-dispensing instrument in which it contacts (e.g., inner surface 102a of housing 102 (FIG. 2)). For example, the inner surface 102a may be made of stainless steel. It is contemplated that the sealing port may be shaped differently and may be made of other materials.

It is contemplated that a seal may be on the sensor-dispensing instrument instead of the cartridge. In such an embodiment, the seal may be on an inner surface 102a of housing 102 (FIG. 2) in a sensor-dispensing instrument 100. The inner surface 102a contacts an exterior surface of the cartridge 10 when the cartridge is placed in the sensor-dispensing instrument 100.

The sensor-dispensing instrument 100 may include a detection mechanism that detects whether the lid is in a closed position. For example, the sensor-dispensing instrument 100 may include a detection mechanism such as a contact switch that alerts the user when the cap is not in the closed position. This alert may be provided to the user via an audible signal. This is especially desirable if the lid in the closed position provides the main source of protecting the test sensors from being exposed to humidity from the environment.

To assist in protecting the reagent(s) in the test sensors 14, desirable packaging material and/or desiccant material may be used. The cartridge 10 is typically packaged in material that prevents or inhibits air and moisture from entering into an interior of the housing 12 that contains the test sensors 14. One type of removable packaging that may be used to enclose the cartridge 10 is aluminum foil. It is contemplated that other types of removable packaging may be employed. It is contemplated that desiccant material may be added in the interior of the removable packaging to assist in maintaining an appropriate humidity level therein. If the reagent in the test sensors is not humidity sensitive, then there is little or no need to include much, if any, desiccant. The removable packaging with or without the desiccant material assists in increasing the shelf-use of the test sensors. The removable packaging is to be removed before the cartridge 10 is placed into the sensor-dispensing instrument.

It is contemplated that the cartridge 10 may be initially placed in a polymeric container such as a bottle or other type of container. The container may be shaped similarly to the cartridge with a desirable seal to prevent or inhibit air or moisture from entering the interior of the container. The container may include a lid that is attached to the remainder of the container via a living hinge. It is contemplated that desiccant may also be added within the container. The container with or without the desiccant material assists in increasing the shelf-use of the test sensors. The cartridge 10 is removed from the container before being placed into the sensor-dispensing instrument.

As shown in FIG. 1, desiccant material 26 is desirably added to the cartridge 10 to assist in maintaining an appropriate humidity level within the interior of the housing 12 that contains the plurality of test sensors 14. Specifically, some moisture may enter the interior of the housing 12 whenever a sensor is pushed out from the cartridge, but such moisture is desirably absorbed by the desiccant so as to protect the reagent in the test sensors from degradation. By maintaining an appropriate humidity level, reagent material in the test sensors is protected.

The amount of desiccant material 26 plus any extra desiccant included with any external packaging should be sufficient to obtain the desired shelf-life (the time period before any of the plurality of test sensors is used). More specifically, the shelf-life typically refers to the time period before the cartridge 10 is removed from the packaging material, if used. The amount of desiccant material 26 should also be sufficient to obtain the desired use-life (the time period after first use of one of the plurality of test sensors). More specifically, the use-life typically refers to the time period after the cartridge 10 is removed from the packaging material, if used.

Examples of desiccant that may be included within the disposable container, the removable packaging enclosing the disposable container, or the container containing the cartridge include commercially available desiccants. The desiccant may be in the form of several shapes including balls, tablets, granular, or paper. For example, the desiccant may be molecular sieve spheres or thick desiccant paper. The desiccant may be placed within the interior of the housing 12 such as shown with desiccant material 26. The desiccant may be molded into an interior surface of the housing 12 of the cartridge so as to absorb moisture within the same. One non-limiting example of desiccant material may be purchased from Multisorb of Buffalo, N.Y. in the form of, for example, molecular sieve beads.

It is contemplated that desiccant may not be used for test sensors that are not humidity sensitive. The amount of desiccant used, if any, depends on how humidity sensitive the test sensor is and the duration of the desired use-life and shelf-life.

Figure 2:
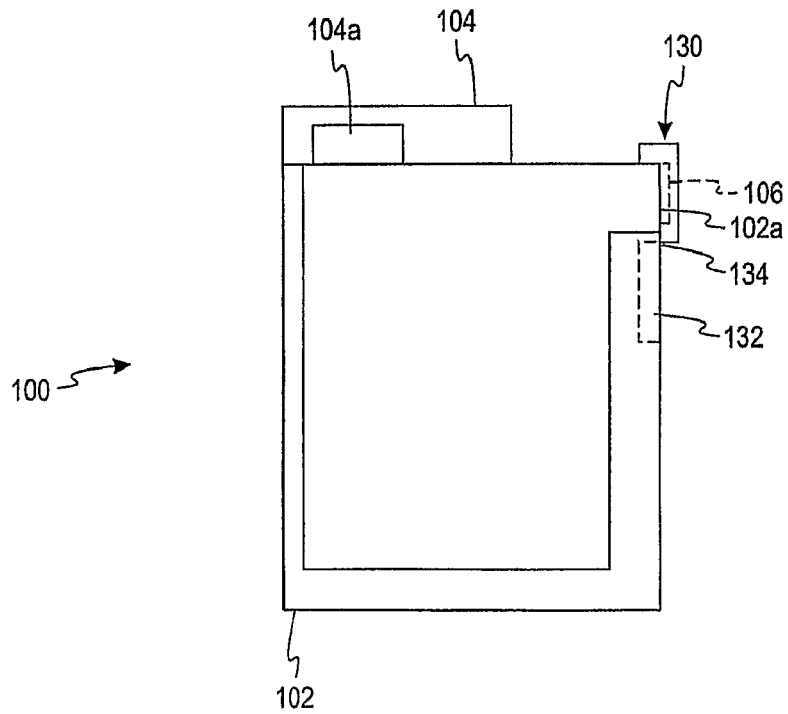
FIG. 2 is a front view of a sensor-dispensing instrument shown without the cartridge according to one embodiment.

Referring to FIGS. 2 and 3, a sensor-dispensing instrument 100 is depicted according to one embodiment. The sensor-dispensing instrument is used to determine concentrations of analytes. Analytes that may be measured using the present invention include glucose, lipid profiles (e.g., cholesterol, triglycerides, LDL and HDL), microalbumin, hemoglobin $A_1C$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, other body fluids like ISF (interstitial fluid) and urine, or non-body fluids.

The sensor-dispensing instrument 100 comprises a cartridge 10 (not shown in FIG. 2), an instrument housing 102, a slider 104 and a lid 130. As shown in FIGS. 3a, 3c, the instrument housing 102 is adapted to receive the cartridge 10 of FIG. 1. It is desirable for the cartridge 10 to be removed from and loaded into the instrument housing 102 of the sensor-dispensing instrument 100 in a simple and easy manner. The instrument housing 102 may be designed to load the cartridge via the bottom, the side or the top thereof.

It is contemplated that other cartridges may be used. Depending on the selected cartridge, the interior of the instrument housing may be redesigned to correspond to the selected cartridge. The instrument housing 102 also forms a dispensing outlet 106, which is sized to dispense the test sensors 14 one at a time.

The slider 104 comprises a ferromagnetic material or a magnet. As shown in FIGS. 2, 3a, 3b, the slider 104 includes a portion 104a that is a ferromagnetic material or a magnet. It is contemplated, however, that the slider may consist entirely of a ferromagnetic material or a magnet.

The slider 104 is adapted to be magnetically coupled to the pusher assembly 18 of the cartridge 10. As discussed above, at least one of the slider and the pusher assembly comprises a magnet. For example, the slider 104 and the pusher assembly 18 may comprise a magnet. It is contemplated that the slider 104 may comprise a magnet and the pusher assembly 18 may comprise a ferromagnetic material. It is also contemplated that the slider 104 may comprise a ferromagnetic material and the pusher assembly 18 comprises a magnet. Examples of ferromagnetic material that may used in forming the slider 104 include, but are not limited to, iron, nickel, cobalt or combinations thereof. Ferromagnetic materials exhibit high magnetic permeability and increase strength of pull.

Referring to FIG. 3a, the slider 104 is shown in a first position. By continuing to manually move the slider 104 in FIG. 3a, in the direction of arrow B, the slider 104 is moved to a second position (see FIG. 3c). The slider 104 in FIG. 3c is located closer to the dispensing outlet 106 than the slider 104 of FIG. 3a.

The pusher assembly 18 is adapted to move one of the plurality of test sensors 14 from the cartridge 10 and at least partially through the dispensing outlet 106, such as shown in FIGS. 3c, 3d with a test sensor 14a. When the slider 104 is in the first position (FIGS. 3a, 3b), the pusher assembly 18 (which is also in its first position in FIG. 3a) is positioned to allow the plurality of test sensors 14 to move in the direction of arrow A. The plurality of test sensors 14 is prevented from moving in the direction of arrow A after the test sensor 14a in FIG. 3a contacts a portion 18b of the pusher assembly 18. As the slider 104 is moved in the direction of arrow B (see FIG. 3c), the pusher assembly 18 is also moved in the direction of arrow B. As shown in FIGS. 3a, 3c, a portion 18b of the pusher assembly 18 contacts test sensor 14a and moves it at least partially through the dispensing outlet 106.

To assist in moving one of the plurality of test sensors 14 at least partially through the dispensing outlet 106, the lid 130 is moveable between a closed position (FIGS. 3a, 3b) and an open position (FIGS. 3c, 3d). In the closed position of FIGS. 3a, 3b, the lid 130 seals the dispensing outlet 106. In the open position of FIGS. 3c, 3d, the lid 130 is moved such that the test sensor 14a may exit through the dispensing outlet 106. When in the open position, the lid 130 is positioned in a recess 132 of FIGS. 3a, 3b with a portion 130a extending from the recess 132. The lid 130 is moved between the open position and the closed position via a hinge 134. It is contemplated that other mechanisms may be used to move the lid between the open and closed positions.

The lid 130 may be manually moved between the open position (FIGS. 3a, 3b) and the closed position (FIGS. 3c, 3d). The lid 130 may also be moved automatically between the open position (FIGS. 3a, 3b) and the closed position (FIGS. 3c, 3d). For example, the lid may have a link between the slider 104 and the lid 130 that moves the lid 130 automatically upon movement of the slider 104.

To provide an enhanced seal, it is desirable for the lid 130 to be a little more flexible than the circumference of the dispensing outlet 106. The lid 130 may be made of materials including polymeric materials. Some examples of polymeric materials that may be used in forming the housing 12 include polycarbonate, ABS, nylon, polyethylene, polystyrene, polypropylene, or combinations thereof.

The lid 130 of FIGS. 2 and 3 is shown as being generally circular. It is contemplated, however, that the lid may be shaped differently than depicted in FIGS. 2 and 3. The sensor-dispensing instrument may be formed with a lid other than the lid 130 depicted in FIGS. 2 and 3.

To assist in providing an improved seal, the sensor-dispensing instrument may include a sealing mechanism such as a seal ridge located generally around the periphery of the dispensing opening. Alternatively, or in addition to, the lid may have a corresponding seal ridge that is located to generally surround the periphery of the dispensing opening when the lid is in a closed position. The sealing that is located generally around the periphery of the dispensing outlet and/or on the lid may be a variety of different seals such as (a) a raised seal that seals to a flat surface, (b) a rib and groove arrangement or (c) two generally flat surfaces. It is contemplated that other sealing techniques may be employed to prevent or inhibit moisture from reaching the test sensors.

According to another embodiment, the cartridge may include a sealing mechanism such as seal ridge that is located generally around the periphery of the opening. Alternatively, or in addition to, the lid may have a corresponding seal ridge that is located to generally surround the periphery of the dispensing opening when the lid is in a closed position. The sealing that is located generally around the periphery of the opening and/or on the lid may be a variety of different seals such as (a) a raised seal that seals to a flat surface, (b) a rib and groove arrangement or (c) two generally flat surfaces. It is contemplated that other sealing techniques may be employed to prevent or inhibit moisture from reaching the test sensors in the cartridge.

In the embodiment of FIGS. 1-3, the lid is shown as being part of the sensor-dispensing instrument. In alternative embodiments, the sealing lid may be a part of the cartridge in which the seal is formed against the cartridge inside of the sensor-dispensing instrument. Having the lid on the cartridge would eliminate the necessity of sealing the cartridge against the instrument such as shown in FIGS. 1 and 2 with sealing port 22 and inner surface 102a of the housing 102.

Figure 4A:
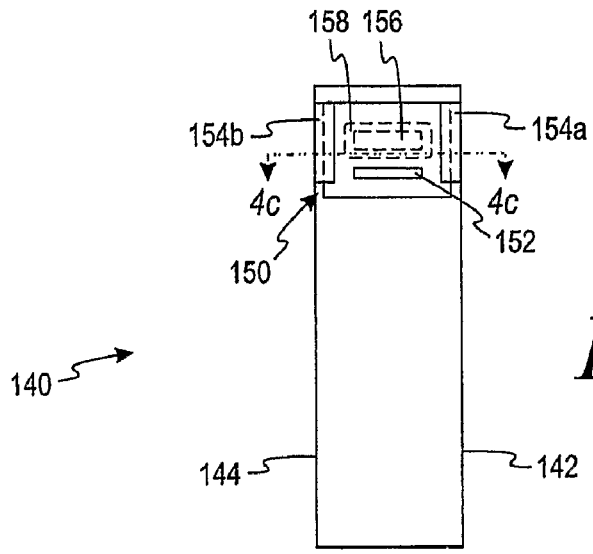
FIG. 4a is a side view of a cartridge or sensor-dispensing instrument according to another embodiment with the lid in a closed position.
Figure 4B:
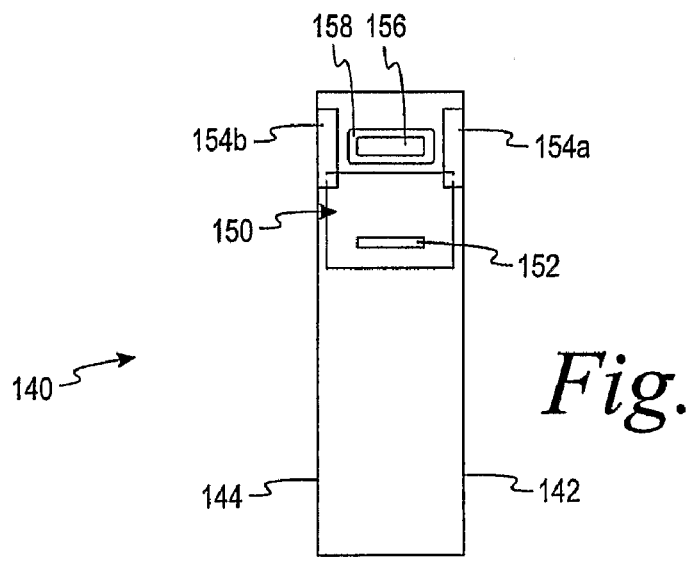
FIG. 4b is a side view of the cartridge or the sensor-dispensing instrument of FIG. 4a with the lid in an open position.

FIGS. 4a, 4b depict a sensor-dispensing instrument or a cartridge 140 that comprises opposing sidewalls 142, 144 and a lid 150. Specifically, the lid 150 may be used with a sensor-dispensing instrument or a cartridge. The lid 150 is adapted to slide between a closed position (FIG. 4a) and an open position (FIG. 4b).

To assist in manually sliding the lid 150 between the open position and the closed position, the lid 150 includes a handle or thumb grip 152. The handle 152 is a generally rectangular shape in FIGS. 4a, 4b. The handle, however, may be shaped differently than depicted in FIGS. 4a, 4b.

It is also contemplated that the lid 150 may be adapted to automatically move between the open position and the closed position. For example, a user may initiate the movement of the lid 150 via pressing a button. Alternatively, the lid may be linked to a pusher assembly or test-sensor extractor such that movement of the pusher assembly or test-sensor extractor moves the lid. For example, a cam mechanism may link the lid to the pusher assembly or the test-sensor extractor. For example, as the slider 104 is moved from the first position (FIG. 3a) to the second position (FIG. 3c), the lid is moved from an open position to the closed position. The same mechanism may also close the lid as the slider 104 is moved from the second position to the first position. To assist in closing the lid, a spring mechanism may be used.

Figure 4C:
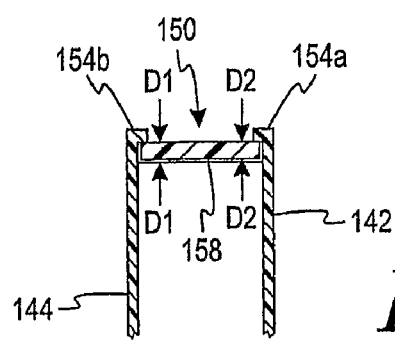

To assist in sliding the lid 150 between the open position and the closed position, the sensor-dispensing instrument or cartridge 140 further includes at least one retainer tab. For example, in FIGS. 4a-c, retainer tabs 154a,b restrict a lid 150 to sliding between the closed position (FIG. 4a) and the open position (FIG. 4a). To maintain positive pressure, the retainer tabs 154a, b may be made of a flexible material. To enhance the sealing of the lid, the thickness of the lid (D1 in FIG. 4c) may be slightly greater than the distance D2 when the retainer tabs 154a, b are in a resting position (i.e., when the lid is not exerting any pressure on the retainer tabs). In such an embodiment, the lid and retainer tabs form an interference fit. The retainer tabs may be injected molded in forming the cartridge or the sensor-dispensing instrument.

In the closed position (FIG. 4a), the lid 150 covers dispensing outlet 156, while in the open position (FIG. 4b), the lid 150 does not cover the dispensing outlet 156. The lid 150 may be made of similar materials as the lid 130.

The lid 150 of FIGS. 4a, 4b is shown as being a generally rectangular shape. It is contemplated, however, that the lid may be shaped differently than depicted in FIGS. 4a, 4b.

To assist in providing an improved seal, the sensor-dispensing instrument or cartridge 140 of FIGS. 4a, 4b may include a seal 158 located generally around the periphery of the dispensing opening 156 that works with the lid 150. The lid is designed to have a balance between the ease of sliding the lid between the open and closed positions, while still maintaining sufficient downwardly pressure to form a quality seal. Having a low coefficient of friction improves the ease of the lid being moved between the open and closed positions. It is contemplated that other sealing techniques may be used to provide a seal between the lid and the dispensing opening such as, for example, O-rings or compressible gaskets.

Figure 4D:
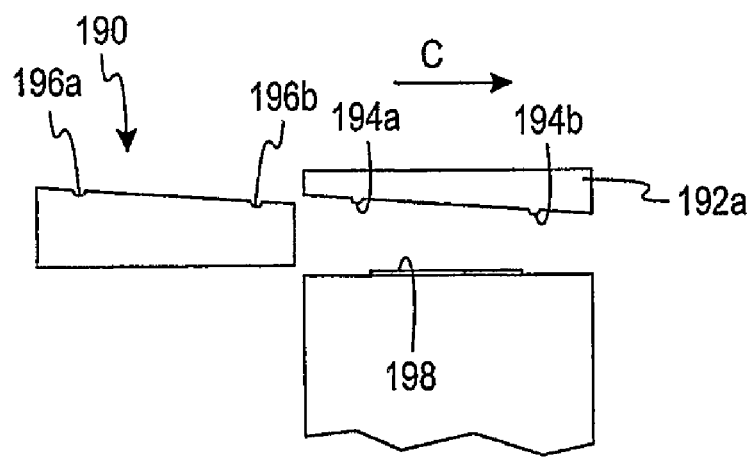
FIG. 4d is a side view of a lid and retainer tabs in an open position according to a further embodiment.
Figure 4E:
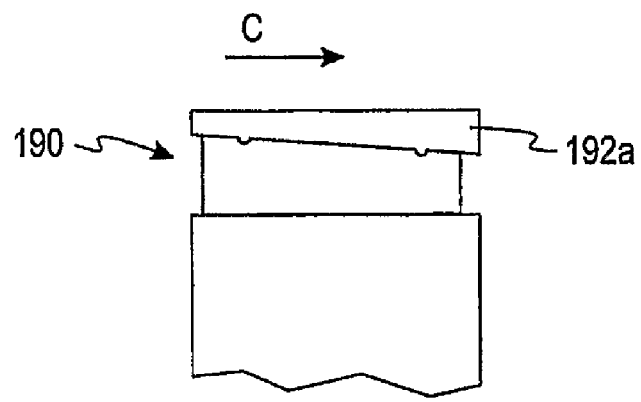
FIG. 4e is a side view of the lid and retainer tabs of FIG. 4d in a closed position.

According to a further embodiment, at least one of the retainer tabs may be angled. Referring to FIGS. 4d, 4e, a lid 190 is used in conjunction with an angled retainer tab 192a. As shown in FIGS. 4d, 4e, the retainer tab 192a forms at least one detent (detents 194a, 194b) to assist in indicating complete closure to the user. The detents 194a, 194b corresponds with respective recesses 196a, 196b formed in the lid 190. It is not necessary, however, that the lid 190 needs to work with at least one retainer tab having a detent as depicted in FIGS. 4d, 4e. The sensor-dispensing instrument or cartridge may also include a seal 198 that works in conjunction with the lid 190 to assist in preventing or inhibiting moisture from reaching the plurality of test sensors. It is contemplated that additional seals may be employed, including a seal located on the lid 190.

According to another embodiment, a cartridge 210 of FIGS. 5a-c, comprises a housing 212, a plurality of test sensors 214, a mechanical mechanism 216, a test-sensor extractor 218 and a lid 230. The cartridge 210 is adapted to be disposable after all of the plurality of test sensors 214 have been used.

Referring to FIGS. 5b, 5c, the housing 212 forms at least one opening 220 therethrough. The opening 220 is sized to allow the plurality of test sensors 214 to move therethrough, one at a time, and eventually exit the cartridge 210. Specifically, the plurality of test sensors 214, one at a time, exits the cartridge 210 via the opening 220. The housing 212 may be formed of the same materials and processes as described above in connection with housing 12.

As shown in FIG. 5c, the plurality of test sensors 214 is stacked in the housing 212. The plurality of test sensors 214 is adapted to assist in testing at least one analyte. As discussed above, one of the analytes that may be tested is glucose from, for example, a whole blood sample. The test sensors 214 may be the same as described above in connection with the plurality of test sensors 14.

To urge the stacked test sensors 214 generally upwardly (in the direction of arrow D in FIG. 5c), the mechanical mechanism 216 is used according to one embodiment. The mechanical mechanism 216 assists in positioning one of the plurality of test sensors 214 for eventual ejection from the cartridge 210 via the opening 220. The mechanical mechanism 216 may be a spring or the other devices described above in connection with mechanical mechanism 16.

The cartridge 210 also includes the test-sensor extractor 218 that is adapted to move between a first position (FIG. 5a) and a second position (FIG. 5b). The lid 230 is linked to the test-sensor extractor 218 by, for example, a mechanical linkage. For example, in FIG. 5c, the lid 230 is linked to the test-sensor extractor 218 via linkage 224. It is contemplated that the lid may be attached to the test-sensor extractor via other mechanisms such as a cam mechanism.

The movement of the lid 230 from the closed position (FIG. 5a) to the open position (FIG. 5b) results in the test-sensor extractor 218 moving from the first position to the second position and the extraction of test sensor 214a at least partially through the opening 220. FIG. 5c depicts the lid 230 in an open position in which the test sensor 214a has been moved partially through the opening 220. When the lid 230 is in the closed position (FIG. 5a), the lid seals the opening 220. According to one process, the lid 230 is manually moved between the open position and the closed position. To assist in manually moving the lid 230, the lid 230 may include a handle or push tab 236 that enables a user to more easily grasp and move the lid 230 in the direction of arrow E as shown in FIG. 5c. The path of arrow E is generally horizontal, but the lid 230 is lifted slightly vertical as shown in FIG. 5c to enable the test sensor 214a to be removed through the opening 220. It is contemplated that the lid 230 may be moved in an automatic process.

To assist in the extraction of one of the plurality of test sensors 214 at least partially through the opening 220, the cartridge 210 includes a ramp 246 (see FIG. 5c). The ramp 246 assists in directing the test sensors 214, one at a time, at least partially through the opening 220. The test sensor 214 may then be extracted fully by the user in a manual fashion. After the test sensor 214a has been extracted, the lid 230 is moved back to the closed position (FIG. 5a) and the test-sensor extractor is moved back to the first position (FIG. 5a) so as to be prepared to extract the next one of the plurality of test sensors 214.

The lid 230 works in connection with at least one retainer tab (retainer tabs 228a, 228b) in a similar manner as described above in connection with retainer tabs 154a, 154b. It is contemplated that other lids may be used with the test-sensor extractor 218 to extract the plurality of test sensors, one at a time, at least partially through the opening.

To assist in providing clearance for the linkage 224 shown in FIG. 5c, the lid may form at least one notch. For example, as shown in FIG. 5b, the lid 230 forms a plurality of notches 238a,238b. It is contemplated that the plurality of notches may be formed at different locations of the lid. For example, according to another embodiment, a cartridge 250 of FIG. 5d includes a lid 252. The lid 252 forms a plurality of notches 254a, b. The lid 252 with the plurality of notches 254a, b are in a general "I" shape. The cartridge 250 of FIG. 5d functions in a similar manner as the cartridge 210 of FIG. 5a.

Referring back to FIGS. 5a-c, the cartridge 210 may also include a sealing mechanism such as a seal ridge 240 located generally around the periphery of the opening 220. Similar to the seal ridge 158 discussed above, the seal ridge 240 assists in maintaining a desirable seal with the lid 230. The lid 230 of FIGS. 5a, 5b also includes a corresponding seal ridge 242 that may be formed instead of, or in addition to, the seal ridge 240. The seal ridge 242 assists in formed a seal generally around the periphery of the opening 220 when the lid 230 is in a closed position.

To assist in protecting the reagent(s) in the test sensors 214, desirable packaging material and/or desiccant material may be used. The cartridge 210 is typically packaged in material that prevents or inhibits air from entering into an interior of the housing 212 that contains the test sensors 214 as discussed above in connection with cartridge 10. Additionally, as discussed above in connection with cartridge 10, desiccant material may be added to the cartridge 210.

Figure 5E:
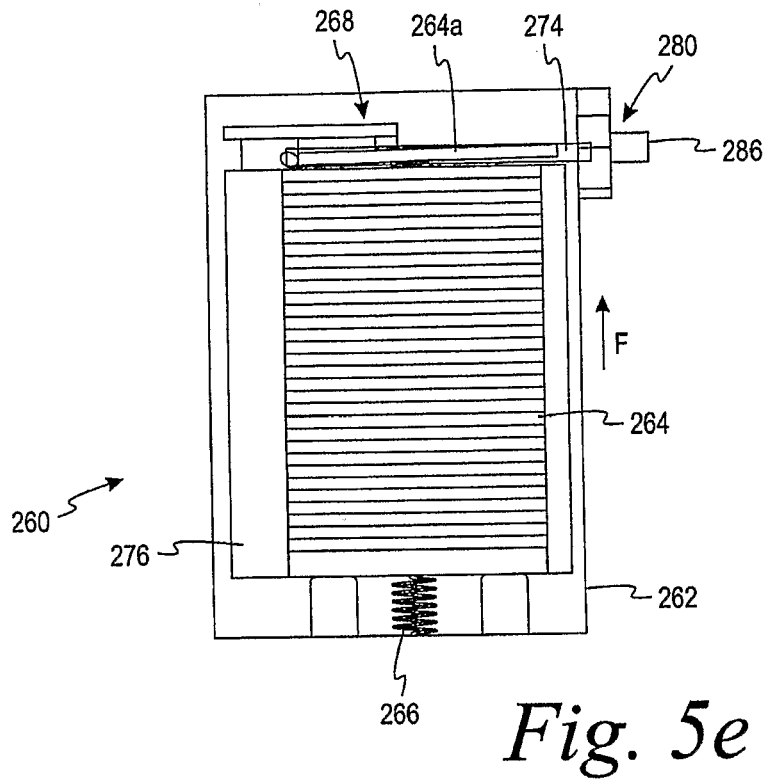
FIG. 5e is a front view of a cartridge in a closed position according to another embodiment.
Figure 5F:
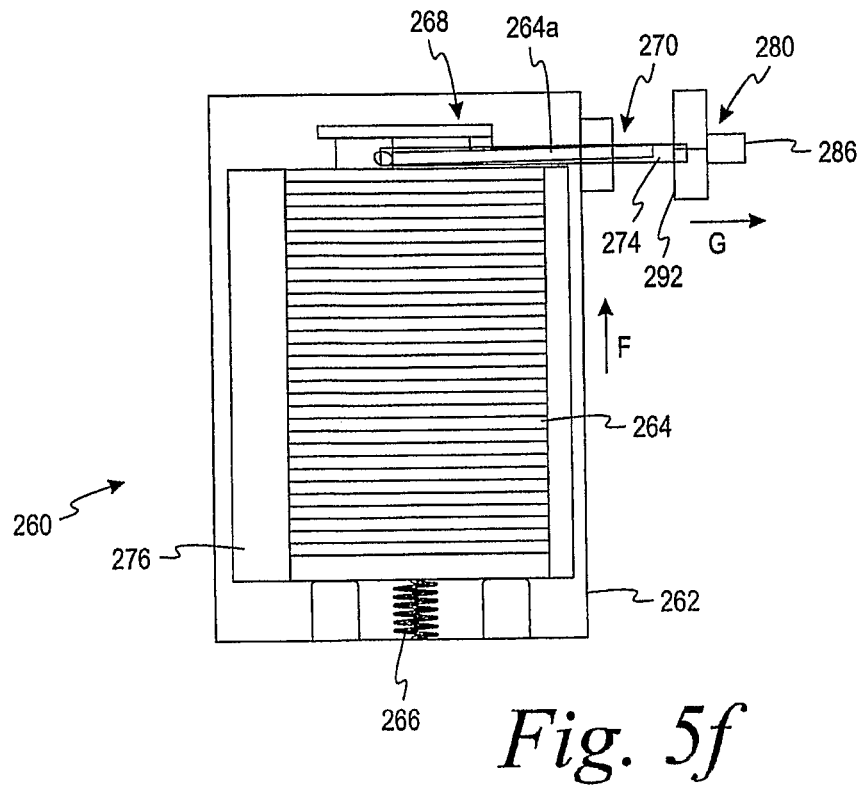
FIG. 5f is a front view of the cartridge of FIG. 5e in an open position.

According to another embodiment, a cartridge 260 of FIGS. 5e, 5f, comprises a housing 262, a plurality of test sensors 264, a mechanical mechanism 266, a test-sensor extractor 268 and a lid 280. The cartridge 260 is adapted to be disposable after all of the plurality of test sensors 264 have been used.

Referring to FIGS. 5e, 5f, the housing 262 forms at least one opening 270 therethrough. The opening 270 is sized to allow the plurality of test sensors 264 to move therethrough, one at a time, and eventually exit the cartridge 260. Specifically, the plurality of test sensors 264, one at a time, exits the cartridge 260 via the opening 270. The housing 262 may be formed of the same materials and processes as described above in connection with housing 12.

As shown in FIGS. 5e,f, the plurality of test sensors 264 is stacked in the housing 262. The plurality of test sensors 264 is adapted to assist in testing at least one analyte. As discussed above, one of the analytes that may be tested is glucose from, for example, a whole blood sample. The test sensors 264 may be the same as described above in connection with the plurality of test sensors 14.

To urge the stacked test sensors 264 generally upwardly (in the direction of arrow F in FIGS. 5e,f), the mechanical mechanism 266 is used according to one embodiment. The mechanical mechanism 266 assists in positioning one of the plurality of test sensors 264 for eventual ejection from the cartridge 260 via the opening 270. The mechanical mechanism 266 may be a spring or the other devices described above in connection with mechanical mechanism 16.

The cartridge 260 also includes the test-sensor extractor 268 that is adapted to move between a first position (FIG. 5e) and a second position (FIG. 5f). The lid 280 is linked to the test-sensor extractor 268 by, for example, a mechanical linkage. For example, the lid 280 is linked to the test-sensor extractor 268 via linkage 274. It is contemplated that the lid may be may be attached to the test-sensor extractor via other mechanisms such as a cam mechanism.

The movement of the lid 280 from the closed position (FIG. 5e) to the open position (FIG. 5f) results in the test-sensor extractor 268 moving from the first position to the second position and the extraction of test sensor 264a at least partially through the opening 270. FIG. 5f depicts the lid 280 in an open position in which the test sensor 264a has been moved partially through the opening 270. When the lid 280 is in the closed position (FIG. 5e), the lid seals the opening 270. According to one process, the lid 280 is manually moved between the open position and the closed position. To assist in manually moving the lid 280, the lid 280 may include a handle or push tab 286 that enables a user to more easily grasp and move the lid 280 in the direction of arrow G as shown in FIG. 5f. The path of arrow G is generally horizontal and is generally perpendicular to the direction of arrow F in FIGS. 5e, f. It is contemplated that the lid 280 may be moved in an automatic process.

The test sensor 264 may be extracted fully by the user in a manual fashion. After the test sensor 264a has been extracted, the lid 280 is moved back to the closed position (FIG. 5e) and the test-sensor extractor is moved back to the first position (FIG. 5f) so as to be prepared to extract the next one of the plurality of test sensors 264.

The lid 280 of FIGS. 5*e,f* also includes a seal 292 that assists in forming a seal generally around the periphery of the opening 270 when the lid 280 is in a closed position. It is contemplated that a seal may be located generally around the periphery of the opening 270. Such a seal may be formed in addition to, or instead of the seal 292.

To assist in protecting the reagent(s) in the test sensors 264, desirable packaging material and/or desiccant material may be used. The cartridge 260 is typically packaged in material that prevents or inhibits air from entering into an interior of the housing 262 that contains the test sensors 264 as discussed above in connection with cartridge 10. Additionally, as discussed above in connection with cartridge 10, desiccant material 276 may be added to the cartridge 260.

Figure 6C:
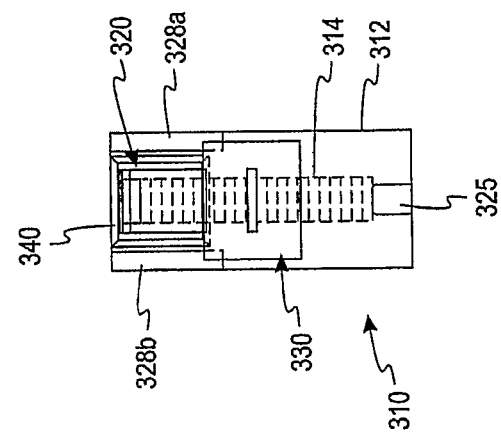
FIG. 6c is a side view of the cartridge of FIG. 6b.
Figure 6B:
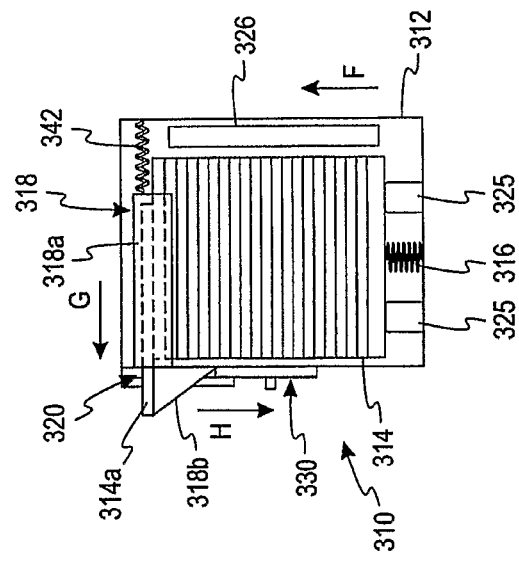
FIG. 6b is a front view of the cartridge of FIG. 6a in an open position.
Figure 6A:
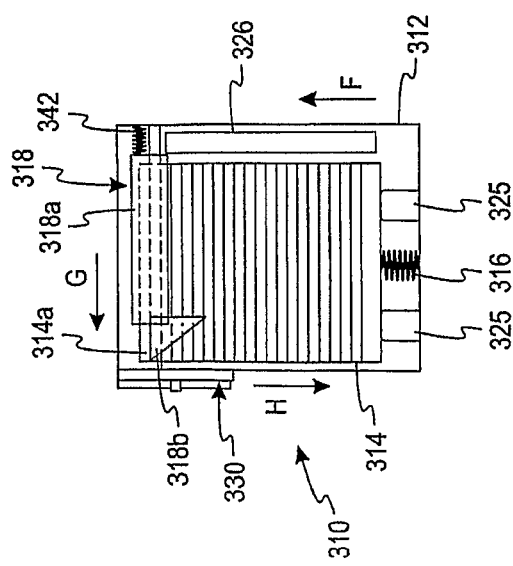
FIG. 6a is a front view of a cartridge in a closed position according to a further embodiment.

According to a further embodiment, a cartridge 310 of FIGS. 6*a-c*, comprises a housing 312, a plurality of test sensors 314, a first mechanical mechanism 316, a second mechanical mechanism 342, a test-sensor extractor 318 and a lid 330. The cartridge 310 is adapted to be disposable after all of the plurality of test sensors 314 have been used.

Referring to FIG. 6*b*, the housing 312 forms at least one opening 320 therethrough. The opening 320 is sized to allow the plurality of test sensors 314 to move therethrough, one at a time, and eventually exit the cartridge 310. Specifically, the plurality of test sensors 314, one at a time, exits the cartridge 310 via the opening 320. The housing 312 may be formed of the same materials and processes as described above in connection with housing 12.

As shown in FIGS. 6*a*, 6*b*, the plurality of test sensors 314 is stacked in the housing 312. The plurality of test sensors 314 is adapted to assist in testing at least one analyte as discussed above with respect to test sensors 14. To urge the stacked test sensors 314 in a first direction (in the direction of arrow F in FIGS. 6*a*, 6*b*), the first mechanical mechanism 316 is used according to one embodiment. The first mechanical mechanism 316 assists in positioning one of the plurality of test sensors 314 for eventual ejection from the cartridge 310 via the opening 320. The first mechanical mechanism 316 may be a spring or the other devices described above in connection with mechanical mechanism 16. To assist in guiding the mechanical mechanism 316 upwardly (in the direction of arrow F in FIGS. 6*a*, 6*b*), the housing 312 may be formed with a plurality of prongs or extensions 325.

The cartridge 310 also includes the test-sensor extractor 318 that is adapted to move between a first position (FIG. 6*a*) and a second position (FIG. 6*b*). The movement of the test-sensor extractor 318 is controlled by the lid 330 and the second mechanical mechanism 342. The second mechanical mechanism 342 is adapted to urge the plurality of test sensors 314 in a second direction (in the direction of arrow G in FIGS. 6*a*, 6*b*). The second direction (direction of arrow G) is generally perpendicular to the first direction (direction of arrow F). The second mechanical mechanism 342 may be a spring or other devices described above in connection with mechanical mechanism 16.

The lid 330 moves generally downwardly (in the direction of arrow H) from the closed position (FIG. 6*a*) to the open position (FIG. 6*b*). This movement of the lid 330 allows the test-sensor extractor 318 to move from a first position to the second position, which extracts one of the plurality of test sensors 314 at least partially through the opening 320. Specifically, when the lid 330 is moved to the open position, the second mechanical mechanism 342 urges pressure on the test-sensor extractor 318 in the direction of the opening 320 (in the direction of arrow G). The test-sensor extractor 318, in turn, contacts a test sensor 314*a* and moves this test sensor in the direction of the opening 320. Thus, the test-sensor extractor 318 is moved from a first position (FIG. 6*a*) to a second position (FIG. 6*b*) via the second mechanical mechanism 342. According to one process, the lid 330 is manually moved between the open position and the closed position. According to another process, the lid 330 may be automatically moved between the open position and the closed position by, for example, pressing a button. One example of an automatic process could include the plurality of test sensors being removed entirely using a motorized mechanism.

According to one embodiment, the test-sensor extractor 318 has a generally horizontal portion 318*a* and an angular or sloped portion 318*b*. The angular portion 318*b* extends from the cartridge 310 when the lid 330 is in the open position.

When the lid 330 is moved back to the closed position, the lid 330 releasably engages the angular portion 318*b* of the test-sensor extractor 318 and pushes the angular portion 318*b* back into the cartridge 310. After the test sensor 314*a* has been extracted, the lid 330 is moved back to the closed position (FIG. 6*a*) and the test-sensor extractor 318 is moved back to the first position (FIG. 6*a*) so as to be prepared to extract the next one of the plurality of test sensors. Once the test-sensor extractor 318 is moved back to its original position, the next test sensor is loaded into the test-sensor extractor 318 via the first mechanical mechanism 316 (e.g., a spring). When the lid 330 is in the closed position (FIG. 6*a*), the lid 330 seals the opening 320.

According to another embodiment, the test-sensor extractor may be shaped differently than depicted in FIGS. 6*a-c*. For example, the test-sensor extractor may include a generally horizontal portion and a second portion that extends from the cartridge when the lid is in the open position. The second portion may be shaped such that the lid engages the second portion and pushes it back into the cartridge.

The lid 330 of FIGS. 6*a*-6*c* works in connection with at least one retainer tab (retainer tabs 328*a*, 328*b*) as described above in connection with retainer tabs 154, 154*b*. Referring still to FIGS. 6*a*-6*c*, the cartridge 310 may also include a sealing mechanism such as a seal ridge 340 located generally around the periphery of the opening 320. The seal ridge 340 assists in maintaining a desirable seal with the lid 330 and functions in the same manner as the seal ridge 158 discussed above. It is also contemplated that a sealing mechanism may be located on the lid itself.

To assist in protecting the reagent(s) in the test sensors 314, desirable packaging material and/or desiccant material may be used. The cartridge 310 is typically packaged in material that prevents or inhibits air from entering into an interior of the housing 312 that contains the test sensors 314 as discussed above in connection with cartridge 10. Additionally, as discussed above in connection with cartridge 10, desiccant material 326 may be added to the cartridge 310.

Figure 7A:
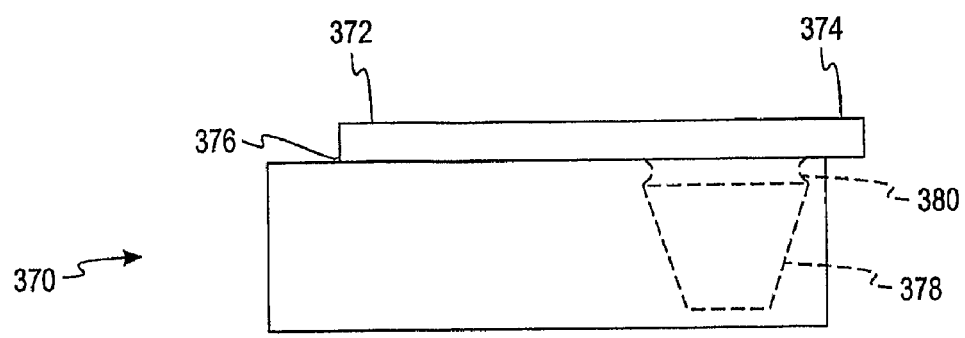
FIG. 7a is a front view of a lid in a closed position according to yet another embodiment.
Figure 7B:
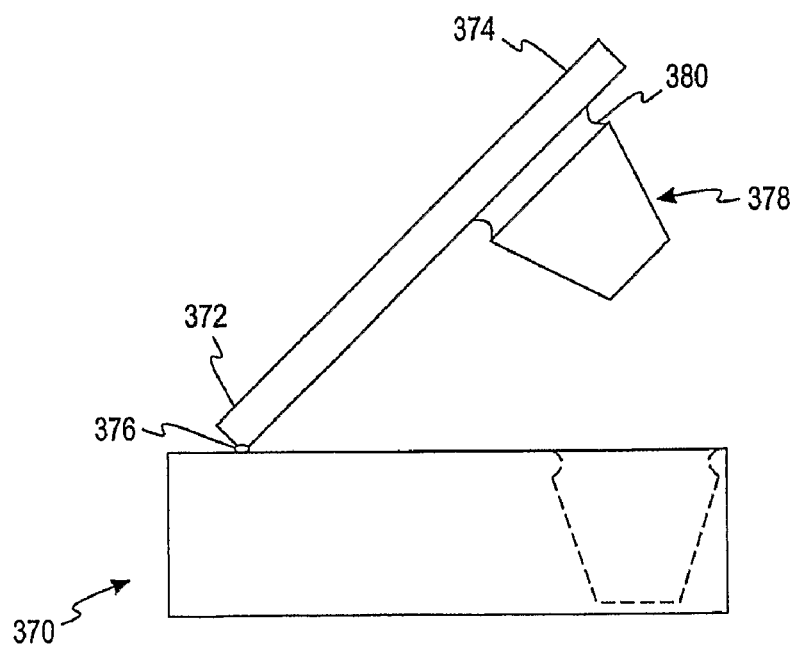
FIG. 7b is a front view of the lid of FIG. 7a in an open position.

It is contemplated that other lids may be used with the previously described cartridges and sensor-dispensing instruments. For example, according to another embodiment, a lid 370 may be used as depicted in FIGS. 7*a*, 7*b*. The lid 370 includes a first end 372 and a second end 374. The lid 370 is moveable between a closed position (FIG. 7*a*) and an open position (FIG. 7*b*) via a hinge 376 located at the first end 372 such that the lid 370 seals the opening in the closed position. The lid 370 includes a projection 378 located near or at the second end 374. The projection 378 extends generally downwardly into an interior of the cartridge. The projection 378 may form at least one detent 380 to assist in locking the cartridge.

Figure 8B:
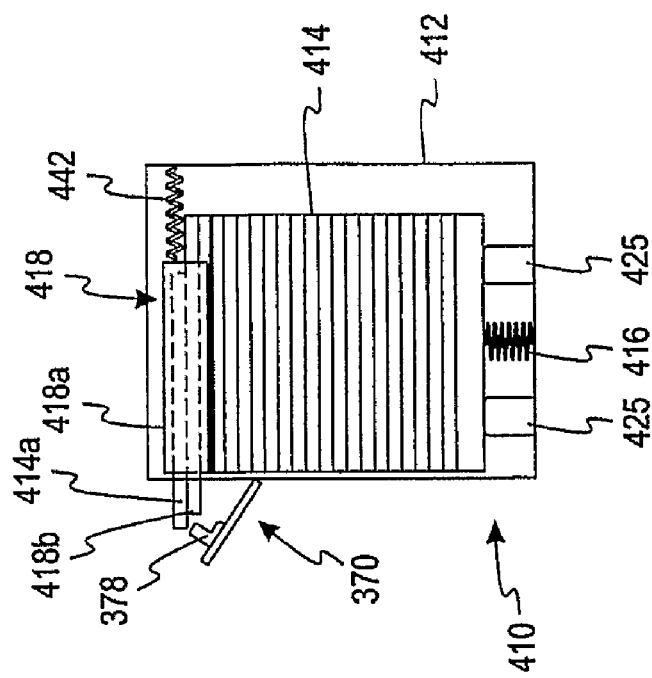
FIG. 8b is a front view of the cartridge of FIG. 8a in an open position.
Figure 8A:
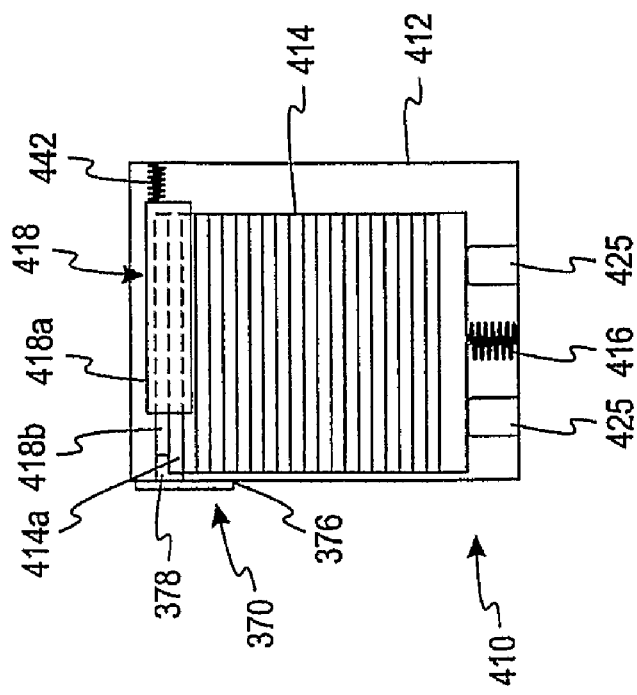
FIG. 8a is a front view of a cartridge in a closed position according to one embodiment.

One example of a cartridge that may be used with lid 370 is depicted in FIGS. 8*a*, 8*b*. A cartridge 410 of FIGS. 8*a*, 8*b*, comprises a housing 412, a plurality of test sensors 414, a first mechanical mechanism 416, and a second mechanical mechanism 442 and these function the same as described above with like parts in FIGS. 6a-6c. The cartridge also includes a test-sensor extractor 418 that includes a first portion 418a and a second portion 418b. In the open position, a user can grasp test sensor 414a and remove it manually from the cartridge 410. When the lid 370 is being moved to the closed position (FIG. 8a), the projection 378 of the lid 370 contacts the second portion 418b and pushes the test-sensor extraction 418 back into the cartridge 410. The lid may be open and closed using an automatic process that may, for example, be initiated by a user pressing a button. One example of an automatic process could include the plurality of test sensors being removed entirely using a motorized mechanism.

Figure 9B:
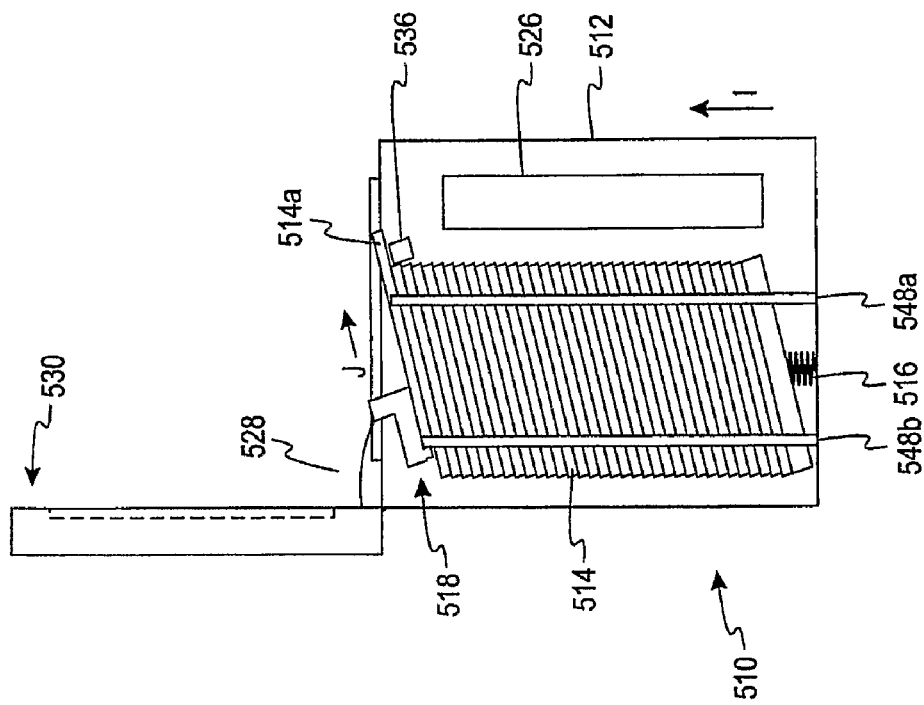
FIG. 9b is a front view of the cartridge of FIG. 9a in an open position.
Figure 9A:
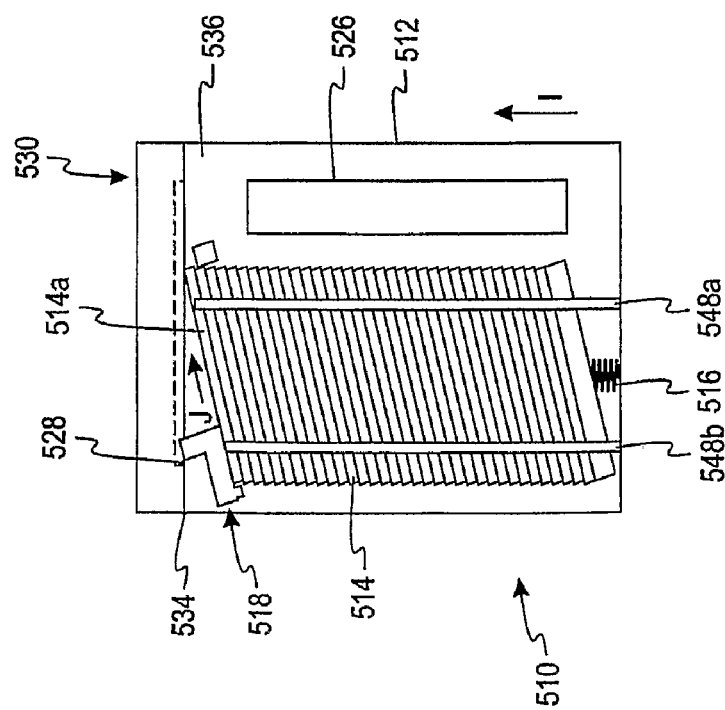
FIG. 9a is a front view of a cartridge in a closed position according to yet a further embodiment.

According to a further embodiment, a cartridge 510 of FIGS. 9a, 9b, comprises a housing 512, a plurality of test sensors 514, a mechanical mechanism 516, a pusher assembly 518 and a lid 530. The cartridge 510 is adapted to be disposable after each of the plurality of test sensors 514 has been used.

Referring to FIG. 9b, the housing 512 forms at least one opening 520 therethrough that allows the plurality of test sensors 514 to move therethrough one at a time and eventually exit the cartridge 510. The housing 512 may be formed of the same materials and processes as described above in connection with housing 12.

As shown in FIGS. 9a, 9b, the plurality of test sensors 514 is stacked in the housing 512 on an slant. The plurality of test sensors 514 is adapted to assist in testing at least one analyte as discussed above with respect to test sensors 14. To urge the stacked test sensors 514 in a first direction (in the direction of arrow I in FIGS. 9a, 9b), the mechanical mechanism 516 is used according to one embodiment. A stop member 536 may be included in the cartridge 510 to assist in preventing or inhibiting more than one test sensor from being extracted at a time. The mechanical mechanism 516 assists in positioning one of the plurality of test sensors 514 for eventual ejection from the cartridge 510 via the opening 520. The mechanical mechanism 516 may be a spring or the other devices described above in connection with mechanical mechanism 16.

The cartridge 510 also includes the pusher assembly 518 that is adapted to move between a first position (FIG. 9a) and a second position (FIG. 9b). The movement of the pusher assembly 518 is connected and controlled by the lid 530. The pusher assembly 518 may be attached to the lid 530 by a cam mechanism 528. It is also contemplated that the pusher assembly may be connected to the lid via other mechanisms such as a linkage.

The movement of the lid 530 from the closed position (FIG. 9a) to the open position (FIG. 9b) moves the pusher assembly 518 from the first position to the second position, which results in extracting one of the plurality of test sensors 514 at least partially through the opening 520. Specifically, when the lid 530 is moved to the open position, the pusher assembly 518 contacts moves the test sensor 514a (in the direction of arrow J) at least partially through the opening 520. According to one process, the lid 530 is manually moved between the open position and the closed position. It is contemplated that the lid 530 may be moved in an automatic process that is initiated, for example, by a user pressing a button. One example of an automatic process could include the plurality of test sensors being removed entirely using a motorized mechanism. The lid 530 may be moved between the open and the closed positions via a hinge 534. After the test sensor 514a is extracted at least partially through the opening 520, the test sensor 514a may then be manually extracted fully by the user.

When the lid 530 is moved back to the closed position, the lid 530 moves the pusher assembly 518 back into the cartridge 510. After the test sensor 514a has been extracted, the lid 530 is moved back to the closed position (FIG. 9a) and the pusher assembly 518 is moved back to the first position (FIG. 9a) so as to be prepared to extract the next one of the plurality of test sensors 514. Once the pusher assembly 518 is moved back to its original position, the next test sensor is loaded into the pusher assembly 518 via the mechanical mechanism 516 (e.g., a spring). To assist in properly guiding and positioning the next test sensor, a plurality of tracks 548a, 548b may be employed. When the lid 530 is in the closed position (FIG. 9a), the lid 530 seals the opening 520.

The cartridge 510 may also include a sealing port located generally around the periphery of the opening 520. The sealing port assists in maintaining a desirable seal with the lid 530 and functions in the same manner as the sealing port 22 discussed above.

To assist in protecting the reagent(s) in the test sensors 514, desirable packaging material and/or desiccant material may be used. The cartridge 510 is typically packaged in material that prevents or inhibits air from entering into an interior of the housing 512 that contains the test sensors 514 as discussed above in connection with cartridge 10. Additionally, as discussed above in connection with cartridge 10, desiccant material 526 may be added to the cartridge 510.

According to an alternative embodiment, a cartridge 540 of FIGS. 9c, 9d may employ a second mechanical mechanism such as the second mechanical mechanism 542 in FIGS. 6a-c. In this embodiment, the second mechanical mechanism is adapted to urge the plurality of test sensors 514 in a second direction (in the direction of arrow J in FIGS. 9c, 9d). The second mechanical mechanism 542 may be a spring or other devices described above in connection with mechanical mechanism 16. The second mechanical mechanism would push one of the plurality of test sensors 514 from the cartridge 540 when the lid 530 is moved from the closed position to the open position. When the lid 530 is moved from the open position to the closed position, the lid 530 pushes the second mechanical mechanism 542 back to its retracted position (FIG. 9c).

Figure 10A:
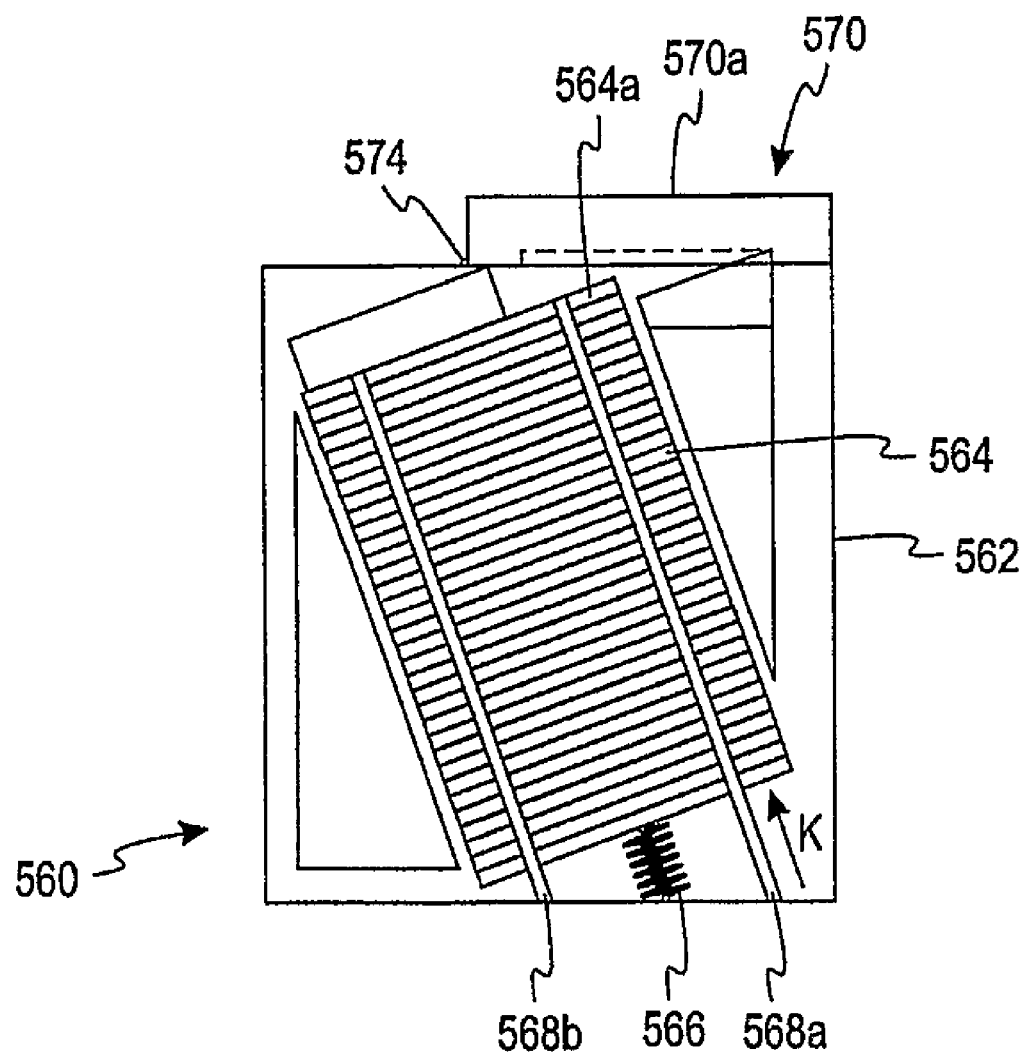
FIG. 10a is a front view of a cartridge according to yet another embodiment in a closed position.
Figure 10B:
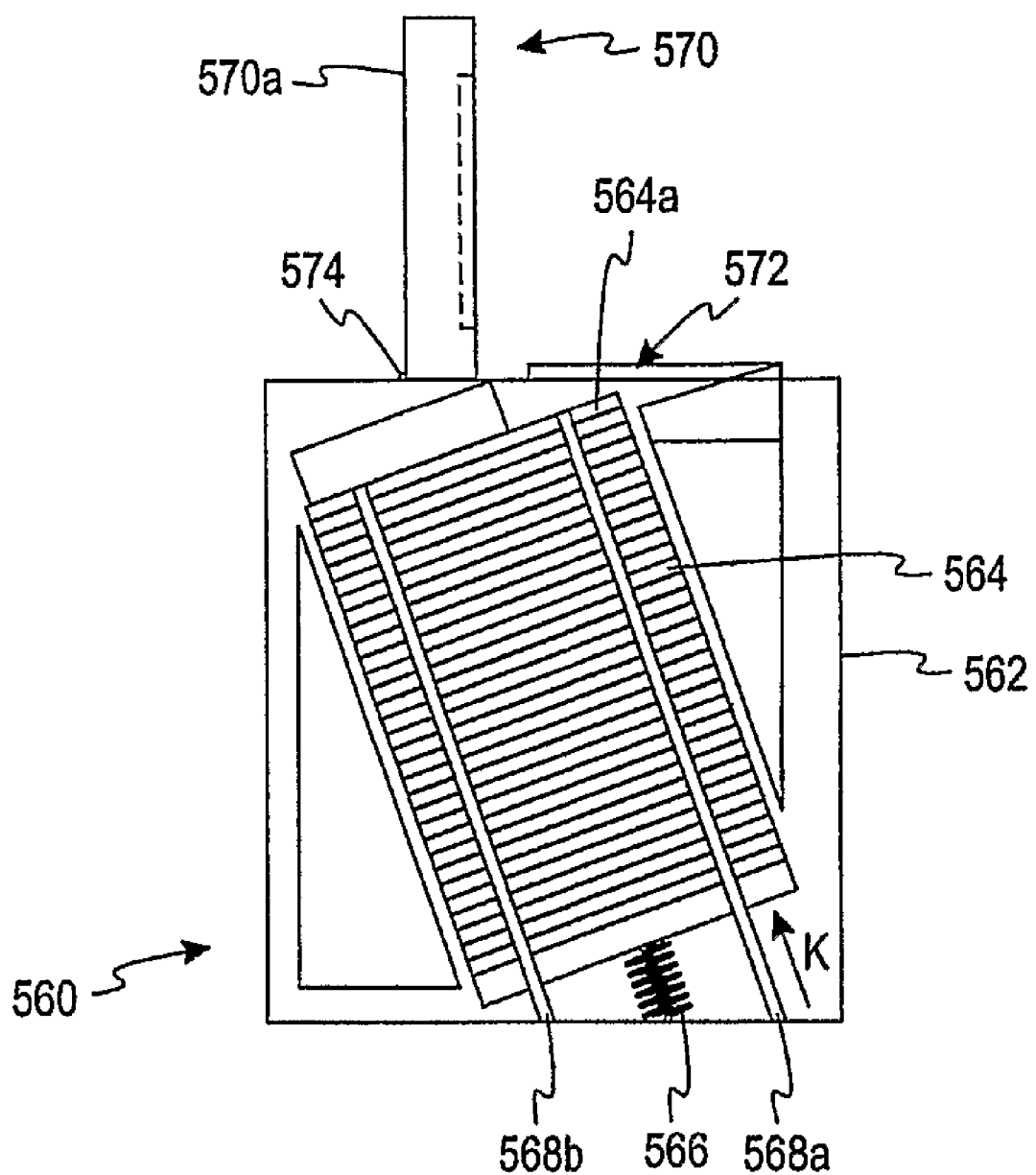
FIG. 10b is a front view of the cartridge of FIG. 10a in an open position.

According to another embodiment, a cartridge 560 of FIGS. 10a, 10b comprises a housing 562, a plurality of test sensors 564, a mechanical mechanism 566 and a lid 570. The cartridge 560 is adapted to be disposable after each of the plurality of test sensors 564 has been used.

Referring to FIG. 10b, the housing 562 forms at least one opening 572 therethrough that allows the plurality of test sensors 564 to move therethrough one at a time and eventually exit the cartridge 560. The housing 562 may be formed of the same materials and processes as described above in connection with housing 12.

As shown in FIGS. 10a, b, the plurality of test sensors 564 is stacked in the housing 562 on an slant. The plurality of test sensors 564 is adapted to assist in testing at least one analyte as discussed above with respect to test sensors 14. To urge the stacked test sensors 564 in a first direction (in the direction of arrow K in FIGS. 10a, b), the mechanical mechanism 566 is used according to one embodiment. The mechanical mechanism 566 assists in positioning one of the plurality of test sensors 564 for eventual ejection from the cartridge 560 via the opening 572. The mechanical mechanism 566 may be a spring or the other devices described above in connection with mechanical mechanism 16.

The movement of the lid 570 from the closed position (FIG. 10a) to the open position (FIG. 10b) enables a user to manually extract test sensor 564a through the opening 572. The lid 570 may be moved between the open and the closed positions via a hinge 574. It is contemplated that other lids may be used with cartridge 560. For example, according to additionally embodiments, the cartridge 560 may, for example, replace lid 570 with lid 150 of FIGS. 4a, 4b or lid 370 of FIGS. 7a, 7b.

After the test sensor 564a has been extracted, the next test sensor is moved in the direction of arrow K via the mechanical mechanism 566 (e.g., a spring). To assist in properly guiding and positioning the next test sensor, a plurality of tracks 568a, 568b may be employed. When the lid 570 is in the closed position, the lid 570 seals the opening 572.

The cartridge 560 may also include a sealing mechanism such as a sealing port located generally around the periphery of the opening 572. The sealing port assists in maintaining a desirable seal between the lid 570 and the opening 572 and functions in the same manner as the sealing port 22 discussed above. A sealing mechanism may be located on the lid 570 to form a desirable seal between the lid 570 and the opening 572.

To assist in protecting the reagent(s) in the test sensors 574, desirable packaging material and/or desiccant material may be used. The cartridge 560 is typically packaged in material that prevents or inhibits air from entering into an interior of the housing 562 that contains the test sensors 564 as discussed above in connection with cartridge 10. Additionally, as discussed above in connection with cartridge 10, desiccant material may be added to the cartridge 560.

According to a further embodiment, a cartridge 610 of FIGS. 11a-g comprises a housing 612, a plurality of test sensors 614, a plurality of mechanical mechanisms 616a, 616b, and a lid 630. The housing 612 forms at least one opening 620 therethrough. The housing 612 may be formed of the same materials and processes as described above in connection with housing 12.

As shown in FIG. 11a, for example, the plurality of test sensors 614 is stacked in the housing 612. The plurality of test sensors 614 is adapted to assist in testing at least one analyte as discussed above with respect to test sensors 14. Additionally, as shown in FIG. 11a, each of the plurality of test sensors 614 further includes a plurality of sensor electrical contacts 632a-c.

To urge the stacked test sensors 614 in a first direction (in the direction of arrow L in FIG. 11a), the plurality of mechanical mechanisms 616a, 616b is used according to one embodiment. The plurality of mechanical mechanisms 616a, 616b assists in positioning one of the plurality of test sensors 614 for eventual ejection from the cartridge 610 via the opening 620. The plurality of mechanical mechanisms 616a, 616b may be a spring or the other devices described above in connection with mechanical mechanism 16. It is contemplated that only one mechanical mechanism may be used to urge the stacked test sensors in the cartridge 610. To assist in guiding the mechanical mechanisms 616a, 616b upwardly (in the direction of arrow L in FIG. 11a), the housing 612 may be formed with at least one prong or extension 625.

Figure 11C:
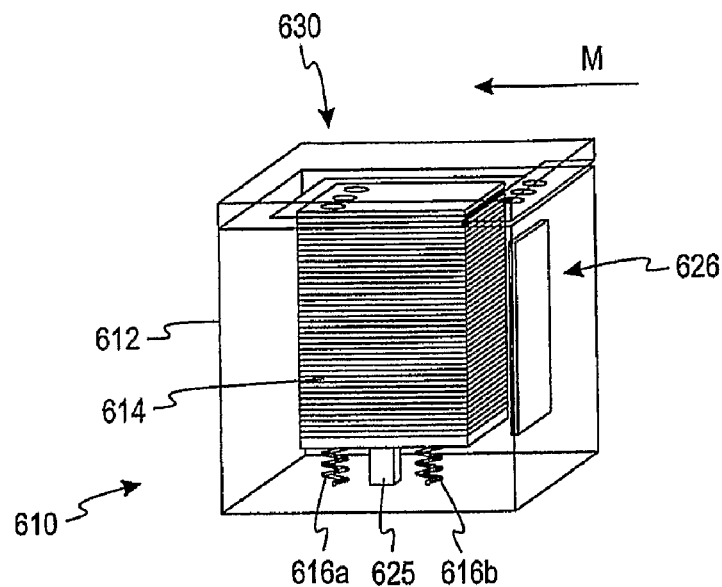
FIG. 11c is a perspective view of the cartridge of FIG. 11a with the lid in a closed position.
Figure 11D:
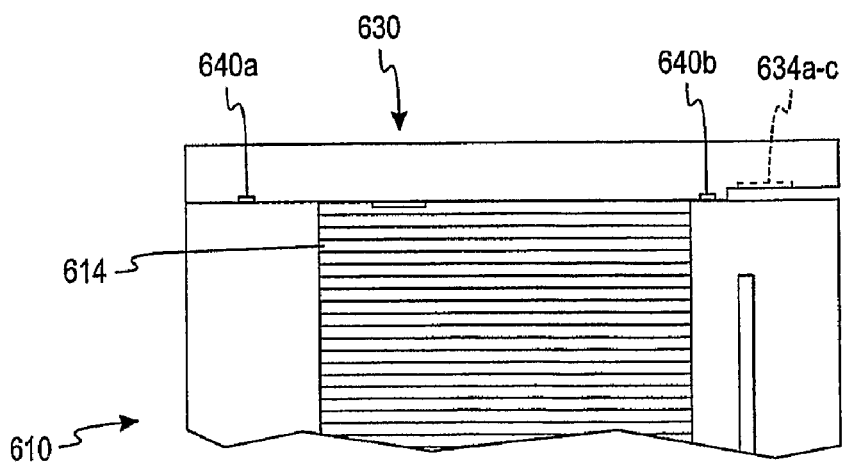
FIG. 11d is an enlarged front view of the lid and cartridge of FIG. 11c.

The movement of the lid 630 from the closed position (FIGS. 11c, 11d) to the open position (FIG. 11e) and back to the closed position (FIG. 11f) extracts one of the plurality of test sensors 614 at least partially through the opening 620. FIG. 11d shows the lid 630 and the plurality of test sensors 614 of FIG. 11c in more detail. According to one process, the lid 630 is manually moved from between the open position and the closed position.

According to another process, the lid 630 may be automatically moved between the open position and the closed position by, for example, pressing a button. One example of an automatic process could include the plurality of test sensors being removed entirely using a motorized mechanism to move the lid.

Figure 11F:
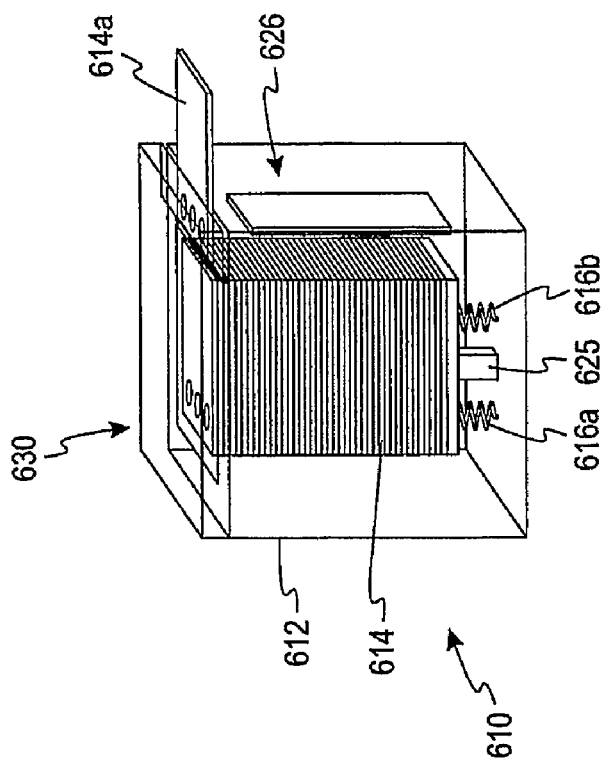
FIG. 11a is an exploded front perspective view of a cartridge according to another embodiment.
FIG. 11b is a side view of the cartridge of FIG. 11a in a closed position.
FIGS. 11e,f are perspective views of the cartridge of FIG. 11a with the lid being in respective open and closed positions.
FIG. 11g is an enlarged view of the lid with a test sensor of FIG. 11f.
Figure 11E:
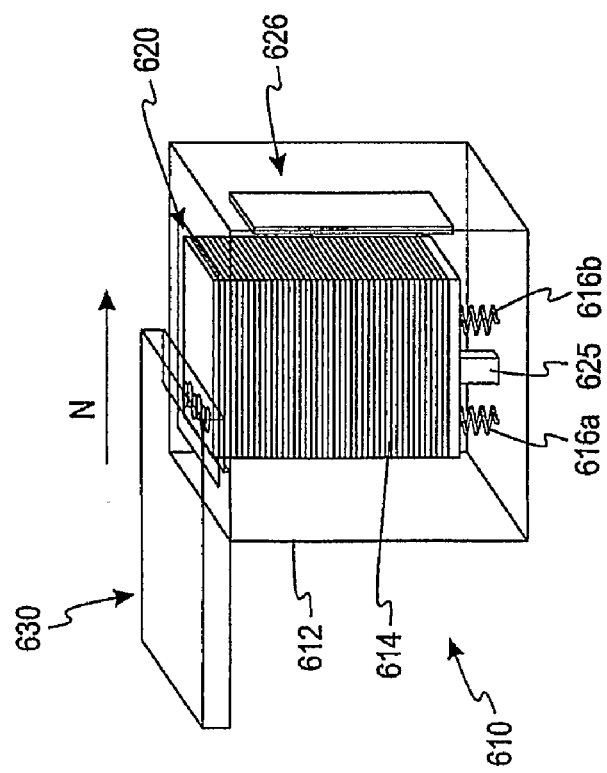
Figure 11G:
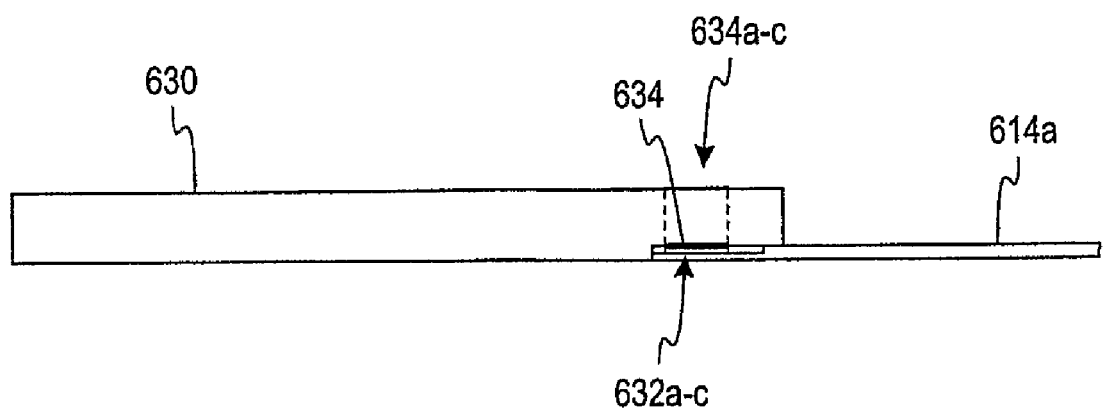

The lid 630 includes at least one electrical contact. As shown in, for example, FIG. 11a, the lid 630 includes a plurality of lid electrical contacts 634a-c. After the lid 630 is moved in the direction of arrow M from the closed position (FIG. 11c) to the open position (FIG. 11e), at least one of the plurality of lid electrical contacts the at least one sensor electrical contact. More specifically, the plurality of lid electrical contacts 634a-c contacts a respective one of the plurality of sensor electrical contacts 632a-c. The lid 630 moves from the open position (FIG. 11e) in the direction of arrow N to the closed position (FIG. 11f). During this movement of the lid 630 in the direction of arrow N, test sensor 614a is extracted at least partially from the cartridge 610. FIG. 11g shows the lid 630 and test strip 614a in the closed position of FIG. 11f in more detail. The lid 630 may be configured to include an additional step to accommodate a second step, if present, in one of the plurality of test sensors 614.

To assist in moving and sealing the lid 630, a plurality of retainer tabs 636a, 636b as shown in FIG. 11b may be formed on the cartridge 610. Specifically, the plurality of retainer tabs 636a, 636b applies downward pressure to the lid 630, which assists in providing an enhanced seal of the lid 630 to the remainder of the cartridge 610. The cartridge 610 may also include a plurality of seals 640a, 640b such as shown in FIG. 11d. Additionally, the cartridge may include at least one détente and corresponding recess that assists in providing a user with an indication that the lid 630 is in a closed position.

To assist in protecting the reagent(s) in the test sensors 614, desirable packaging material and/or desiccant material may be used. The cartridge 610 is typically packaged in material that prevents or inhibits air from entering into an interior of the housing 612 that contains the test sensors 614 as discussed above in connection with cartridge 10. Additionally, as discussed above in connection with cartridge 10, desiccant material 626 may be added to the cartridge 610.

Figure 12A:
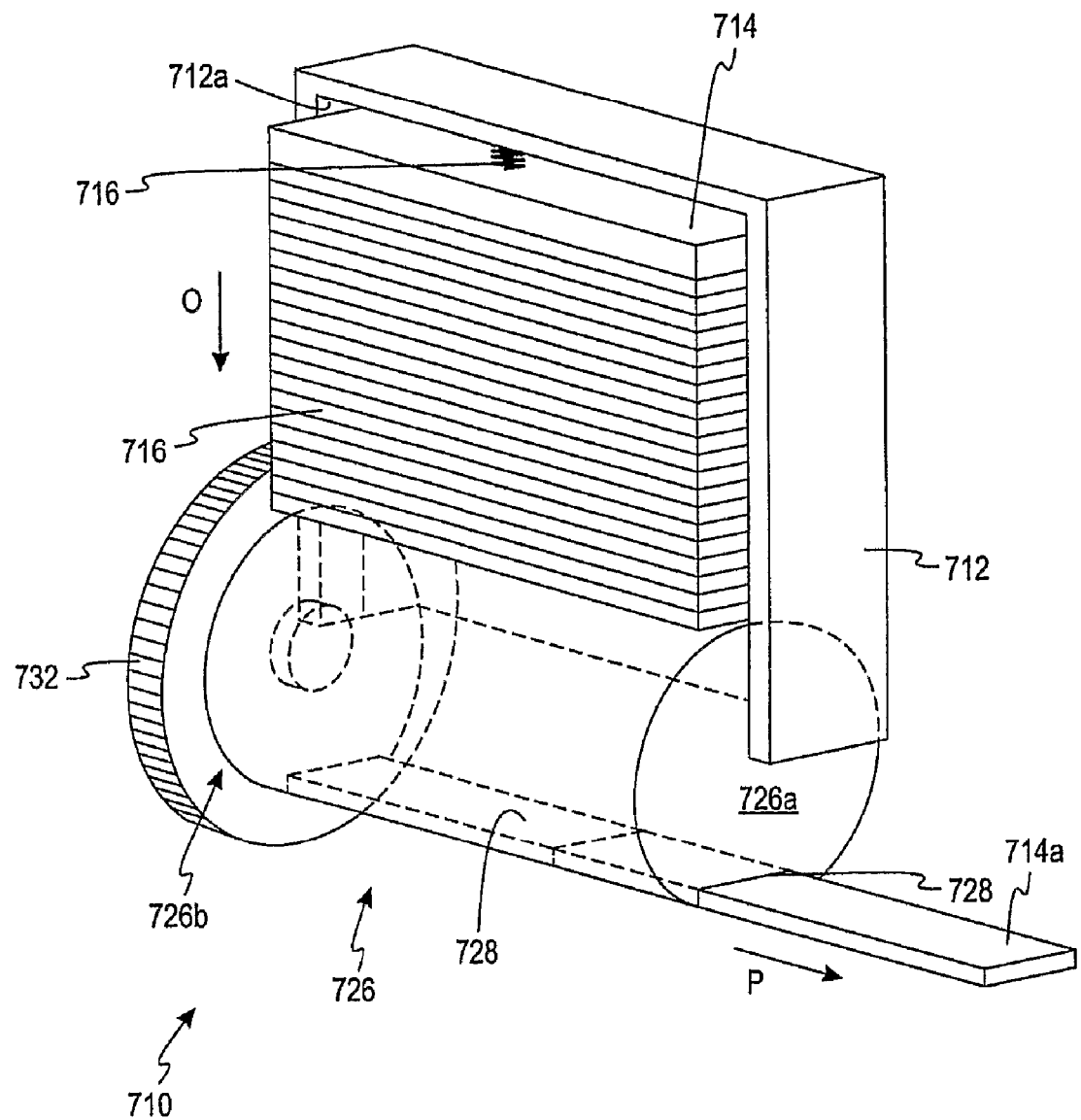
FIG. 12a is a front perspective view of a cartridge according to a further embodiment.
Figure 12B:
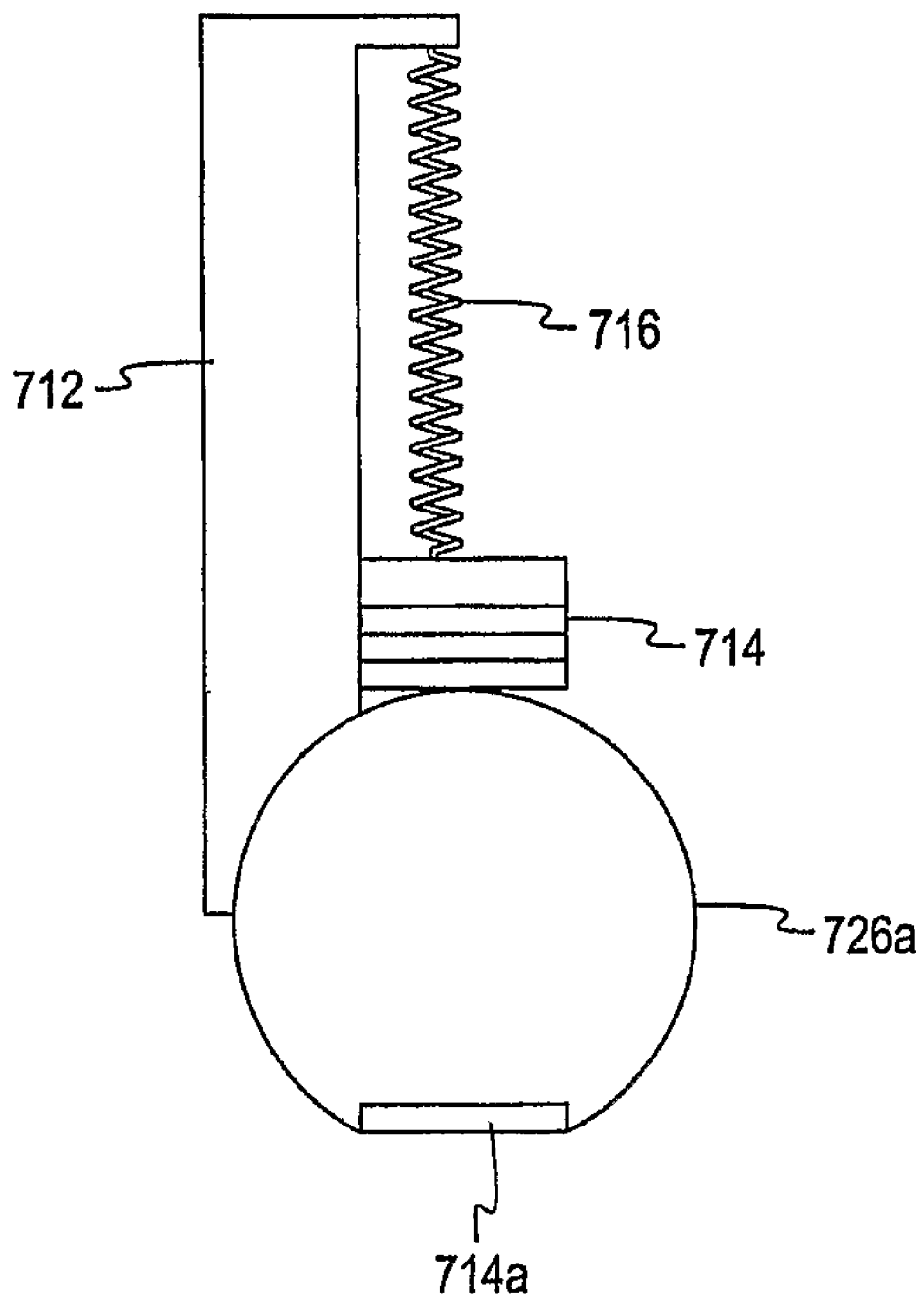

According to a further embodiment, a cartridge 710 of FIG. 12 comprises a housing 712, a plurality of test sensors 714, a mechanical mechanism 716 and a rotatable drum 726. The housing 712 has an interior portion 712a. The housing 712 may be formed of the same materials and processes as described above in connection with housing 12.

As shown in FIG. 12, the plurality of test sensors 714 is stacked in the housing 712. The plurality of test sensors 714 is adapted to assist in testing at least one analyte as discussed above with respect to test sensors 14.

To urge the stacked test sensors 714 in a first direction (in the direction of arrow O in FIG. 12), the mechanical mechanism 716 is used according to one embodiment. The mechanical mechanism 716 assists in positioning one of the plurality of test sensors 714 for eventual ejection from the cartridge 710 in conjunction with the rotatable drum 726. The mechanical mechanism 716 may be a spring or the other devices described above in connection with mechanical mechanism 16. It is contemplated that at least two mechanical mechanisms may be used to urge the stacked test sensors in the cartridge 710. To assist in guiding the mechanical mechanism 716 in the direction of arrow O in FIG. 12, the housing 712 may be formed with a plurality of prongs or extensions.

To assist in the extraction of the plurality of test sensors 714 from the cartridge 710, the rotatable drum 726 forms at least one notch 728 therein. The rotatable drum 726 is coupled to the interior portion 712a of the housing 712. The rotatable drum 726 may be coupled to the interior portion 712a by a push-fit attachment. It is contemplated that the rotatable drum may be coupled to the interior portion by other techniques such as spring loading. In a desired embodiment, the rotatable drum 726 is in sealing engagement with the interior portion 712a. For example, a section of the interior portion 712a may include a seal that is engaged by the drum 726. In such an embodiment, opposing surfaces 726a, 726b of the drum 726 are in sealingly engagement with the interior portion 712a. In another embodiment, the opposing surfaces 726a, 726b may include a respective seal that engages with a respective section of the interior portion 712a.

The at least one notch 728 is adapted to receive exactly one test sensor, such as test sensor 714a of FIG. 12. During the movement of the rotatable drum 726 from a first position to a second position, the plurality of test sensors 714, one at a time, is extracted from the cartridge 710. To assist in rotating the drum 726, a wheel 732 may be included on the cartridge 710 as shown in FIG. 12. One example of a wheel that may be used is a twist wheel. It is contemplated that other types of mechanisms may be used to rotate the drum such as a gear assembly that could be linked to a slide mechanism, or an electric or spring-driven motor and gear box.

The cartridge 710 may further include an ejector mechanism that is adapted to at least partially remove the plurality of test sensors 714, one at a time, from the at least one notch 728 formed in the drum 726 in the direction of arrow P. FIG. 12 depicts the test sensor 714a being partially removed from the cartridge 710.

To assist in protecting the reagent(s) in the test sensors 714, desirable packaging material and/or desiccant material may be used. The cartridge 710 is typically packaged in material that prevents or inhibits air from entering into an interior of the housing 712 that contains the test sensors 714 as discussed above in connection with cartridge 10. Additionally, as discussed above in connection with cartridge 10, desiccant material may be added to the cartridge 710.

Figure 13A:
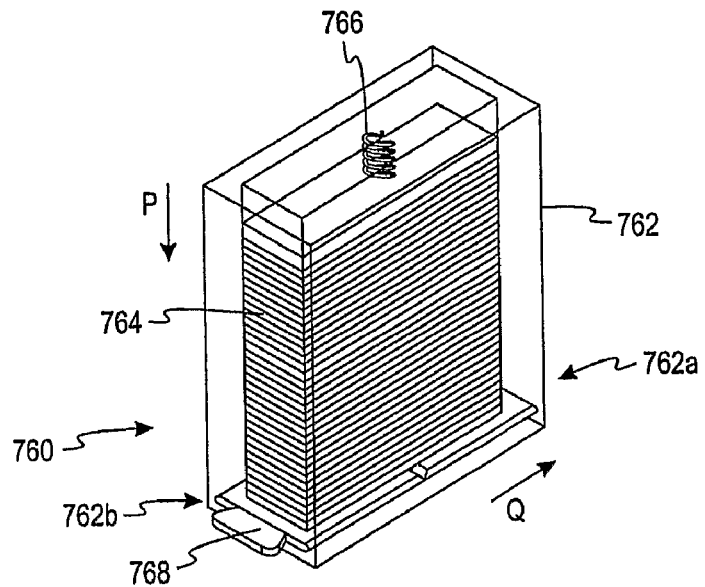
FIG. 13a is a front perspective view of a cartridge according to another embodiment.

According to yet another embodiment, a cartridge 760 of FIG. 13a comprises a housing 762, a plurality of test sensors 764, a mechanical mechanism 766 and a test-sensor extractor 768. The housing 762 forms at least two openings 762a,b therethrough. The housing 762 may be formed of the same materials and processes as described above in connection with housing 12.

As shown in FIG. 13a, the plurality of test sensors 764 is stacked in the housing 762. The plurality of test sensors 764 is adapted to assist in testing at least one analyte as discussed above with respect to test sensors 14.

To urge the stacked test sensors 764 in a first direction (in the direction of arrow P in FIG. 13a), the mechanical mechanism 766 is used according to one embodiment. The mechanical mechanism 766 assists in positioning one of the plurality of test sensors 764 for eventual ejection from the cartridge 760 in conjunction with an ejector mechanism to be discussed below. The mechanical mechanism 766 may be a spring or the other devices described above in connection with mechanical mechanism 16. It is contemplated that at least two mechanical mechanisms may be used to urge the stacked test sensors 764 in the cartridge 760.

The test-sensor extractor 768 is adapted to carry and extract the plurality of test sensors 764, one at a time, in a second direction (direction of arrow Q) at least partially through an opening 762a. For enhanced clarity of the test-sensor-extractor 768 in the cartridge 760, the plurality of test sensors except for test sensor 764a have been omitted from FIG. 13b. Additionally, the test sensor extractor 768 is also depicted in FIG. 13c.

Figure 13B:
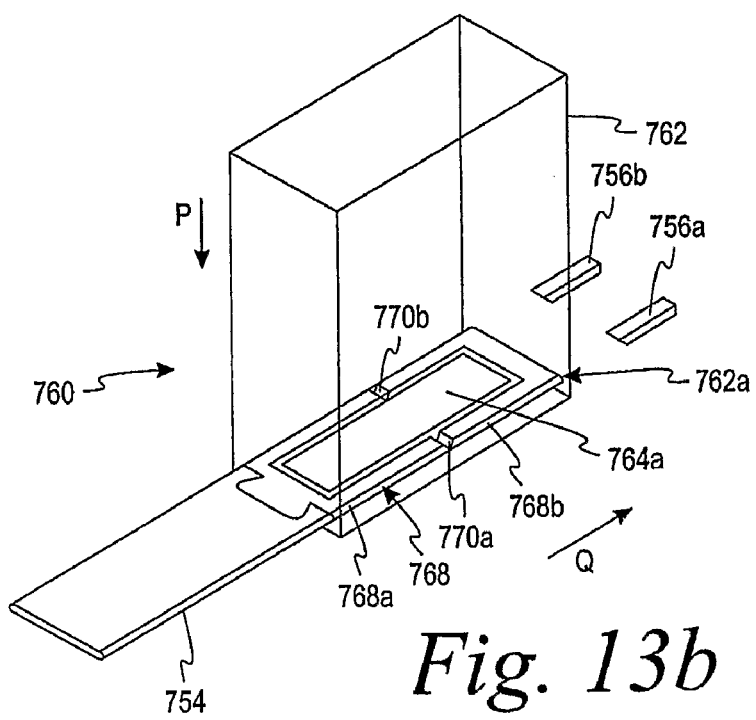
FIG. 13b is a front perspective view of the cartridge of FIG. 13a without the plurality of test sensors and an ejector mechanism according to another embodiment.
Figure 13C:
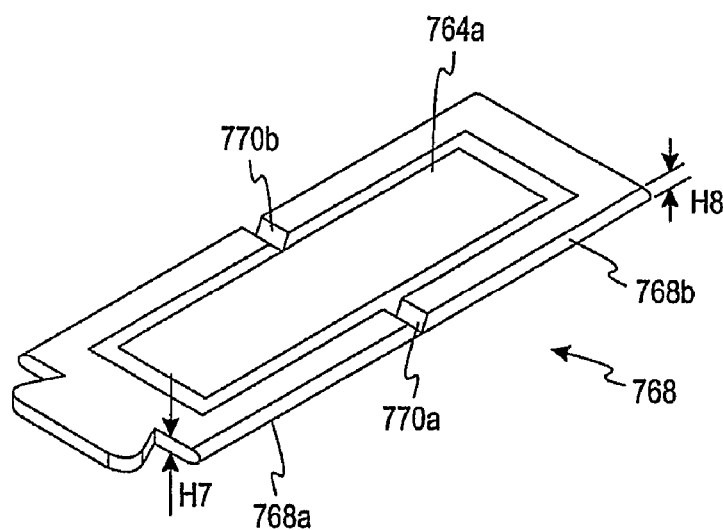
FIG. 13c is a front perspective view of the test-sensor extractor of FIG. 13b with a test sensor.

As shown in FIGS. 13b,13c, the test-sensor extractor 768 has a first portion 768a and a second portion 768b. Referring to FIG. 13c, the thickness H7 of the first portion 768a is typically less than the thickness of one of the plurality of test sensors 764, while the thickness H8 of the second portion 768b is typically greater than the thickness of one of the plurality of test sensors 764. Referring back to FIGS. 13a, 13b, the test-sensor extractor 768 moves a test sensor in the direction of arrow Q from the cartridge 760. The first portion 768a and the second portion 768b are connected by at least one hinge. The test-sensor extractor 768 includes a plurality of hinges 770a,b. The second direction (in the direction of arrow Q in FIGS. 13a,13b) and the first direction (in the direction of arrow P in FIGS. 13a,13b) are generally perpendicular to each other. Sealing of the openings 762a,b may be achieved in the cartridge 760 by having a generally snug fit between an interior wall of the housing 762 and the test-sensor extractor 768.

Figure 13D:
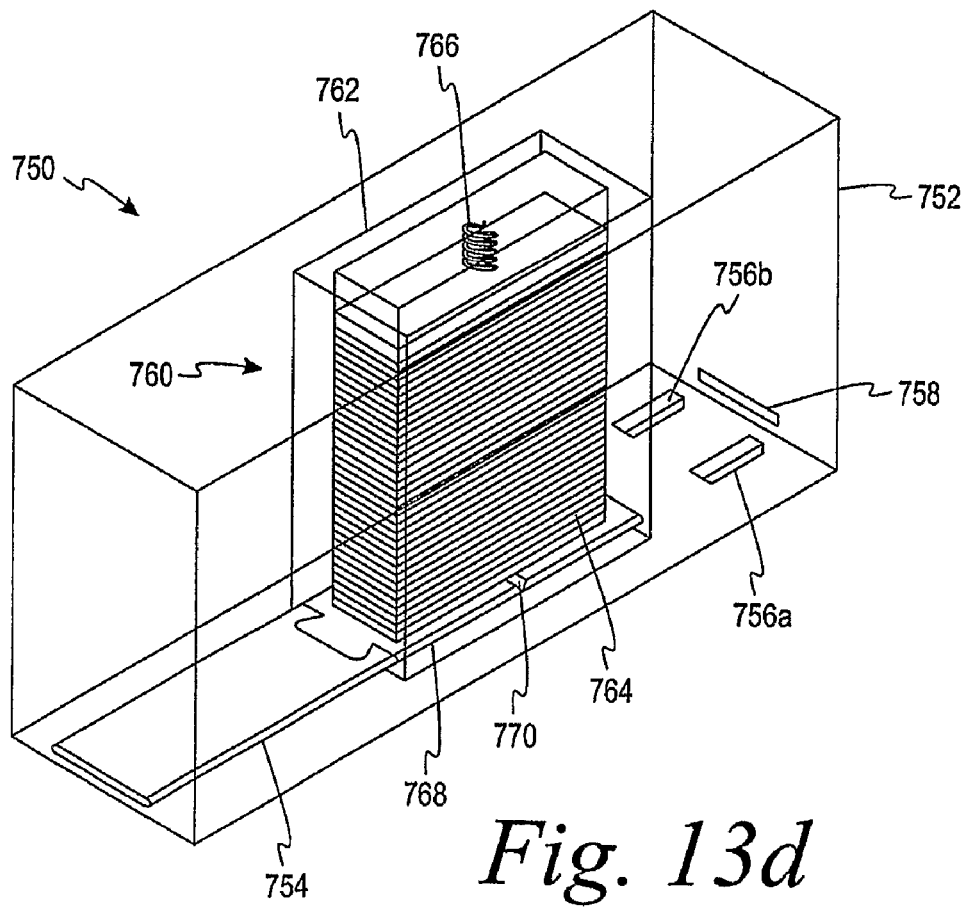
FIG. 13d is a perspective view of a sensor-dispensing instrument with the cartridge of FIG. 13a and the ejector mechanism of FIG. 13b.

The cartridge 760 is adapted to be used with a sensor-dispensing instrument. According to one embodiment, a sensor-dispensing instrument 750 of FIG. 13d comprises the cartridge 760, a housing 752, an ejector mechanism 754 and at least one deflector (deflectors 756a,b). The housing 752 forms a dispensing outlet 758 and is adapted to receive the cartridge 760.

Figure 13E:
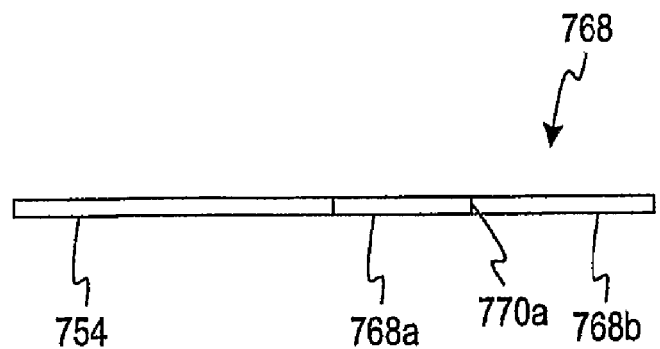
FIGS. 13e,f depict an ejector mechanism contacting the test-sensor extractor of FIG. 13c.

The ejector mechanism 754 is adapted to extend through at least one of the openings 762b (see FIG. 13a) and contact the test-sensor extractor 768. The ejector mechanism 754 is shown contacting the test-sensor extractor 768 in FIGS. 13e, 13f. As the ejector mechanism 754 continues to push the test-sensor extractor 768 (along with one of the plurality of test sensors 764a) in the direction of arrow Q (see FIGS. 13b,13d), the second portion 768b contacts the deflectors 756a,b (see FIG. 13f).

Figure 13F:
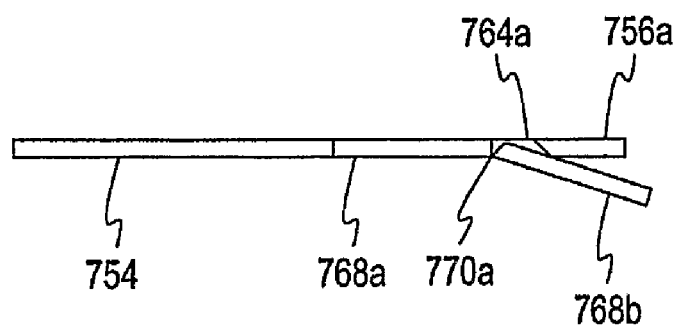

The deflectors 756a,b are adapted to contact and deflect the second portion 768b of the test-sensor extractor 768 and assist in extracting the plurality of test sensors 764, one at a time, at least partially through the dispensing outlet 758 (see FIG. 13d) When the second portion 768b contacts the deflectors 756a,b, the second portion 768b is directed downwardly as viewed in FIG. 13f via the hinges 770a,b. The test sensor 764a, however, continues to proceed in the direction of arrow Q.

According to one method, the ejector mechanism 754 may be released from its initial position (FIG. 13d) by, for example, a button that initiates a motor. The ejector mechanism 754 may be spring loaded to assist in returning to its initial position. Alternatively, the ejector mechanism 754 may be initiated, for example, by moving a slider, which is mechanically connected to the ejector mechanism, in the direction of arrow Q.

Figure 14A:
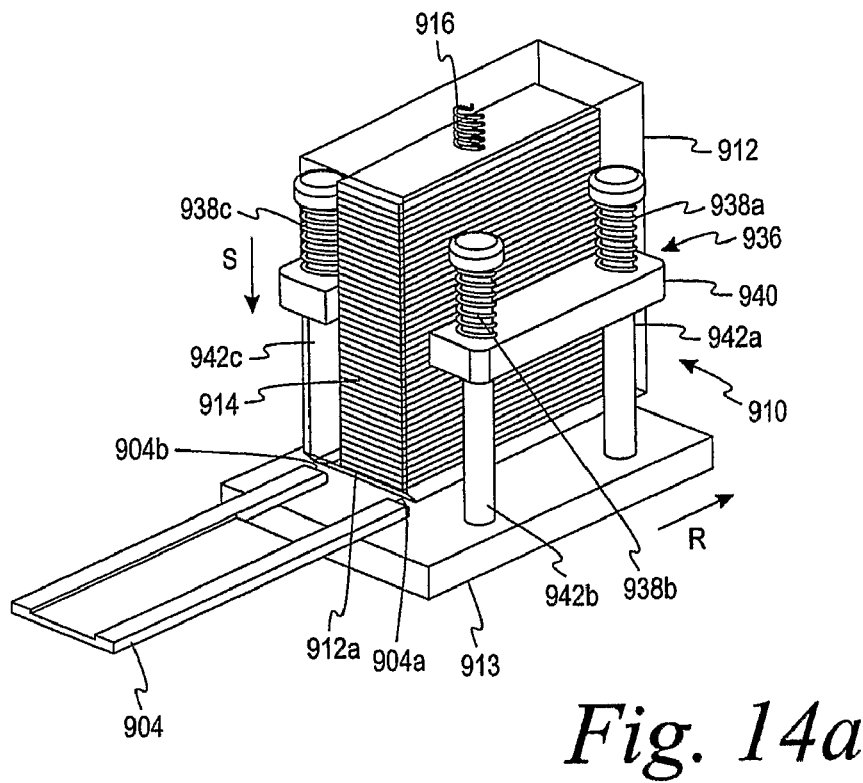
FIG. 14a is a front perspective view of a cartridge in a closed position and an ejector mechanism according to another embodiment.
Figure 14B:
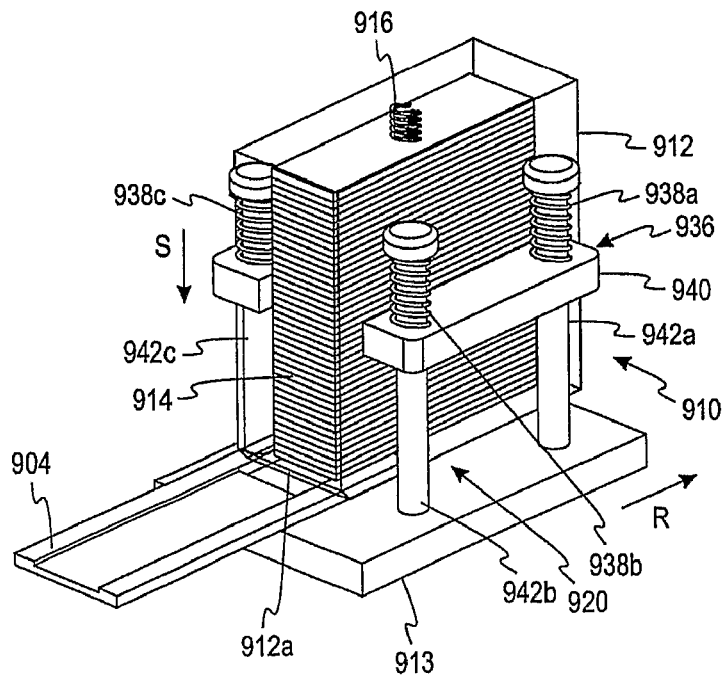

According to another embodiment, a cartridge 910 of FIGS. 14a,14b comprises a housing 912, a base 913, a plurality of test sensors 914, an interior mechanical mechanism 916 and an exterior spring mechanism 936. The housing 912 forms at least one opening 920 therethrough. The housing 912 may be formed of the same materials and processes as described above in connection with housing 12. The base 913 is adapted to be in sealing engagement with the housing 912 in a first position (FIG. 14a).

As shown in FIG. 14a, the plurality of test sensors 914 is stacked in the housing 912. The plurality of test sensors 914 is adapted to assist in testing at least one analyte as discussed above with respect to test sensors 14.

To urge the stacked test sensors 914 in a first direction (in the direction of arrow S in FIG. 14a), the interior mechanical mechanism 916 is used according to one embodiment. The interior mechanical mechanism 916 assists in positioning one of the plurality of test sensors 914 for eventual ejection from the cartridge 910 in conjunction with an ejector mechanism to be discussed below. The interior mechanical mechanism 916 may be a spring or the other devices described above in connection with mechanical mechanism 16. It is contemplated that at least two mechanical mechanisms may be used to urge the stacked test sensors 914 in the cartridge 910.

According to one embodiment, the exterior spring mechanism 936 is attached to the housing 912 and the base 913 and is adapted to assist in sealingly engaging the housing 912 and the base 913. In the first position (FIG. 14*a*), the housing 912 and the base 913 are in sealing engagement. In the second position (FIG. 14*b*), however, the housing 912 and base 913 are spaced apart by an ejector mechanism 904.

As shown in FIG. 14*a*, the exterior spring mechanism 936 includes a plurality of springs 938, a slidable holder 940 and a plurality of shafts 942 (only shafts 942*a-c* are shown in FIGS. 14*a*,14*b*). The exterior spring mechanism 936 keeps the housing 912 sealed against the base 913. The exterior spring mechanism 936 specifically includes four springs (only springs 938*a-c* are shown in FIGS. 14*a*,14*b*) that are installed to keep the housing 912 sealed against the base 913. It is contemplated that more or less springs may be used to maintain a sealing relationship between the housing 912 and the base 913. For example, the exterior spring mechanism may include two springs. The slidable holder 940 is attached to the housing 912 and slides along shafts 942*a,b*.

The cartridge 910 is adapted to be used in a sensor-dispensing instrument. According to one embodiment, the cartridge 910 is used with a sensor-dispensing instrument 900. The sensor-dispensing instrument 900 includes a housing 902 and an ejector mechanism 904. The housing 902 forms a dispensing outlet 906 and is adapted to received the cartridge 910.

Figure 14C:
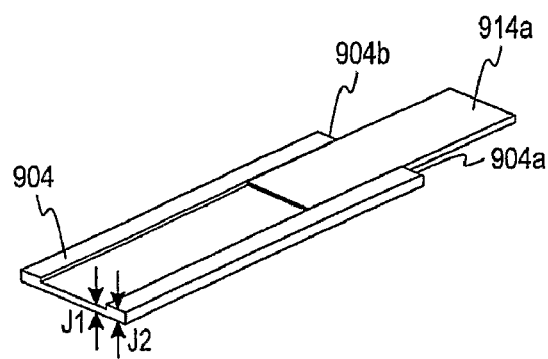
FIG. 14c is a perspective view of the ejector mechanism of FIG. 14b with a test sensor.
Figure 14D:
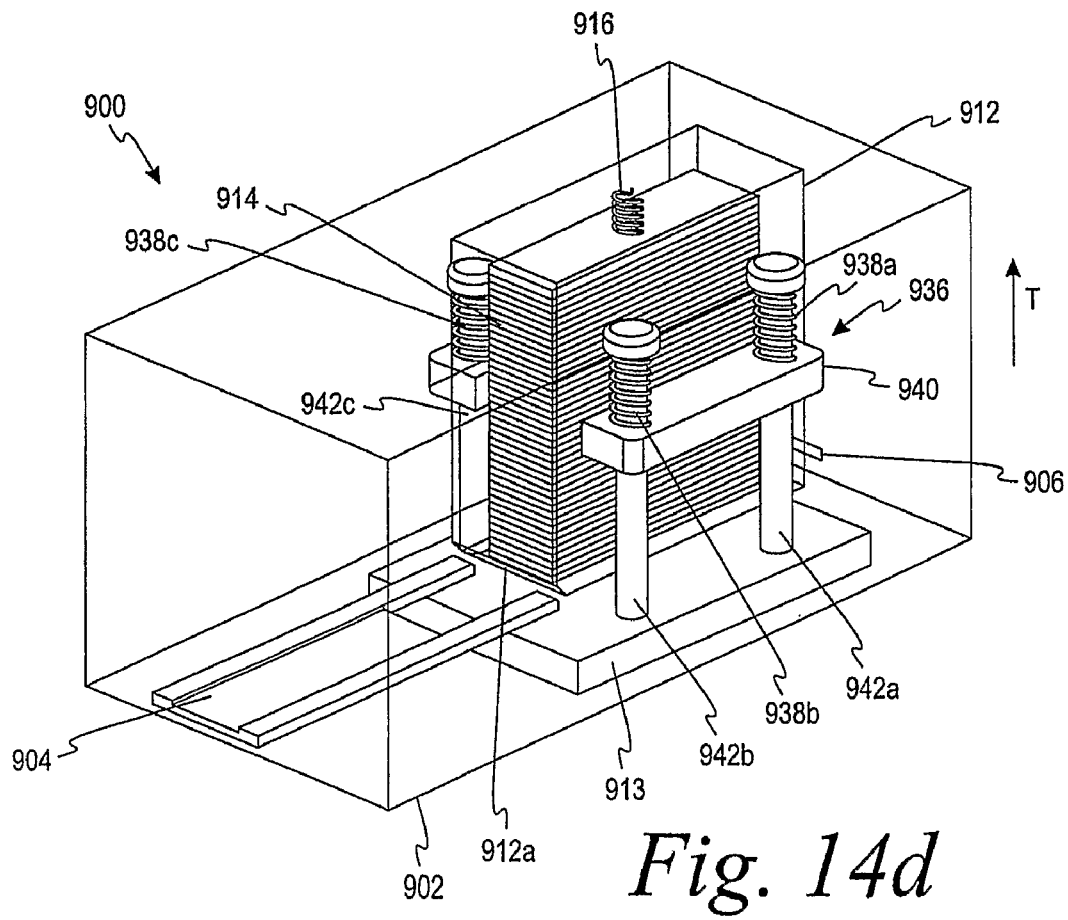
FIG. 14d is a perspective view of a sensor-dispensing instrument with the cartridge and ejector mechanism of FIG. 14a according to another embodiment.

The ejector mechanism 904 is adapted to move and be inserted between the 912 housing and the base 913 (see FIGS. 14*a,b*). Referring to FIG. 14*c*, the thickness J1 of 904 is typically less than the thickness of one of the plurality of test sensors 914, while the thickness J2 of 904 is typically greater than the thickness of one of the plurality of test sensors 914, but less than the thickness of two test sensors. Specifically, the ejector mechanism 904 moves in the direction of arrow R, contacts and forces the housing 912 upwards (against the force of the plurality of springs 938) and extracts a test sensor 914*a* at least partially from the dispensing outlet 906 of the cartridge 910. As the housing 912 is raised upwards (in the direction of arrow T of FIG. 14*d*), the plurality of test sensors 914 remain in contact with the base 913 due to the force of mechanical mechanism 916. To assist in moving the housing 912 in the direction of arrow T, an end 912*a* of the housing 912 and at least one end 904*a,b* of the ejector mechanism 904 may be chamfered.

If electrochemical sensors are used in the sensor-dispensing instrument, then one of the test sensors will be positioned appropriately to an electrical contact. It is contemplated that the electrical contact includes a plurality of contacts that is positioned to correspond to the test sensor. The front end of the sensor then receives, for example, a drop of blood to be tested, whereby the blood is analyzed by the electrical contact. The results of the analysis may then displayed on a display such as a liquid crystal display of the sensor-dispensing instrument. It is contemplated that other type of sensors may be used such as optical sensors.

The testing end of the sensor is adapted to be placed into contact with the fluid sample (e.g., a whole blood sample) to be tested. The whole blood sample may be generated by a lancing device such as a lancet. The whole blood sample may be obtained by a lancet that may be separate from the sensor-dispensing instrument or may be integrated within the sensor-dispensing instrument. The lancing device may obtain blood by, e.g., pricking a person's finger.

According to one process, the whole blood sample may be prepared for testing by (a) advancing one of the test sensors in position to receive a whole blood sample; (b) generating a whole blood sample; and (c) bringing the test sensor and the whole blood sample into contact wherein the blood is generally drawn into the sensor by capillary action.

The sensors are typically provided with a capillary channel that extends from the front or testing end of the sensors to biosensing or reagent material disposed in the sensor. When the testing end of the sensor is placed into fluid (e.g., blood that is accumulated on a person's finger after the finger has been pricked), a portion of the fluid is drawn into the capillary channel by capillary action. The fluid then chemically reacts with the reagent material in the sensor so that an electrical signal indicative of the blood glucose level in the blood being tested is supplied and subsequently transmitted to an electrical assembly.

After the testing has been completed, the test sensor may be removed by several methods from the sensor-dispensing instrument. In one embodiment, the sensor-dispensing instrument may include an eject mechanism that ejects the used test sensor from the sensor-dispensing instrument. In such an embodiment, the test sensors is released forcefully. In another embodiment, the test sensors may be ejected by releasing a grip of the test sensors, resulting in the test sensor being discarded by gravity from the sensor-dispensing instrument. In a further embodiment, the test sensor may also be removed manually from the sensor-dispensing instrument.

Figure 15A:
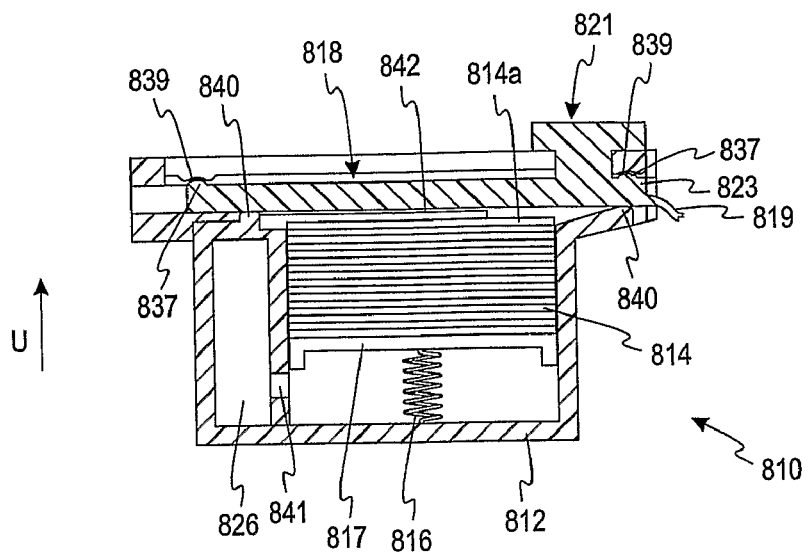
FIG. 15a is a front view of a cartridge in a closed position according to another embodiment of the present invention.

According to a further embodiment, a cartridge 810 of FIGS. 15*a,b* comprises a housing 812, a plurality of test sensors 814, a mechanical mechanism 816, a test sensor support 817, and a sliding pusher lid assembly 818. The cartridge 810 may be adapted to be disposable after all of the plurality of test sensors 814 have been used.

Figure 15B:
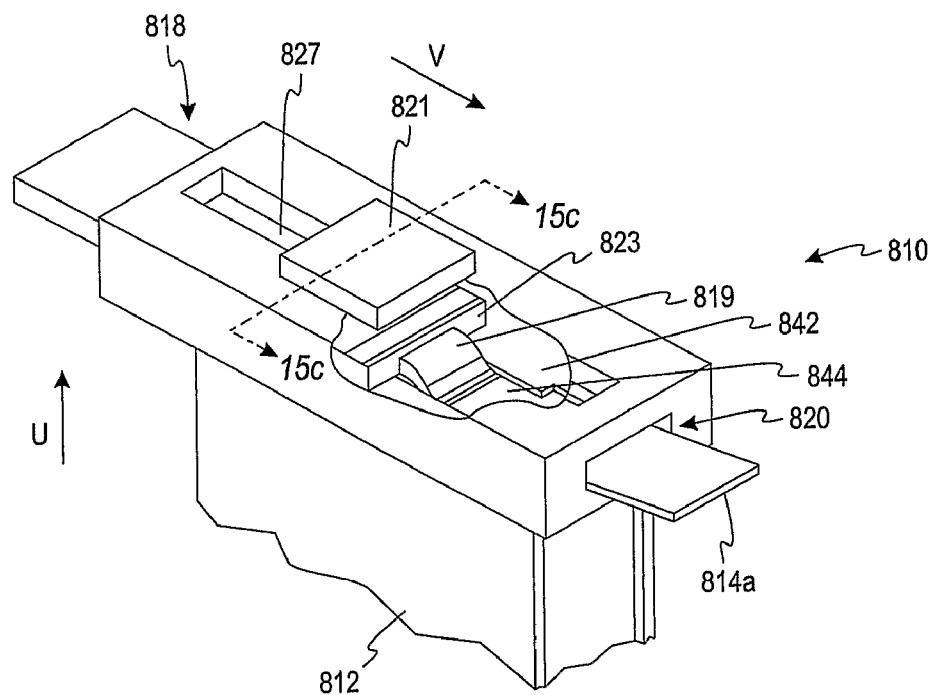
FIG. 15b is a cut-away top perspective view of the cartridge of FIG. 15a in an open position with a test sensor being excised.

Referring to FIG. 15*b*, the housing 812 forms at least one opening 820 therethrough. The opening 820 is sized to allow the plurality of test sensors 814 to move therethrough, one at a time, and eventually exit the cartridge 810. The housing 812 also forms a slit 827 at a top portion thereof (as viewed in FIG. 15*b*) that assists in the movement of the lid assembly 818. The housing 812 may be formed of the same materials and processes as described above in connection with housing 12.

As shown in FIG. 15*a*, the plurality of test sensors 814 is stacked in the housing 812. For clarity, the plurality of test sensors 814, the mechanical mechanism 816, and the test sensor support 817 have not been cross-hatched in FIG. 15*a*. The plurality of test sensors 814 is adapted to assist in testing at least one analyte as discussed above with respect to test sensors 14. To urge the stacked test sensors 814 in a first direction (in the direction of arrow U in FIGS. 15*a*,15*b*), the mechanical mechanism 816 is used according to one embodiment. The mechanical mechanism 816 assists in positioning one of the plurality of test sensors 814 for eventual ejection from the cartridge 810 via the opening 820. The mechanical mechanism 816 may be a spring or the other devices described above in connection with mechanical mechanism 16. The test sensor support 817 assists in evenly feeding the test sensors, which is especially important for test sensors that are thinner and more flexible. To assist in guiding the mechanical mechanism 816 upwardly (in the direction of arrow U in FIGS. 15*a*,15*b*), the housing 812 may be formed with a plurality of prongs or extensions.

The lid assembly 818 of the cartridge 810 is adapted to move between an open position (FIG. 15*b*) and a closed position (FIG. 15*a*). Specifically, the lid assembly 818 slides between the open and the closed positions. The lid assembly 818 extends through the slit 827 that is formed in the housing 812. The slit 827 assists in guiding the lid assembly 818 when sliding between the open and the closed positions. The lid assembly 818 includes a flexible pusher tab 819.

The flexible pusher tab 819 is adapted to contact and push the plurality of test sensors 814 from the housing 812 one at a time and at least partially through the opening 820. The flexible pusher tab 819 extends in a generally downwardly and generally outwardly direction (as viewed with respect to FIGS. 15*a,b*) from the remainder of the lid assembly 818. The plurality of test sensors 814, one at time, is pushed in the direction of arrow V at least partially through the opening 820. The flexible pusher tab 819 is generally located near or at one end of the lid assembly. By having the flexible pusher tab 819 located at or near end, a user can push a test sensor 814 from the opening 820 and clear a seal 840 in one motion in one embodiment. The seal 840 is shown to extend from the housing 812. It is contemplated that this may be formed separately from or integral with the housing 812. In another embodiment, a seal may be located on the lid assembly 818 to seal with the housing 812.

The flexible pusher tabs may be made by polymeric materials. For example, the flexible pusher tabs may be made of polymeric materials such as polycarbonate, ABS, nylon, polyethylene, polystyrene, polypropylene, or combinations thereof. The flexible pusher tabs may be molded with the remainder of the sliding pusher lid assembly.

Figure 21:
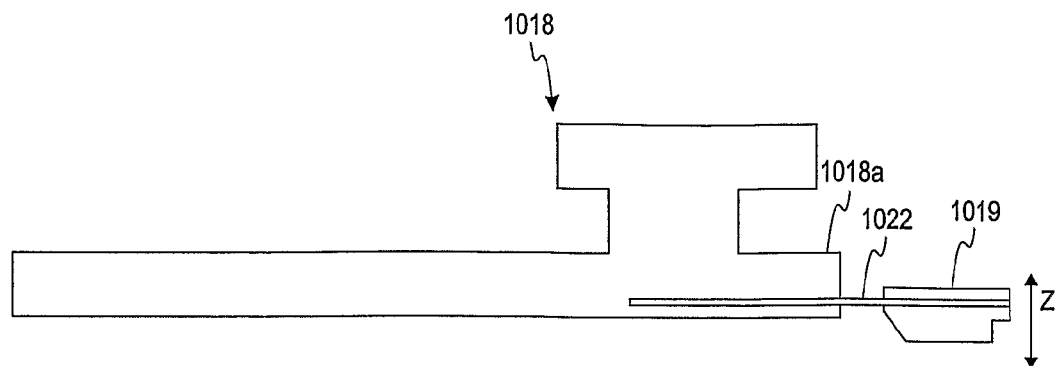
FIG. 21 is a side view of a lid assembly according to another embodiment.

In another embodiment, the flexible pusher tabs may be spring loaded to the remainder of the sliding pusher lid assembly. For example, referring to FIG. 21, a pusher lid assembly 1018 includes a flexible pusher tab 1019 that has flexibility in the general directions shown by arrow Z in FIG. 21. The flexible pusher tab 1019 is connected to a remainder 1018*a* of the pusher lid assembly 1018 via a flexible support 1022. The flexible pusher tab 1019 may be made of, for example, metal or polymeric material. The flexible support 1022 is made of a flexible material. Non-limiting examples of flexible materials that may be used in forming the flexible support include metals or polymeric materials. The flexible support 1022 may be inserted within an opening formed in the remainder 1018*a* of the pusher lid assembly or may be overmolded into the remainder 1018*a* of the pusher lid assembly.

Figure 15C:
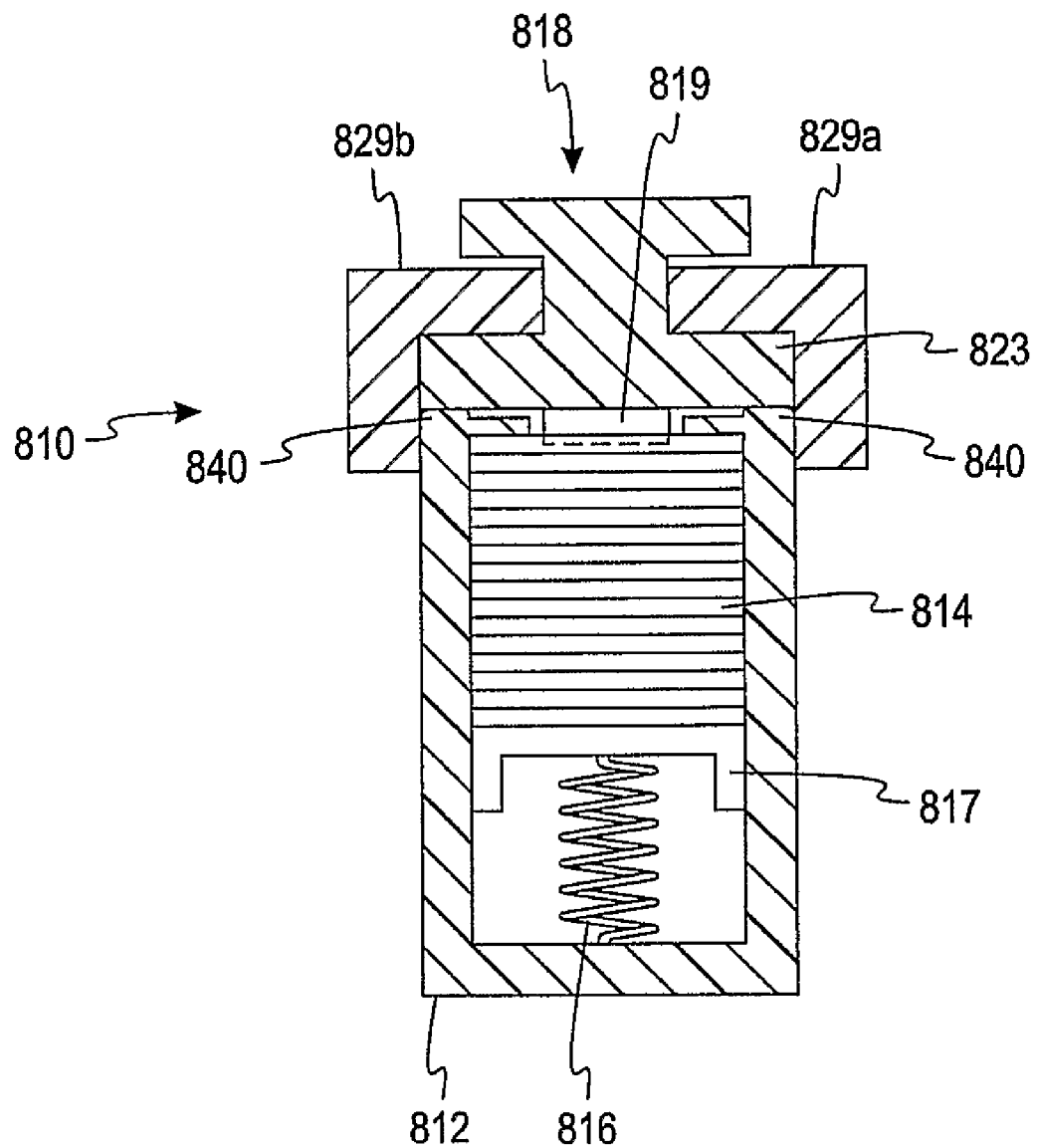
FIG. 15c is a cross-sectional view taken generally along line 15c-15c of FIG. 15b.

According to one process, the lid assembly 818 is manually moved between the open position (FIG. 15*b*) and the closed position (FIG. 15*a*). To assist in manually gripping and sliding the lid assembly 818 between the open and closed positions, the lid assembly 818 includes a pusher grip 821 in one embodiment. The lid assembly 818 of FIGS. 15*a-c* includes the flexible pusher tab 819, pusher grip portion 821 and a pusher base 823. As shown in FIG. 15*c*, a cross-section of the lid assembly 818 is a generally "I" shape. It is contemplated that the cross-section of the lid assembly 818 may be shaped differently than depicted in FIG. 15*c*.

Figure 22:
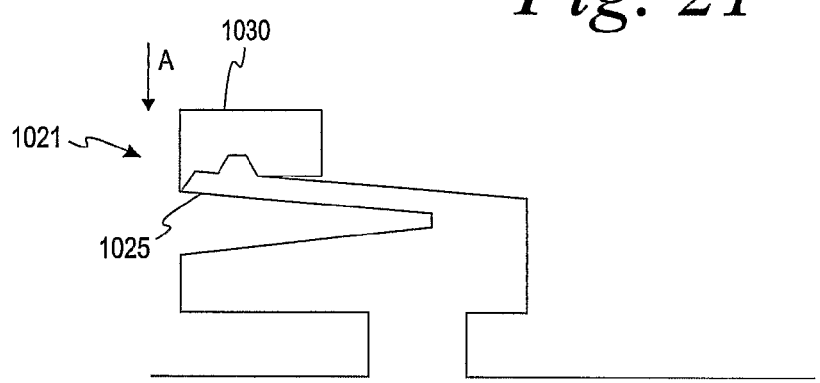
FIG. 22 is a side view of a pusher grip with a locking mechanism according to one embodiment.
Figure 23:
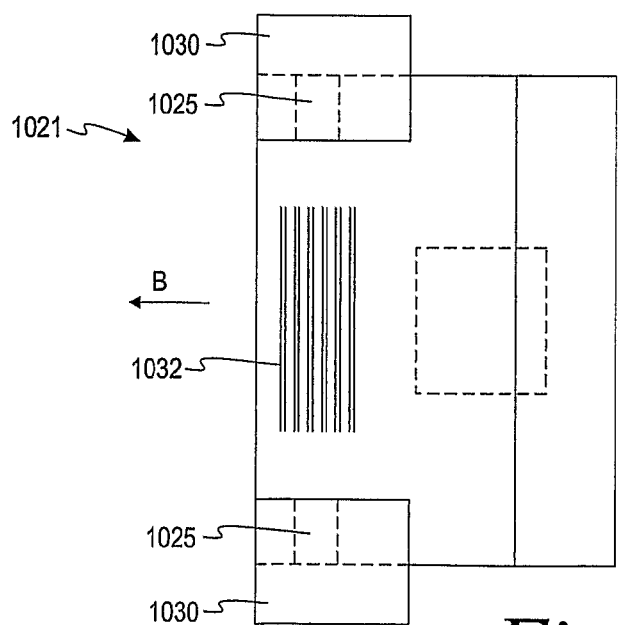
FIG. 23 is a top view of the pusher grip of FIG. 22.

The pusher grip of the lid assembly may also include a locking or latch mechanism to provide added security in maintaining the seal. For example, referring to FIGS. 22 and 23, a pusher grip 1021 includes a flexible tab 1025 and a locking or latch mechanism 1030. As shown in FIG. 22, the flexible tab 1025 is adapted to move in a generally downward direction (direction of arrow A in FIG. 22). Specifically, the flexible tab 1025 is pushed a sufficient distance in the generally downward direction (direction of arrow A) so as to unlock and disengage the lid assembly. After being unlocked, the lid assembly is adapted to move from the closed position to the open position as shown in the general direction of arrow B in FIG. 23. As shown in FIG. 23, the pusher grip 1021 also includes a raised surface 1032 to assist the user in gripping the pusher grip 1021 during movement between the open and the closed positions.

According to another process, the lid assembly 818 may be automatically moved between the open and closed positions by, for example, pressing a button. One example of an automatic process may include the plurality of test sensors 814 being removed entirely using a motorized mechanism.

To assist in removing the plurality of test sensors 814 one at a time, the cartridge may include a reference surface 842 that is adapted to contact and provide a surface for the plurality of test sensors 814 to push against. The reference surface 842 provides a stop that holds the plurality of test sensors 814 in position for removal from the cartridge 810. The reference surface 842 forms a slit 844 therein that gives access to the entire length of the topmost test sensor (as viewed in FIG. 15*b*) of the stacked test sensors. Another example of a reference surface (reference surface 843) is depicted in FIG. 16*b*. The flexible pusher tab 819 extends through the slit 844 so as to contact and push the uppermost test sensor (as viewed in FIG. 15*b*). The slit 844 at least one end thereof has a sufficient width to provide an exit for the uppermost test sensor to push at least partially through the opening 820.

The length that the flexible pusher tab 819 extends down into the cartridge is typically greater than the thickness of the reference surface 842 plus the clearance between the bottom of the lid assembly 818 and the top of the reference surface, but not greater than the thickness of the reference surface 842 plus the thickness of one of the plurality of test sensors 814. The position of the flexible pusher tab may be referenced against the reference surface so that mechanical tolerance requirements are minimized. By maintaining these dimensions, the lid assembly 818 and, more specifically, the flexible pusher tab 819 will move only one test sensor at a time.

After the test sensor 814*a* has been pushed from the cartridge 810, the next test sensor is loaded into position via the mechanical mechanism 816 (e.g., a spring). When the lid assembly 818 is in the closed position (FIG. 15*a*), the lid assembly 818 desirably seals the opening 820. Although it is desirable to seal the opening 820 to prevent or inhibit contamination by foreign matter (e.g., dirt and liquid), it is not necessary to seal 820 in an air-tight or humidity-tight seal because of a seal 840. For example, referring to FIGS. 15*a,c*, the cartridge 810 includes the seal 840 to assist in preventing or inhibiting moisture from entering the housing 812. In the cartridge 810, the seal 840 is located generally around the periphery of the opening. The seal 840 assists in maintaining a desirable seal with the lid assembly 818. It is desirable for the seal 840 to extend completely around the lid assembly 818 when the lid assembly is in a closed position. Because the pusher tab 819 is flexible, it clears the seal 840 when the lid assembly 818 is moved between the open and closed positions. The location of the pusher tab 819 relative to the pusher base 823 assists in pushing the test sensor farther through the opening 820 cleared in one motion. It is also contemplated that a sealing mechanism may be located on the lid assembly itself.

To assist in sliding the lid assembly 818 between the open position and the closed position, at least one retainer tab may be used. For example, in FIG. 15*c*, retainer tabs 829*a,b* restrict the lid assembly to sliding between the closed position and the open position. To maintain positive pressure, the retainer tabs 829*a,b* may be made of a flexible material. The retainer tabs 829*a,b* function in a similar manner as described above with retainers tabs 154*a,b* of FIG. 4.

To increase the downward sealing force on the lid assembly 818 in the sealed or closed position and to assist in indicating to the user that the lid assembly is in a closed position, the cartridge 810 may include at least one détente 839 as shown in FIG. 15*a*. Specifically, the plurality of détentes 839 in FIG. 15*a* works with corresponding bumps 837 formed in the lid assembly 818.

To assist in protecting the reagent(s) in the test sensors 814, desirable packaging material and/or desiccant material may be used. The cartridge 810 is typically packaged in material that prevents or inhibits air from entering into an interior of the housing 812 that contains the test sensors 814 as discussed above in connection with cartridge 10. Additionally, as discussed above in connection with cartridge 10, desiccant material 826 (FIG. 15*a*) may be added to the cartridge 810. To assist in having the desiccant material 826 contact the test sensors, an opening 841 may be formed in an interior structure of the housing 812.

It is contemplated that the flexible pusher tabs may be of different designs so as to assist in pushing the test sensors 814. For example, in FIGS. 16*a,b*, a flexible pusher tab 852 forms a notch 854 at one end thereof. Each of the plurality of test sensors 856 forms a notch 858 therein. During movement of the flexible pusher tab 852, the notch 854 engages at least a portion of the notch 858 and assists in pushing the plurality of test sensors 856 one at a time. To assist in preventing or inhibiting more than one test sensor from being pushed by the flexible pusher tab 852, the thickness T8 of the notch 854 is desirably less than the thickness T6 of the test sensor 856. In a case of a test sensor without a notch (e.g., an optical sensor) or in a case where it is desirable to push an electrochemical sensor out the notched (electrode) end first, then the thickness T8 of the notch 854 is then desirably less than the thickness T7 of the test sensor 856.

The test sensor 856 should be of sufficient rigidity such that when the flexible pusher tab 852 contacts the test sensors, the test sensors 856 do not bend and jam. The rigidity or stiffness of the test sensors is determined by factors such as the material used in forming the test sensors and the thickness of the test sensors (see, e.g., thicknesses T6 and T7 of the test sensor 856*a* of FIG. 16*a*). If the thickness of the test sensors varies, it is desirable to have the more rigid end (usually the thicker end) of the test sensor to enter through the opening first.

The amount of force that the flexible pusher tab 852 provides must be sufficient to push one of the plurality of test sensors at least partially through the opening, while at the same time the amount of force should not result in (a) the test sensors significantly bending or (b) multiple test sensors being grabbed. If the test sensor bends or multiple test sensors are grabbed, the likelihood of a jam occurring is increased.

As the flexible pusher tab 852 is moved in the direction of arrow W (FIG. 16*a*), a reference surface 843 provides a surface in which the test sensors 856 push against as described above in conjunction with the reference surface 842 of FIGS. 15*a*, 15*b*. A side reference surface 846 also assists in guiding the test sensors through an opening 849 in the cartridge. A distance D2 of the opening 849 should be greater than the thickness T7 of the test sensors 856. The distance D2 of the opening 849, however, is desirably not greater than twice the thickness T7 so as to prevent or inhibit multiple test sensors from exiting the opening 849 at the same time. The side reference surface 846 also assists in preventing or inhibiting multiple test sensors from exiting at the same time by being positioned such that the formed opening only allows one test sensor 856 to be pushed out at a time. It is contemplated that the references surfaces 843 and 846 may be of different lengths, shapes and may also be discontinuous. A side reference surface 847 assists in guiding the test sensors 856 into the proper position for pick-up by the pusher tab 852.

Figure 16A:
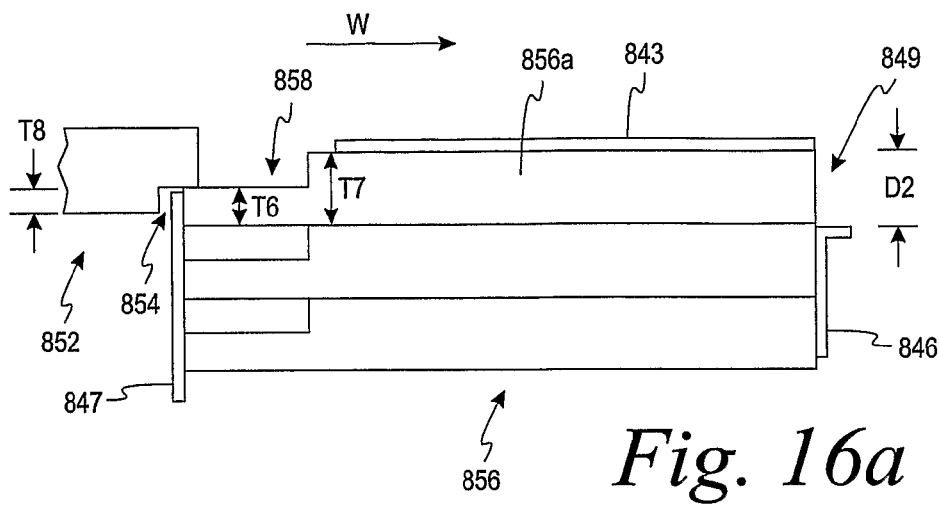
FIG. 16a is an enlarged front view of a partial cartridge with a flexible pusher tab according to another embodiment of the present invention.
Figure 16B:
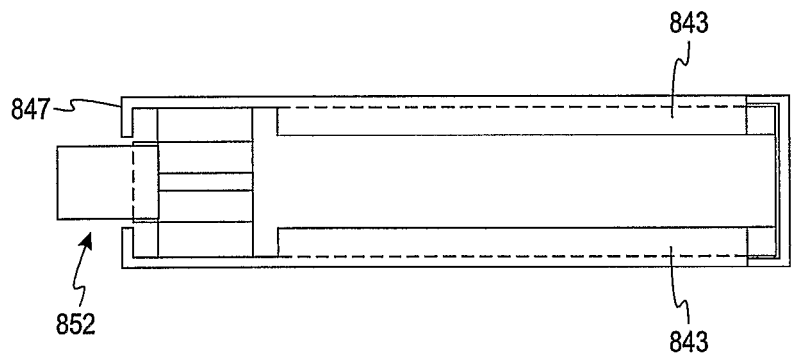
Figure 16C:
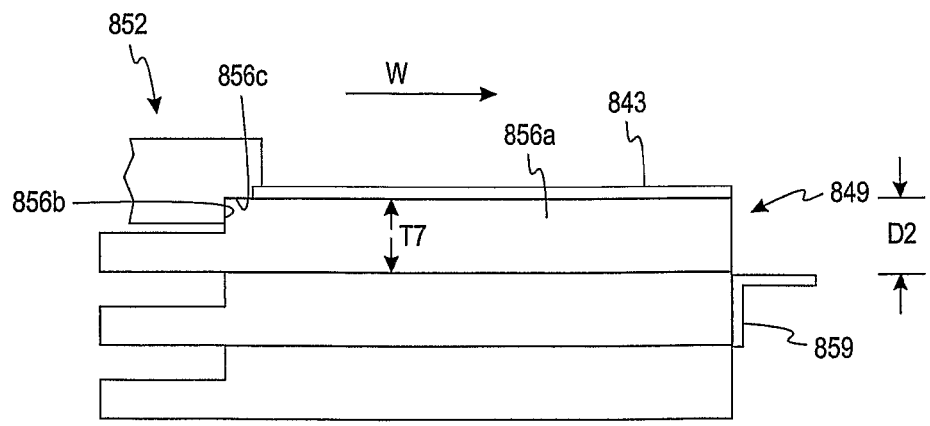
FIG. 16c is an enlarged front view of a partial cartridge with a flexible pusher tab according to a further embodiment of the present invention.

The flexible pusher tab 852 may engage a different surface of the test sensor than depicted in FIGS. 16*a*, 16*b*. For example, in FIG. 16*c*, the flexible pusher tab 852 is depicted as engaging surfaces 856*b*, 856*c*. Thus, in this embodiment, the flexible pusher tab 852 moves one of the plurality of test sensors 856 by pushing on the thicker portion thereof. The flexible pusher tab 852 moves the plurality of test sensors 856, one at a time, in the direction of arrow W and through the opening 849. Side reference surface 859 functions in a similar manner as the reference surface 846 discussed above in connection with FIGS. 16*a*, 16*b*. It is contemplated that the references surfaces 843 and 859 may be of different lengths, shapes and may also be discontinuous.

Figure 17A:
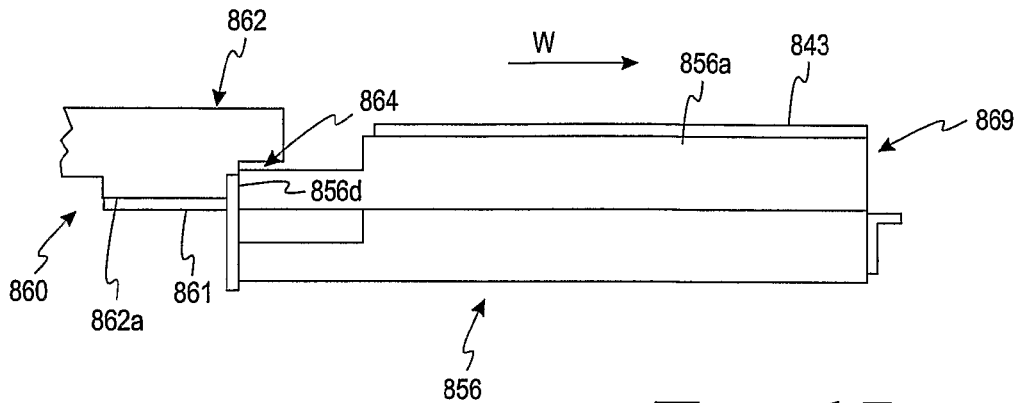
FIGS. 17a-c are enlarged front views of a partial cartridge with a flexible pusher tab using a guiding mechanism according to one embodiment of the present invention.

According to another embodiment, a cartridge may also further include a guiding mechanism to assist in positioning the flexible pusher tab assembly and facilitate removing the plurality of test sensors one at a time. The flexible pusher tab assembly 860 of FIGS. 17*a-c* includes a flexible pusher tab 862 and a guiding mechanism. One example of a guiding mechanism is a cam mechanism. A cartridge includes a cam mechanism that includes a reference surface 861 and a corresponding surface 862*a* on the pusher tab 862. Thus, the cam mechanism works in conjunction with the pusher tab 862. The flexible pusher tab 862 forms a notch 864 therein. As shown in FIG. 17*a*, the notch 864 initially engages a generally vertical surface 856*d* of the test sensor 856*a*. As the test sensor 856*a* of FIG. 17*a* is moved in the direction of arrow W, the notch 864 continues to engage the generally vertical surface 856*d* as shown in FIG. 17*b*.

Figure 17B:
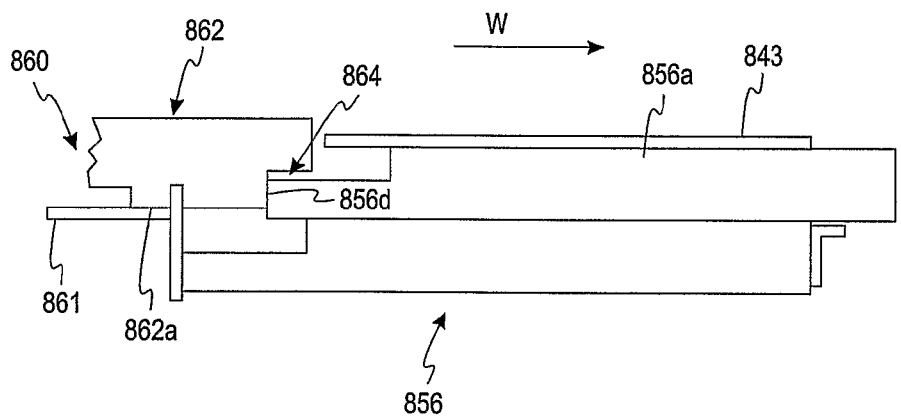
Figure 17C:
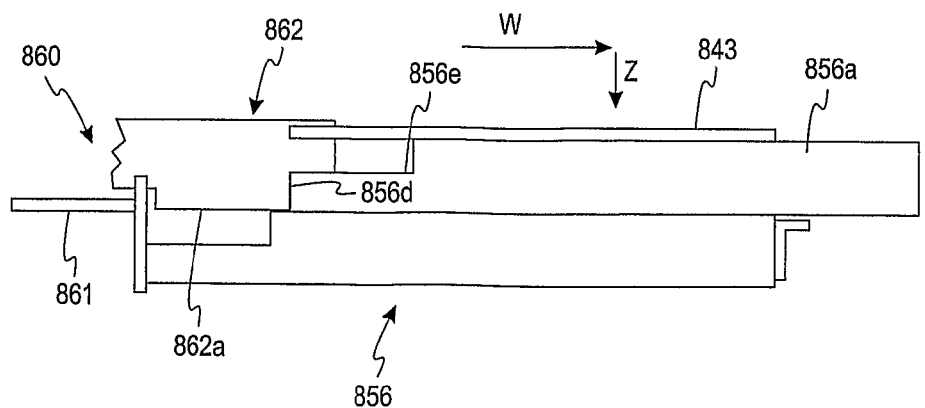

As shown in FIG. 17*c*, the reference surface 861 forces the flexible pusher tab 862 to align in such a way so as to move in a generally downward direction (direction of arrow Z in FIG. 17*c*) and then back in the direction of arrow W. At this point, the notch 864 engages the generally vertical surface 856*d* and the generally horizontal surface 856*e*. Thus, by using the cam mechanism, the flexible pusher tab 862 contacts and pushes a greater amount of surface area (compare FIG. 17*c* with FIGS. 17*a,b*), which reduces the likelihood that more than one of the plurality of test sensors 856 will be contacted. The flexible pusher tab 862 pushes the test sensors 856, one at a time, through an opening 869.

The control of the exact position of the pusher tab relative to the test sensors may be implemented by various combinations of referenced surfaces on the pusher tab and the cartridge. For example, referring to FIGS. 18*a-c*, a pusher tab assembly 870 includes a flexible pusher tab 872 and a guiding mechanism. The movement of the flexible pusher tab 872 is controlled by a guiding mechanism that includes a track 877 in the cartridge and a corresponding pin or reference surface 876 on the pusher tab 872. The track 877 on the cartridge is generally aligned with the reference surface 843 and by engaging the pin 876 on the pusher tab maintains the vertical position of the pusher tab 872 relative to the test sensors as long as the flexible pusher tab is long enough and has sufficient spring force to engage the alignment cam. By the flexible pusher tab having such characteristics, then the tolerances of the entire assembly may be relaxed without jeopardizing the reliability of the pusher tab excising one and only one sensor per stroke.

Figure 18A:
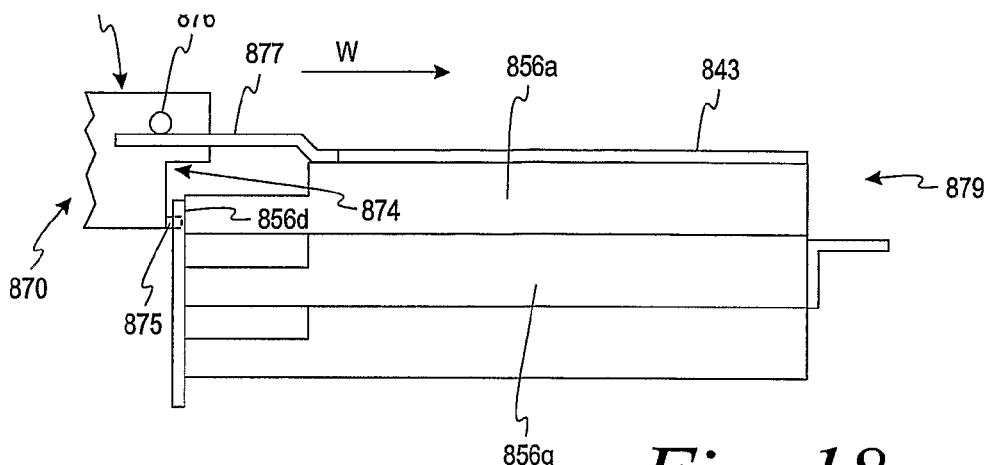
FIGS. 18a-c are enlarged front views of a partial cartridge with a flexible pusher tab using a guiding mechanism according to another embodiment of the present invention.
Figure 18B:
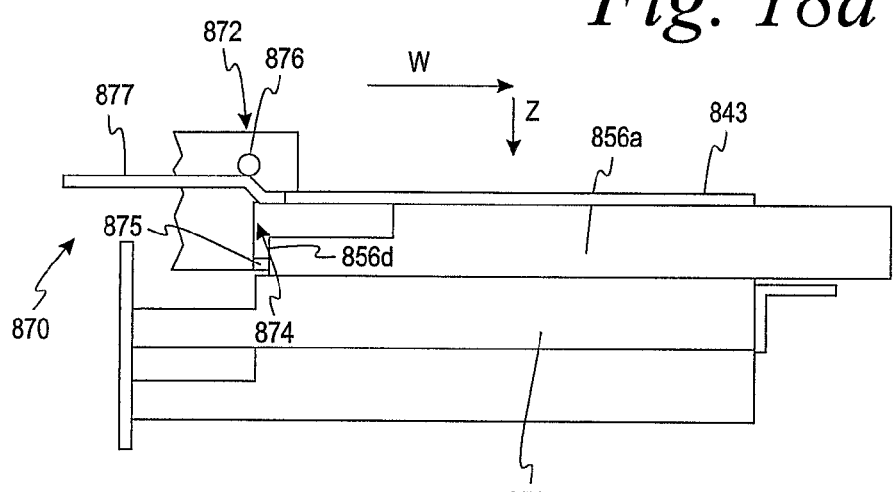
Figure 18C:
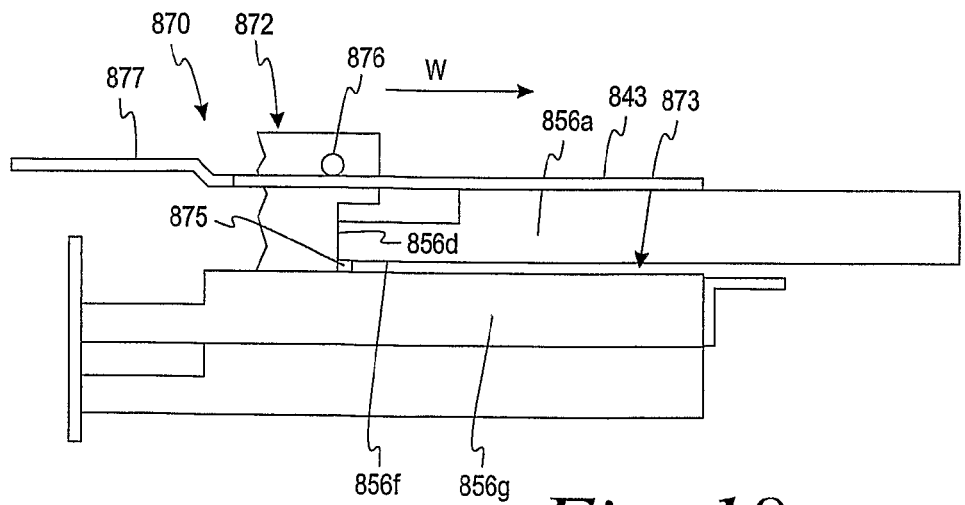

As shown in FIGS. 18*a-c*, the flexible pusher tab 872 also contacts different surfaces of the test sensors during movement of the test sensors from the cartridge than depicted in, for example, FIGS. 17*a-c*. For example, the flexible pusher tab 872 of FIGS. 18*a*-*c* is shown contacting the test sensor 856*a*. The flexible pusher tab 872 forms a notch or cavity 874 therein and also includes a surface-contacting extension 875. As shown in FIGS. 18*a*,*b*, the surface-contacting extension 875 contacts the generally vertical surface 856*d* of test sensor 856*a*. As the flexible pusher tab 872 is moved in the direction of arrow W, the surface-contacting extension 875 continues to contact the surface 856*d* as shown in FIG. 18*a*. The guiding mechanism formed by the track 877 and the corresponding pin 876 continues to move the flexible pusher tab 872 in the direction of arrow W as well as in a downwardly direction (in the direction of arrow Z in FIG. 18*b*).

When the flexible pusher tab 872 is moved in a downward direction, the surface-contacting extension 875 extends below and contacts a bottom surface 856*f* of the test sensor 856*a*. A space 873 is formed between test sensors 856*a*,*g* when the surface-contacting extension 875 extends between these two test sensors 856*a*,*g*. During the remaining pushing of the test sensor 856*a*, the surface-contacting extension 875 continues to engage the bottom surface 856*f* such that the test sensor 856*a* is not abutting any of the remaining test sensors 856. At the same time, the notch 874 contacts the generally vertical surface 856*d*. The notch 874 acts to more securely capture the test sensor during the excision process. By having the flexible pusher tab 872 contact the bottom surface 856*f* of the test sensor 856*a*, it assists in preventing or inhibiting more than one test sensor from exiting an opening 879.

Figure 19A:
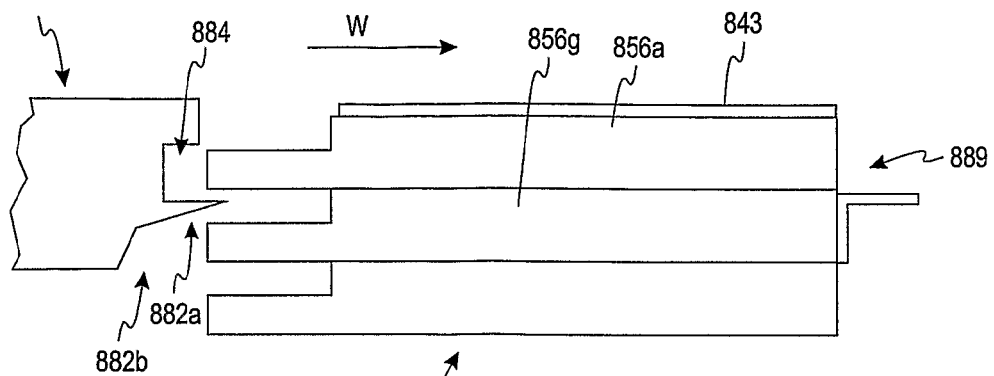
FIGS. 19a-c are enlarged front views of a partial cartridge with a flexible pusher tab according to yet another embodiment.
Figure 19B:
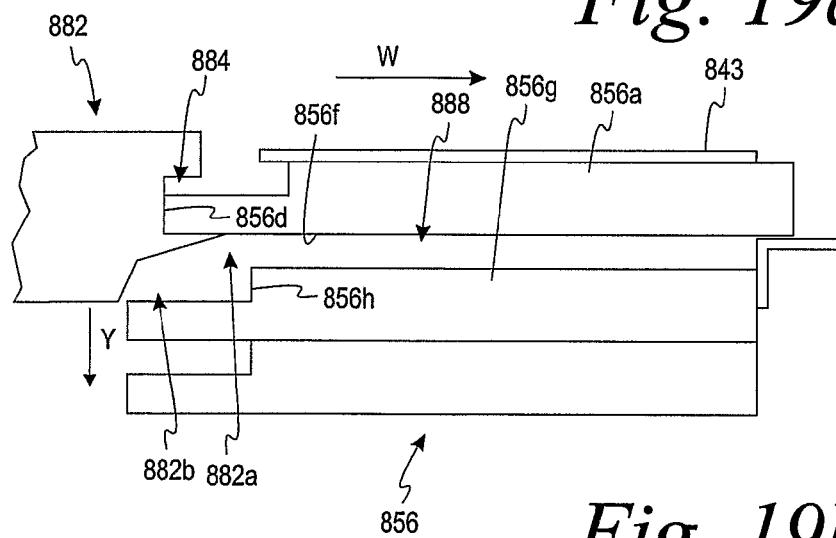
Figure 19C:
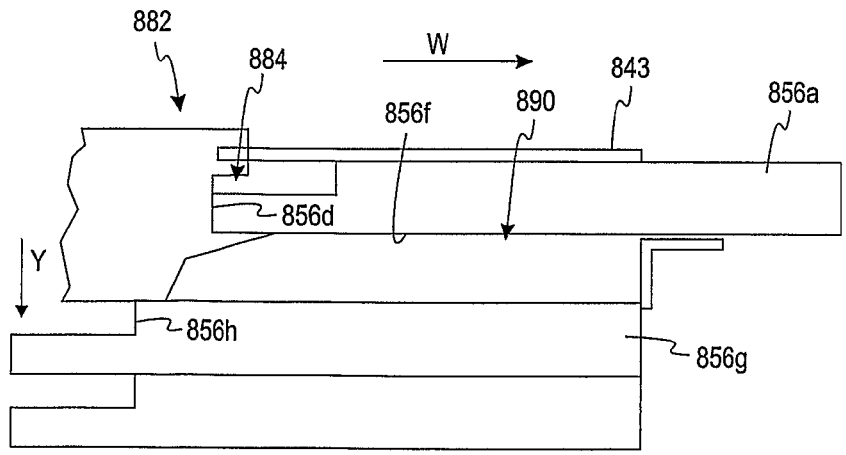

According to a further embodiment, a flexible pusher tab 882 of FIGS. 19*a*-*c* is shown contacting one of the plurality of test sensors 856. The flexible pusher tab 882 forms a notch 884 therein and also includes a bottom surface-contacting extension 882*a*. As shown in FIG. 19*b*, the surface-contacting extension 882*a* contacts the bottom surface 856*f* of the test sensor 856*a*. As the flexible pusher tab 882 is moved by pushing on the surface 856*a* in the direction of arrow W, the surface-contacting extension 882*a* continues to contact the bottom surface 856*f* as shown in FIG. 19*b*.

As the surface-engaging portion 882*a* is contacting the test sensor 856*a*, a surface-engaging portion 882*b* pushes the remainder of the plurality of test sensors 856 in a generally downward direction (the direction of arrow Y in FIG. 19*b*). A space 888 is initially formed between the test sensors 856*a*,*g* when the surface-contacting extension 882*a* extends between these two test sensors 856*a*,*g*. During the remaining pushing of the test sensor 856*a* in the direction of arrow W, the surface-contacting extension 882*a* continues to engage the bottom surface 856*f* such that the test sensor 856*a* is not abutting any of the remaining test sensors 856. As shown in FIGS. 19*b*, 19*c*, the space 888 is increased in size as the surface-engaging portion 882*b* contacts a generally vertical surface 856*h* of the test sensor 856*g*, which results in a space 890 being formed. The notch 884 contacts the generally vertical surface 856*d* throughout the movement of the flexible pusher tab 882. By having the flexible pusher tab 882 contact the bottom surface 856*f* of the test sensor 856*a*, it assists in preventing or inhibiting more than one test sensor from exiting opening 889 or "dropping" the top sensor during a forward stroke.

Figure 20A:
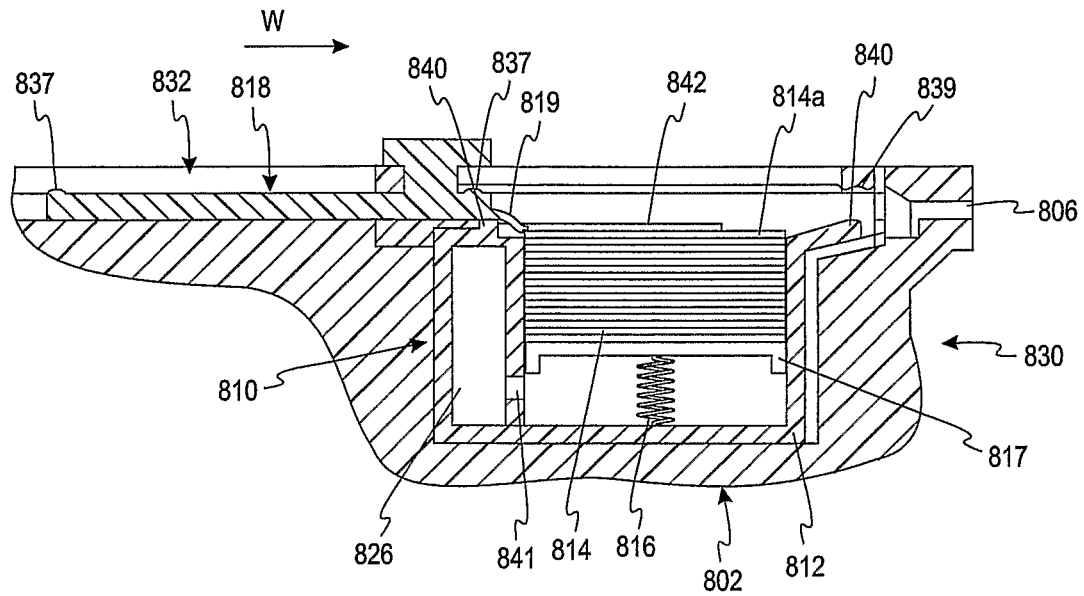
FIGS. 20a-c are partial front views of a sensor-dispensing instrument using the cartridge of FIG. 15a according to one another embodiment.
Figure 20B:
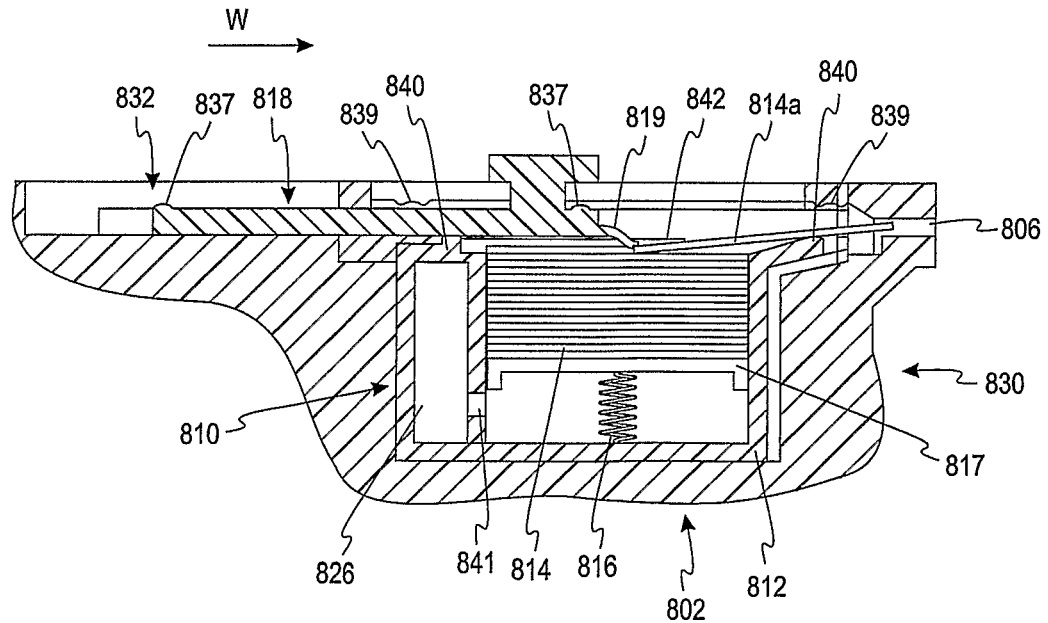
Figure 20C:
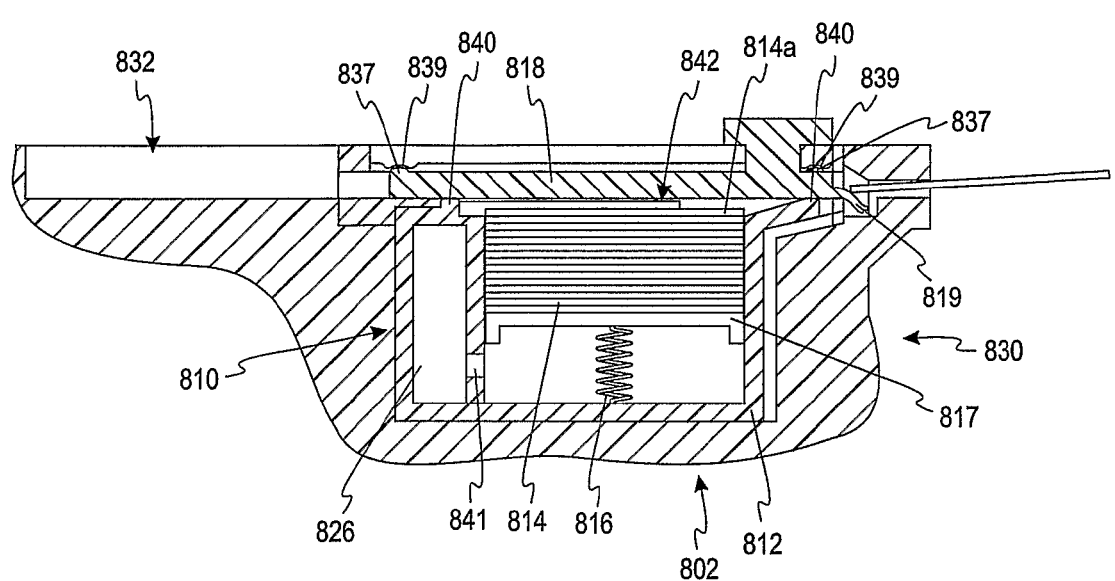

Referring to FIGS. 20*a*-*c*, a sensor-dispensing instrument 830 is depicted according to one embodiment. The sensor-dispensing instrument is used to determine concentrations of analytes. Analytes that may be measured using the present invention include glucose, lipid profiles (e.g., cholesterol, triglycerides, LDL and HDL), microalbumin, hemoglobin $A_{1C}$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, other body fluids like ISF (interstitial fluid) and urine, or non-body fluids.

The sensor-dispensing instrument 830 comprises the cartridge 810 (described above in connection with FIGS. 15*a*-*c*) and an instrument housing 802. As shown in FIGS. 20*a*-*c*, the instrument housing 802 is adapted to receive the cartridge 810 of FIGS. 15*a*-*c*. It is desirable for the cartridge 810 to be removed from and loaded into the instrument housing 802 of the sensor-dispensing instrument 830 in a simple and easy manner.

It is contemplated that other cartridges may be used in a sensor-dispensing instrument such as those cartridges having a sliding pusher lid assembly with various flexible pusher tabs 852, 866, 870 and 880 described above in connection with FIGS. 16-19. Depending on the selected cartridge, the interior of the instrument housing may be redesigned to correspond to the selected cartridge. The instrument housing 802 also forms a dispensing outlet 806, which is sized to dispense the test sensors 814 or, alternatively, test sensor 856 one at a time. The instrument housing 802 also forms a cavity 832 that receives at least a portion of the sliding lid assembly 818 when the sliding lid assembly 818 is in the open position. The cavity 832 also assists in guiding the sliding pusher assembly between the first position and the second position.

Referring to FIG. 20*a*, the instrument 830 is shown with the sliding lid assembly 818 in an open position. As the sliding lid assembly 818 is moved in the direction of arrow W, the flexible tab pusher 819 contacts and pushes the test sensor 814*a* in the same direction as shown in FIG. 20*b*. The test sensor 814*a* is pushed at least partially into the dispensing outlet 806 and then is later removed. The sliding lid assembly 818 is then placed in the closed position as shown in FIG. 20*c*. In the closed position, the sliding lid assembly 818 covers the top of the cartridge 810. Additionally, the sliding lid assembly 818 works in conjunction with the seal 840 to prevent or inhibit the moisture from entering into the interior of the cartridge 810. By being flexible, the flexible tab pusher 819 may extend at least slightly into the dispensing outlet 806, which allows the seal 840 to form a seal with the remainder of the sliding lid assembly 818, thus preventing or inhibiting the moisture from entering into the interior of the cartridge 810.

According to other embodiments, the sliding lid assembly may be a part of the sensor-dispensing instrument as opposed to the disposable cartridge. In such embodiments, the lid retracts slightly farther in the direction of arrow W in FIGS. 16-19 to allow the pusher tab and the remainder of the lid assembly to clear the opening for removing a used cartridge and replacing it with a fresh cartridge. The instrument may make electrical contact with the cartridge to read calibration information specific to the cartridge. In addition, contact switches in the instrument or inside the cartridge may be used to allow the meter electronics to sense the position of the lid. This would allow the electronics to prompt the user to make or complete certain actions required for testing. For example, the instrument may give an audible signal (e.g., a beep) if the lid is not moved entirely to the closed position. A humidity sensor in the cartridge could be used to detect exposure to excessive moisture.

Although ideally the cartridges of the present invention fit in an instrument and dispense sensors into the proper position for measurement, the cartridge design may function as a stand-alone test sensor container (i.e., a bottle that automatically dispenses a strip for manual loading into an instrument).

Alternate Embodiment A

A cartridge adapted to be used with a sensor-dispensing instrument, the cartridge comprising:
a housing forming at least one opening therethrough;
a plurality of test sensors being stacked in the housing, the plurality of test sensors being adapted to assist in testing at least one analyte;
a mechanical mechanism being adapted to urge the plurality of test sensors in a first direction, one of the plurality of test sensors being positioned for extraction from the cartridge; and
a pusher assembly being adapted to push one of the plurality of test sensors from the cartridge, the pusher assembly including a ferromagnetic material or a magnet.

Alternate Embodiment B

The cartridge of Alternate Embodiment A wherein the mechanical mechanism is a spring.

Alternate Embodiment C

The cartridge of Alternate Embodiment A wherein the housing forms exactly one opening.

Alternate Embodiment D

The cartridge of Alternate Embodiment A wherein the analyte is glucose.

Alternate Embodiment E

The cartridge of Alternate Embodiment A further including desiccant.

Alternate Embodiment F

The cartridge of Alternate Embodiment A wherein the plurality of sensors is electrochemical sensors.

Alternate Embodiment G

The cartridge of Alternate Embodiment A wherein the plurality of sensors is optical sensors.

Alternate Embodiment H

The cartridge of Alternate Embodiment A wherein the pusher assembly includes a magnet.

Alternate Embodiment I

The cartridge of Alternate Embodiment A wherein the pusher assembly includes a ferromagnetic material.

Alternate Embodiment J

The cartridge of Alternate Embodiment I wherein the ferromagnetic material is iron, nickel, cobalt or combinations thereof.

Alternate Embodiment K

The cartridge of Alternate Embodiment A further including a sealing port, the sealing port surrounding the at least one opening.

Alternate Embodiment L

The cartridge of Alternate Embodiment A further including a lid that is moveable between a closed position and an open position such that the lid seals the at least one opening in the closed position.

Alternate Embodiment M

The cartridge of Alternate Embodiment L wherein the lid is adapted to slide between an open position and a closed position.

Alternate Embodiment N

The cartridge of Alternate Embodiment M further including at least one retainer tab to assist in maintaining pressure on the lid in forming a seal.

Alternate Embodiment O

A sensor-dispensing instrument comprising:
a cartridge including a cartridge housing, a plurality of test sensors, a mechanical mechanism and a pusher assembly, the cartridge housing forming at least one cartridge opening therethrough, the plurality of test sensors being stacked in the cartridge housing, the plurality of test sensors being adapted to assist in testing at least one analyte, the mechanical mechanism being adapted to urge the plurality of test sensors in a first direction, one of the plurality of test sensors being positioned for extraction from the cartridge, the pusher assembly being adapted to push one of the plurality of test sensors from the cartridge, the pusher assembly including a ferromagnetic material or a magnet;
an instrument housing forming a dispensing outlet and being adapted to receive the cartridge;
a lid being moveable between a closed position and an open position such that the lid seals at least one of the dispensing outlet and the cartridge opening in the closed position; and
a slider comprising a ferromagnetic material or a magnet, the slider being adapted to be magnetically coupled to the pusher assembly of the cartridge, the slider being adapted to slide from a first position to a second position,
wherein during the movement of the slider from the first position to the second position, the pusher assembly contacts one of the plurality of test sensors and pushes it at least partially through the dispensing opening,
wherein at least the pusher assembly or the slider comprises a magnet.

Alternate Embodiment P

The sensor-dispensing instrument of Alternate Embodiment O wherein the mechanical mechanism is a spring.

Alternate Embodiment Q

The sensor-dispensing instrument of Alternate Embodiment O wherein the analyte is glucose.

Alternate Embodiment R

The sensor-dispensing instrument of Alternate Embodiment O wherein the cartridge further including desiccant.

Alternate Embodiment S

The sensor-dispensing instrument of Alternate Embodiment O wherein the plurality of sensors is electrochemical sensors.

Alternate Embodiment T

The sensor-dispensing instrument of Alternate Embodiment O wherein the plurality of sensors is optical sensors.

Alternate Embodiment U

The sensor-dispensing instrument of Alternate Embodiment O wherein the pusher assembly and the slider include a magnet.

Alternate Embodiment V

The sensor-dispensing instrument of Alternate Embodiment O wherein the pusher assembly comprises a ferromagnetic material and the slider comprises a magnet.

Alternate Embodiment W

The sensor-dispensing instrument of Alternate Embodiment O wherein the pusher assembly comprises a magnet and the slider comprises a ferromagnetic material.

Alternate Embodiment X

The sensor-dispensing instrument of Alternate Embodiment O wherein the magnet is an electromagnet.

Alternate Embodiment Y

The sensor-dispensing instrument of Alternate Embodiment O wherein the lid is moved between an open position and a closed position via a hinge.

Alternate Embodiment Z

The sensor-dispensing instrument of Alternate Embodiment Y wherein during the movement of the slider from the first position to the second position, the slider contacts the lid and moves the lid from a closed position to an open position.

Alternate Embodiment A1

The sensor-dispensing instrument of Alternate Embodiment O wherein the lid is generally circular.

Alternate Embodiment B1

The sensor-dispensing instrument of Alternate Embodiment O wherein the lid is a generally rectangular shape.

Alternate Embodiment C1

The sensor-dispensing instrument of Alternate Embodiment O wherein the lid is adapted to slide between an open position and a closed position.

Alternate Embodiment D1

The sensor-dispensing instrument of Alternate Embodiment C1 further comprising at least one retainer tab to assist in maintaining pressure on the lid in forming a seal.

Alternate Embodiment E1

The sensor-dispensing instrument of Alternate Embodiment D1 wherein the at least one retainer tab includes at least one detent.

Alternate Embodiment F1

The sensor-dispensing instrument of Alternate Embodiment C1 wherein the lid is adapted to manually slide between the open position and the closed position.

Alternate Embodiment G1

The sensor-dispensing instrument of Alternate Embodiment C1 wherein the lid is adapted to automatically slide between the open position and the closed position.

Alternate Embodiment H1

The sensor-dispensing instrument of Alternate Embodiment O further comprising a seal located generally around the periphery of the dispensing opening.

Alternate Embodiment I1

The sensor-dispensing instrument of Alternate Embodiment O wherein the lid includes a first end and a second end, the lid being moveable between a closed position and an open position via a hinge located near the first end such that the lid seals the opening in the closed position, the lid including a projection located near the second end, the projection extending generally downwardly into an interior of the cartridge.

Alternate Embodiment J1

The sensor-dispensing instrument of Alternate Embodiment I1 wherein the projection forms at least one detent to assist in further sealing the cartridge.

Alternate Embodiment K1

The sensor-dispensing instrument of Alternate Embodiment O wherein the lid seals the dispensing outlet in the closed position.

Alternate Embodiment L1

The sensor-dispensing instrument of Alternate Embodiment O wherein the lid seals the cartridge opening in the closed position.

Alternate Embodiment M1

A lid mechanism adapted to be used in a cartridge or a sensor-dispensing instrument that includes a plurality of test sensors to assist in determining the concentration of at least one analyte, the lid mechanism comprising:
a lid being adapted to slide between a closed position and an open position such that the lid seals an opening in the closed position; and
a plurality of retainer tabs to assist in maintaining pressure on the lid in forming a seal.

Alternate Embodiment N1

The lid mechanism of Alternate Embodiment M1 wherein the lid is a generally rectangular shape.

Alternate Embodiment O1

The lid mechanism of Alternate Embodiment M1 wherein at least one of the plurality of retainer tabs includes at least one detent.

Alternate Embodiment P1

The lid mechanism of Alternate Embodiment O1 wherein the periphery of the lid forms at least one recess that corresponds with the at least one detent.

Alternate Embodiment Q1

The lid mechanism of Alternate Embodiment M1 wherein the plurality of retainer tabs is generally flexible.

Alternate Embodiment R1

The lid mechanism of Alternate Embodiment M1 wherein the plurality of retainer tabs is injected molded in forming the cartridge or the sensor-dispensing instrument.

Alternate Embodiment S1

A cartridge comprising:
a housing forming at least one opening therethrough;
a plurality of test sensors being stacked in the housing, the plurality of test sensors being adapted to assist in testing at least one analyte;
a mechanical mechanism being adapted to urge the plurality of test sensors in a first direction, one of the plurality of test sensors being positioned for extraction from the cartridge;
a test-sensor extractor being adapted to move between a first position and a second position; and
a lid being mechanically linked to the test-sensor extractor, the lid being moveable between a closed position and an open position such that the lid seals the opening in the closed position,
wherein during the movement of the lid from the closed position to the open position, the test-sensor extractor moves from the first position to the second position and extracts one of the plurality of test sensors at least partially through the opening.

Alternate Embodiment T1

The cartridge of Alternate Embodiment S1 wherein the lid is manually moveable between the open position and the closed position.

Alternate Embodiment U1

The cartridge of Alternate Embodiment S1 further including a ramp positioned to assist in extracting one of the plurality of test sensors at least partially through the opening.

Alternate Embodiment V1

The cartridge of Alternate Embodiment S1 wherein the plurality of test sensors is stacked on a slant.

Alternate Embodiment W1

The cartridge of Alternate Embodiment S1 wherein the lid further includes a seal.

Alternate Embodiment X1

The cartridge of Alternate Embodiment S1 wherein the lid forms at least one notch.

Alternate Embodiment Y1

The cartridge of Alternate Embodiment S1 wherein the lid is mechanically linked via a flexible linkage.

Alternate Embodiment Z1

The cartridge of Alternate Embodiment Y1 wherein the lid is mechanically linked via a linkage that is hinged at the lid.

Alternate Embodiment A2

The cartridge of Alternate Embodiment Y1 wherein the lid is mechanically linked via a linkage that is hinged at the test-sensor extractor.

Alternate Embodiment B2

The cartridge of Alternate Embodiment S1 wherein the test-sensor extractor is generally parallel with the opening.

Alternate Embodiment C2

The cartridge of Alternate Embodiment S1 wherein the mechanical mechanism is a spring.

Alternate Embodiment D2

The cartridge of Alternate Embodiment S1 wherein the housing forms exactly one opening.

Alternate Embodiment E2

The cartridge of Alternate Embodiment S1 wherein the analyte is glucose.

Alternate Embodiment F2

The cartridge of Alternate Embodiment S1 further including desiccant.

Alternate Embodiment G2

The cartridge of Alternate Embodiment S1 wherein the plurality of sensors is electrochemical sensors.

Alternate Embodiment H2

The cartridge of Alternate Embodiment S1 wherein the plurality of sensors is optical sensors.

Alternate Embodiment I2

A cartridge comprising:
a housing forming at least one opening therethrough;
a plurality of test sensors being stacked in the housing, the plurality of test sensors being adapted to assist in testing at least one analyte;
a first mechanical mechanism being adapted to urge the plurality of test sensors in a first direction, one of the plurality of test sensors being positioned for extraction from the cartridge;

a second mechanical mechanism being adapted to urge the plurality of test sensors in a second direction, the second direction being located generally perpendicular to the first direction;

a test-sensor extractor being moveable between a first position and a second position via the second mechanical mechanism; and a lid being moveable being a closed position and an open position such that the lid seals the opening in the closed position, wherein during the movement of the lid from the closed position to the open position, the test-sensor extractor moves from the first position to the second position and extracts one of the plurality of test sensors at least partially through the opening.

Alternate Embodiment J2

The cartridge of Alternate Embodiment I2 wherein the first mechanical mechanism is a spring and the second mechanical mechanism is a spring.

Alternate Embodiment K2

The cartridge of Alternate Embodiment I2 wherein the test-sensor extractor has a generally horizontal portion and an angular portion, the angular portion extending from the cartridge when the lid is in the open position.

Alternate Embodiment L2

The cartridge of Alternate Embodiment I2 wherein the test-sensor extractor has a generally horizontal portion and a second portion, the second portion extending from the cartridge when the lid is in the open position.

Alternate Embodiment M2

The cartridge of Alternate Embodiment I2 wherein the lid includes a first end and a second end, the lid being moveable between a closed position and an open position via a hinge located near the first end such that the lid seals the opening in the closed position, the lid including a projection located near the second end, the projection extending generally downwardly into an interior of the cartridge.

Alternate Embodiment N2

The cartridge of Alternate Embodiment M2 wherein the projection forms at least one detent to assist in locking the cartridge.

Alternate Embodiment O2

The cartridge of Alternate Embodiment I2 wherein the housing forms exactly one opening.

Alternate Embodiment P2

The cartridge of Alternate Embodiment I2 wherein the analyte is glucose.

Alternate Embodiment Q2

The cartridge of Alternate Embodiment I2 further including desiccant.

Alternate Embodiment R2

The cartridge of Alternate Embodiment I2 wherein the plurality of sensors is electrochemical sensors.

Alternate Embodiment S2

The cartridge of Alternate Embodiment I2 wherein the plurality of sensors is optical sensors.

Alternate Embodiment T2

A cartridge comprising:
a housing forming at least one opening therethrough;
a plurality of test sensors being stacked in the housing on a slant, the plurality of test sensors being adapted to assist in testing at least one analyte;
a first mechanical mechanism being adapted to urge the plurality of test sensors in a first direction, one of the plurality of test sensors being positioned for extraction from the cartridge;
a lid being moveable between a closed position and an open position such that the lid seals the opening in the closed position; and
a pusher assembly being connected to the lid, the pusher assembly being moveable between a first position and a second position,
wherein during the movement of the lid from the closed position to the open position, the pusher assembly moves from the first position to the second position and extracts one of the plurality of test sensors at least partially through the opening.

Alternate Embodiment U2

The cartridge of Alternate Embodiment T2 wherein the pusher assembly is connected to the lid via a cam mechanism.

Alternate Embodiment V2

The cartridge of Alternate Embodiment T2 wherein the lid is moveable between the first position to the second position via a hinge.

Alternate Embodiment W2

The cartridge of Alternate Embodiment T2 further including at least one track to assist in guiding the plurality of test sensors.

Alternate Embodiment X2

The cartridge of Alternate Embodiment T2 further including a second mechanical mechanism adapted to urge the plurality of test sensors in a second direction, the second direction being located generally perpendicular to the first direction.

Alternate Embodiment Y2

The cartridge of Alternate Embodiment T2 further including a stop member adapted to assist in preventing or inhibiting more than one of the plurality of test sensors from being extracted at a time.

Alternate Embodiment Z2

The cartridge of Alternate Embodiment T2 wherein the first mechanical mechanism is a spring.

Alternate Embodiment A3

The cartridge of Alternate Embodiment T2 wherein the housing forms exactly one opening.

Alternate Embodiment B3

The cartridge of Alternate Embodiment T2 wherein the analyte is glucose.

Alternate Embodiment C3

The cartridge of Alternate Embodiment T2 further including desiccant.

Alternate Embodiment D3

The cartridge of Alternate Embodiment T2 wherein the plurality of sensors is electrochemical sensors.

Alternate Embodiment E3

The cartridge of Alternate Embodiment T2 wherein the plurality of sensors is optical sensors.

Alternate Embodiment F3

The cartridge of Alternate Embodiment T2 further including a sealing port, the sealing port surrounding the at least one opening.

Alternate Embodiment G3

A cartridge comprising:
a housing forming at least one opening therethrough;
a plurality of test sensors being stacked in the housing on a slant, the plurality of test sensors being adapted to assist in testing at least one analyte;
a mechanical mechanism being adapted to urge the plurality of test sensors in a first direction, one of the plurality of test sensors being positioned for extraction from the cartridge; and
a lid being moveable between a closed position and an open position, the lid sealing the opening in the closed position,
wherein the lid in the open position allows the plurality of test sensors, one at a time, to be manually extracted from the cartridge.

Alternate Embodiment H3

The cartridge of Alternate Embodiment G3 wherein the mechanical mechanism is a spring.

Alternate Embodiment I3

The cartridge of Alternate Embodiment G3 wherein the housing forms exactly one opening.

Alternate Embodiment J3

The cartridge of Alternate Embodiment G3 wherein the analyte is glucose.

Alternate Embodiment K3

The cartridge of Alternate Embodiment G3 further including desiccant.

Alternate Embodiment L3

The cartridge of Alternate Embodiment G3 wherein the plurality of sensors is electrochemical sensors.

Alternate Embodiment M3

The cartridge of Alternate Embodiment G3 wherein the plurality of sensors is optical sensors.

Alternate Embodiment N3

The cartridge of Alternate Embodiment G3 further including a sealing port, the sealing port surrounding the at least one opening.

Alternate Embodiment O3

A cartridge comprising:
a housing forming at least one opening therethrough;
a plurality of test sensors being stacked in the housing, the plurality of test sensors being adapted to assist in testing at least one analyte, the plurality of test sensors including at least one sensor electrical contact;
a mechanical mechanism adapted to urge the plurality of test sensors in a first direction, one of the plurality of test sensors being positioned for extraction from the cartridge; and
a lid being moveable between a closed position and an open position such that the lid seals the opening in the closed position, the lid including at least one lid electrical contact,
wherein during the movement of the lid from the closed position to the open position, the at least one electrical contact contacts the at least one sensor contact of one of the plurality of test sensors,
wherein during movement of the lid from the open position to the closed position, the lid extracts one of the plurality of test sensors at least partially through the opening.

Alternate Embodiment P3

The cartridge of Alternate Embodiment O3 wherein the lid includes a plurality of electrical contacts and each of the plurality of test sensors includes a plurality of sensor contacts.

Alternate Embodiment Q3

The cartridge of Alternate Embodiment O3 further comprising a plurality of retainer tabs to assist in sealing the cartridge.

Alternate Embodiment R3

The cartridge of Alternate Embodiment O3 further including desiccant.

Alternate Embodiment S3

The cartridge of Alternate Embodiment O3 wherein the mechanical mechanism is a spring.

Alternate Embodiment T3

The cartridge of Alternate Embodiment O3 wherein the housing forms exactly one opening.

Alternate Embodiment U3

The cartridge of Alternate Embodiment O3 wherein the analyte is glucose.

Alternate Embodiment V3

A cartridge comprising:
a housing having an interior portion;
a plurality of test sensors being stacked in the housing, the plurality of test sensors being adapted to assist in testing at least one analyte;
a mechanical mechanism being adapted to urge the plurality of test sensors in a first direction, one of the plurality of test sensors being positioned for extraction from the cartridge; and
a rotatable drum including at least one notch formed therein, the drum being coupled to an interior portion of the housing, the at least one notch being adapted to receive exactly one test sensor,
wherein during the movement of the drum from a first position to a second position, the plurality of test sensors, one at a time, is extracted from the interior of the cartridge.

Alternate Embodiment W3

The cartridge of Alternate Embodiment V3 further including an ejector mechanism adapted to at least partially remove one of the test sensors from the at least one notch in the drum.

Alternate Embodiment X3

The cartridge of Alternate Embodiment V3 wherein the drum is coupled to the interior portion of the housing by a push-fit attachment, the drum and a section of the interior portion of the housing being in a sealing engagement.

Alternate Embodiment Y3

The cartridge of Alternate Embodiment V3 wherein the drum is coupled to the interior portion of the housing by spring loading, the drum and a section of the interior portion of the housing being in a sealing engagement.

Alternate Embodiment Z3

The cartridge of Alternate Embodiment V3 further including a wheel connected to the drum, the wheel being adapted to assist in rotating the drum.

Alternate Embodiment A4

The cartridge of Alternate Embodiments Z3 wherein the wheel is a twist wheel.

Alternate Embodiment B4

The cartridge of Alternate Embodiment V3 wherein the mechanical mechanism is a spring.

Alternate Embodiment C4

The cartridge of Alternate Embodiment V3 wherein the analyte is glucose.

Alternate Embodiment D4

The cartridge of Alternate Embodiment V3 further including desiccant.

Alternate Embodiment E4

The cartridge of Alternate Embodiment V3 wherein the plurality of sensors is electrochemical sensors.

Alternate Embodiment F4

The cartridge of Alternate Embodiment V3 wherein the plurality of sensors is optical sensors.

Alternate Embodiment G4

A cartridge adapted to be used with a sensor-dispensing instrument, the cartridge comprising:
a housing forming at least two openings therethrough;
a plurality of test sensors being stacked in the housing, the plurality of test sensors being adapted to assist in testing at least one analyte;
a mechanical mechanism being adapted to urge the plurality of test sensors in a first direction; and
a test-sensor extractor being adapted to carry and extract the plurality of test sensors, one at a time, in a second direction at least partially through one of the at least two openings, the test-sensor extractor having a first portion and a second portion, the first portion and the second portion being connected by at least one hinge, the second direction and the first direction being generally perpendicular to each other.

Alternate Embodiment H4

The cartridge of Alternate Embodiment G4 further including at least two seals, the at least two seals covering the at least two openings in a closed position.

Alternate Embodiment I4

The cartridge of Alternate Embodiment G4 wherein the first and second portions are connected by at least two hinges.

Alternate Embodiment J4

The cartridge of Alternate Embodiment G4 wherein the mechanical mechanism is a spring.

Alternate Embodiment K4

The cartridge of Alternate Embodiment G4 wherein the analyte is glucose.

Alternate Embodiment L4

The cartridge of Alternate Embodiment G4 further including desiccant.

Alternate Embodiment M4

The cartridge of Alternate Embodiment G4 wherein the plurality of sensors is electrochemical sensors.

Alternate Embodiment N4

The cartridge of Alternate Embodiment G4 wherein the plurality of sensors is optical sensors.

Alternate Embodiment O4

A sensor-dispensing instrument comprising:
a cartridge including a cartridge housing, a plurality of test sensors, a mechanical mechanism and a test-sensor extractor, the cartridge housing forming at least two openings therethrough, the plurality of test sensors being stacked in the housing, the plurality of test sensors being adapted to assist in testing at least one analyte, the mechanical mechanism being adapted to urge the plurality of test sensors in a first direction, the test-sensor extractor being adapted to carry and extract the plurality of test sensors, one at a time, in a second direction at least partially through one of the openings, the test-sensor extractor having a first portion and a second portion, the first portion and the second portion being connected by at least one hinge, the second direction and the first direction being generally perpendicular to each other;
an instrument housing forming a dispensing outlet and being adapted to receive the cartridge;
an ejector mechanism being adapted to extend through at least one of the openings and contact the test-sensor extractor; and
at least one deflector being adapted to contact and deflect the first portion of the test-sensor extractor and assist in extracting the plurality of test sensors, one at a time, at least partially through the dispensing outlet.

Alternate Embodiment P4

The sensor-dispensing instrument of Alternate Embodiment O4 wherein the at least one deflector is exactly two deflectors.

Alternate Embodiment Q4

The sensor-dispensing instrument of Alternate Embodiment P4 wherein the test sensor is adapted to be extracted between the two deflectors.

Alternate Embodiment R4

The sensor-dispensing instrument of Alternate Embodiment O4 wherein the ejector mechanism is spring loaded.

Alternate Embodiment S4

The sensor-dispensing instrument of Alternate Embodiment O4 wherein the mechanical mechanism is a spring.

Alternate Embodiment T4

The sensor-dispensing instrument of Alternate Embodiment O4 wherein the analyte is glucose.

Alternate Embodiment U4

The sensor-dispensing instrument of Alternate Embodiment O4 further including desiccant.

Alternate Embodiment V4

The sensor-dispensing instrument of Alternate Embodiment O4 wherein the plurality of sensors is electrochemical sensors.

Alternate Embodiment W4

The sensor-dispensing instrument of Alternate Embodiment O4 wherein the plurality of sensors is optical sensors.

Alternate Embodiment X4

A cartridge adapted to be used with a sensor-dispensing instrument, the cartridge comprising:
a housing forming at least one opening therethrough;
a base being adapted to be in sealing engagement with the housing in a first position;
a plurality of test sensors being stacked in the housing, the plurality of test sensors being adapted to assist in testing at least one analyte; and
an exterior spring mechanism being attached to the housing and the base and adapted to assist in sealingly engaging the housing and the base,
wherein the housing and the base are in sealing engagement in a first position and wherein the housing and base are spaced apart in a second position.

Alternate Embodiment Y4

The cartridge of Alternate Embodiment X4 wherein at least one end of the housing is chamfered.

Alternate Embodiment Z4

The cartridge of Alternate Embodiment X4 wherein the exterior spring mechanism includes at least two springs.

Alternate Embodiment A5

The cartridge of Alternate Embodiment Z4 wherein the exterior spring mechanism includes at least four springs.

Alternate Embodiment B5

The cartridge of Alternate Embodiment X4 further including an interior mechanical mechanism adapted to urge the plurality of test sensors in a first direction.

Alternate Embodiment C5

The cartridge of Alternate Embodiment B5 wherein the interior mechanical mechanism is a spring.

Alternate Embodiment D5

The cartridge of Alternate Embodiment X4 wherein the housing forms exactly one opening.

Alternate Embodiment E5

The cartridge of Alternate Embodiment X4 wherein the analyte is glucose.

Alternate Embodiment F5

The cartridge of Alternate Embodiment X4 further including desiccant.

Alternate Embodiment G5

The cartridge of Alternate Embodiment X4 wherein the plurality of sensors is electrochemical sensors.

Alternate Embodiment H5

The cartridge of Alternate Embodiment X4 wherein the plurality of sensors is optical sensors.

Alternate Embodiment I5

A sensor-dispensing instrument comprising:
a cartridge including a cartridge housing, a base, a plurality of test sensors, and an exterior spring mechanism, the cartridge housing forming at least one opening therethrough, the base being adapted to be in sealing engagement with the housing in a first position, the plurality of test sensors being stacked in the housing, the plurality of test sensors being adapted to assist in testing at least one analyte, the exterior spring mechanism being attached to the cartridge housing and the base and adapted to assist in sealingly engaging the cartridge housing and the base;
an instrument housing forming a dispensing outlet and being adapted to received the cartridge; and
an ejector mechanism being adapted to move and be inserted between the cartridge housing and the base such that the cartridge housing and base are spaced apart, the ejector mechanism being adapted to carry and extract the plurality of test sensors, one at a time, in a second direction at least partially from the cartridge, the second direction being generally perpendicular to the first direction,
wherein the cartridge housing and the base are in sealing engagement in a first position and wherein the cartridge housing and base are spaced apart in a second position.

Alternate Embodiment J5

The sensor-dispensing instrument of Alternate Embodiment I5 wherein the ejector mechanism is chamfered.

Alternate Embodiment K5

The sensor-dispensing instrument of Alternate Embodiment J5 wherein at least one end of the cartridge housing is chamfered.

Alternate Embodiment L5

The sensor-dispensing instrument of Alternate Embodiment I5 wherein the exterior spring mechanism includes at least two springs.

Alternate Embodiment M5

The sensor-dispensing instrument of Alternate Embodiment L5 wherein the exterior spring mechanism includes at least four springs.

Alternate Embodiment N5

The sensor-dispensing instrument of Alternate Embodiment I5 further including an interior mechanical mechanism adapted to urge the plurality of test sensors in a first direction.

Alternate Embodiment O5

The sensor-dispensing instrument of Alternate Embodiment N5 wherein the interior mechanical mechanism is a spring.

Alternate Embodiment P5

The sensor-dispensing instrument of Alternate Embodiment I5 wherein the cartridge housing forms exactly one opening.

Alternate Embodiment Q5

The sensor-dispensing instrument of Alternate Embodiment T5 wherein the analyte is glucose.

Alternate Embodiment R5

The sensor-dispensing instrument of Alternate Embodiment I5 further including desiccant.

Alternate Embodiment S5

The sensor-dispensing instrument of Alternate Embodiment I5 wherein the plurality of sensors is electrochemical sensors.

Alternate Embodiment T5

The sensor-dispensing instrument of Alternate Embodiment I5 wherein the plurality of sensors is optical sensors.

Alternate Embodiment U5

A cartridge comprising:
a housing forming at least one opening therethrough;
a plurality of test sensors being stacked in the housing, the plurality of test sensors being adapted to assist in testing at least one analyte;
a mechanical mechanism being adapted to urge the plurality of test sensors in a first direction, one of the plurality of test sensors being positioned for extraction from the cartridge; and
a sliding pusher lid assembly including a flexible pusher tab, the flexible pusher tab being adapted to contact and push one of the plurality of test sensors from the housing and at least partially through the opening, the flexible pusher tab extending generally outwardly and generally downwardly from the remainder of the sliding pusher lid assembly,
wherein in the closed position, the sliding pusher lid assembly is adapted to assist in sealing the cartridge.

Alternate Embodiment V5

The cartridge of Alternate Embodiment U5 wherein the sliding pusher assembly further includes a pusher grip to assist in the user in gripping and sliding the pusher lid assembly.

Alternate Embodiment W5

The cartridge of Alternate Embodiment U5 further including a reference surface that is adapted to contact the plurality of test sensors one at a time and assist in removing the plurality of test sensors one at a time.

Alternate Embodiment X5

The cartridge of Alternate Embodiment U5 wherein the flexible pusher tab comprises polycarbonate, ABS, nylon, polyethylene, polystyrene, polypropylene, or combinations thereof.

Alternate Embodiment Y5

The cartridge of Alternate Embodiment U5 wherein each of the plurality of test sensors forms a second notch, the flexible pusher tab forming a first notch at one end thereof to assist in engages the second notch and removing the plurality of test sensors one at a time.

Alternate Embodiment Z5

The cartridge of Alternate Embodiment U5 further including a guiding mechanism to assist in positioning the flexible pusher tab and facilitating removing the plurality of test sensors one at a time.

Alternate Embodiment A6

The cartridge of Alternate Embodiment Z5 wherein the guiding mechanism is a cam mechanism.

Alternate Embodiment B6

The cartridge of Alternate Embodiment U5 wherein the sliding pusher lid assembly during the pushing of one of the plurality of test sensors is adapted to engage a bottom surface of one of the test sensors such that the one of the plurality of the test sensors does not touch any of the remaining test sensors.

Alternate Embodiment C6

The cartridge of Alternate Embodiment U5 wherein the slider pusher lid assembly further includes a détente to assist in indicating to the user that the slider pusher lid assembly is in a closed position.

Alternate Embodiment D6

The cartridge of Alternate Embodiment U5 wherein the mechanical mechanism is a spring.

Alternate Embodiment E6

The cartridge of Alternate Embodiment U5 wherein the housing forms exactly one opening.

Alternate Embodiment F6

The cartridge of Alternate Embodiment U5 wherein the analyte is glucose.

Alternate Embodiment G6

The cartridge of Alternate Embodiment U5 wherein the plurality of sensors is electrochemical sensors.

Alternate Embodiment H6

The cartridge of Alternate Embodiment U5 wherein the plurality of sensors is optical sensors.

Alternate Embodiment I6

The cartridge of Alternate Embodiment U5 wherein the flexible pusher tab is adapted to clear the seal when the sliding pusher lid assembly is moved to an open position.

Alternate Embodiment J6

The cartridge of Alternate Embodiment U5 wherein the flexible pusher tab is attached to the sliding pusher lid assembly via a flexible support.

Alternate Embodiment K6

The cartridge of Alternate Embodiment U5 wherein the flexible support comprises metal or polymeric material.

Alternate Embodiment L6

The cartridge of Alternate Embodiment U5 wherein the sliding pusher lid assembly includes a latching mechanism and a flexible tab to unlock and disengage the sliding pusher lid assembly.

Alternate Embodiment M6

A sensor-dispensing instrument adapted to determine a concentration of an analyte, the sensor-dispensing instrument comprising:
a cartridge including a cartridge housing, a plurality of test sensors, and a mechanical mechanism, and a sliding pusher lid assembly, the cartridge housing forming at least one cartridge opening therethrough, the plurality of test sensors being stacked in the cartridge housing, the plurality of test sensors being adapted to assist in testing at least one analyte, the mechanical mechanism being adapted to urge the plurality of test sensors in a first direction, one of the plurality of test sensors being positioned for extraction from the cartridge, the sliding pusher lid assembly being moveable between a first position and a second position, the sliding pusher lid assembly being adapted to assist in sealing the sensor-dispensing instrument in the second position, the sliding pusher assembly including a flexible pusher tab, the flexible pusher tab extending generally outwardly and generally downwardly from the remainder of the sliding pusher lid assembly; and
an instrument housing forming a dispensing outlet and adapted to receive the cartridge,
wherein the flexible pusher tab is adapted to push one of the plurality of test sensors from the cartridge and at least partially through the dispensing outlet.

Alternate Embodiment N6

The sensor-dispensing instrument of Alternate Embodiment M6 wherein the instrument housing further forms a cavity, the cavity being adapted to at least partially receive the sliding pusher lid assembly when the sliding pusher assembly is in a first position.

Alternate Embodiment O6

The sensor-dispensing instrument of Alternate Embodiment M6 wherein the sliding pusher lid assembly in the second position is adapted to assist in sealing the cartridge opening and the dispensing outlet.

Alternate Embodiment P6

The sensor-dispensing instrument of Alternate Embodiment M6 wherein the sliding pusher lid assembly further includes a pusher grip to assist in the user in gripping and sliding the sliding pusher assembly.

Alternate Embodiment Q6

The sensor-dispensing instrument of Alternate Embodiment M6 wherein the cartridge further includes a reference surface that is adapted to contact the plurality of test sensors one at a time and assist in removing the plurality of test sensors one at a time.

Alternate Embodiment R6

The sensor-dispensing instrument of Alternate Embodiment M6 wherein the flexible pusher tab comprises polycarbonate, ABS, nylon, polyethylene, polystyrene, polypropylene, or combinations thereof.

Alternate Embodiment S6

The sensor-dispensing instrument of Alternate Embodiment M6 wherein each of the plurality of test sensors forms a second notch, the flexible pusher tab forming a first notch at one end thereof to assist in engages the second notch and removing the plurality of test sensors one at a time.

Alternate Embodiment T6

The sensor-dispensing instrument of Alternate Embodiment M6 wherein the cartridge further including a guiding mechanism to assist in positioning the flexible pusher tab and facilitating removing the plurality of test sensors one at a time.

Alternate Embodiment U6

The sensor-dispensing instrument of Alternate Embodiment T6 wherein the guiding mechanism is a cam mechanism.

Alternate Embodiment V6

The sensor-dispensing instrument of Alternate Embodiment M6 wherein the sliding pusher lid assembly during the pushing of one of the plurality of test sensors is adapted to engage a bottom surface of one of the test sensors such that the one of the plurality of the test sensors does not touch any of the remaining test sensors.

Alternate Embodiment W6

The sensor-dispensing instrument of Alternate Embodiment M6 wherein the slider pusher lid assembly further includes a détente to assist in indicating to the user that the slider pusher lid assembly is in a closed position.

Alternate Embodiment X6

The sensor-dispensing instrument of Alternate Embodiment M6 wherein the mechanical mechanism is a spring.

Alternate Embodiment Y6

The sensor-dispensing instrument of Alternate Embodiment M6 wherein the analyte is glucose.

Alternate Embodiment Z6

The sensor-dispensing instrument of Alternate Embodiment M6 wherein the plurality of sensors is electrochemical sensors.

Alternate Embodiment A7

The sensor-dispensing instrument of Alternate Embodiment M6 wherein the plurality of sensors is optical sensors.

Alternate Embodiment B7

The sensor-dispensing instrument of Alternate Embodiment M6 wherein the flexible pusher tab is adapted to clear the seal when the sliding pusher lid assembly is moved to an open position.

Alternate Embodiment C7

The sensor-dispensing instrument of Alternate Embodiment M6 wherein the flexible pusher tab is attached to the sliding pusher lid assembly via a flexible support.

Alternate Embodiment D7

The sensor-dispensing instrument of Alternate Embodiment C7 wherein the flexible support comprises metal or polymeric material.

Alternate Embodiment E7

The sensor-dispensing instrument of Alternate Embodiment M6 wherein the sliding pusher lid assembly includes a latching mechanism and a flexible tab to unlock and disengage the sliding pusher lid assembly.

While the invention is susceptible to various modifications and alternative forms, specific embodiments are shown by way of example in the drawings and are described in detail herein. It should be understood, however, that the invention is not intended to be limited to the particular forms disclosed. For example, the sensor-dispensing instrument can be used for testing fluids other than blood glucose. In fact, the sensor-dispensing instrument can be used in connection with the analysis of any type of chemistry fluid that can be analyzed by means of a reagent material. Rather, the invention is to cover all modifications, equivalents, and alternatives falling within the spirit and scope of the invention as defined by the appended claims.

The invention claimed is:

1. A sensor-dispensing instrument comprising:
a cartridge including a cartridge housing, a plurality of test sensors, a mechanical mechanism and a pusher assembly, the cartridge housing forming at least one cartridge opening therethrough, the plurality of test sensors being stacked in the cartridge housing, the plurality of test sensors being adapted to assist in testing at least one analyte, the mechanical mechanism being adapted to urge the plurality of test sensors in a first direction, one of the plurality of test sensors being positioned for extraction from the cartridge, the pusher assembly being adapted to push one of the plurality of test sensors from the cartridge, the pusher assembly including a ferromagnetic material or a magnet;
an instrument housing forming a dispensing outlet and being adapted to receive the cartridge;
a lid being moveable between a closed position and an open position such that the lid seals at least one of the dispensing outlet and the cartridge opening in the closed position; and
a slider comprising a ferromagnetic material or a magnet, the slider being adapted to be magnetically coupled to the pusher assembly of the cartridge, the slider being adapted to slide from a first position to a second position, wherein during the movement of the slider from the first position to the second position, the pusher assembly contacts one of the plurality of test sensors and pushes it at least partially through the dispensing opening, wherein at least one of the pusher assembly or the slider comprises a magnet.

2. The sensor-dispensing instrument of claim 1, wherein the plurality of sensors is electrochemical sensors.

3. The sensor-dispensing instrument of claim 1, wherein the plurality of sensors is optical sensors.

4. The sensor-dispensing instrument of claim 1, wherein the pusher assembly and the slider include a magnet.

5. The sensor-dispensing instrument of claim 1, wherein the pusher assembly comprises a ferromagnetic material and the slider comprises a magnet.

6. The sensor-dispensing instrument of claim 1, wherein the pusher assembly comprises a magnet and the slider comprises a ferromagnetic material.

7. The sensor-dispensing instrument of claim 1, wherein the lid is moved between an open position and a closed position via a hinge.

8. The sensor-dispensing instrument of claim 7, wherein during the movement of the slider from the first position to the second position, the slider contacts the lid and moves the lid from a closed position to an open position.

9. The sensor-dispensing instrument of claim 1, wherein the lid is adapted to slide between an open position and a closed position.

10. The sensor-dispensing instrument of claim 9, wherein the lid is adapted to manually slide between the open position and the closed position.

11. The sensor-dispensing instrument of claim 9, wherein the lid is adapted to automatically slide between the open position and the closed position.

12. The sensor-dispensing instrument of claim 1, further comprising a seal located generally around the periphery of the dispensing opening.

13. The sensor-dispensing instrument of claim 1, wherein the lid includes a first end and a second end, the lid being moveable between a closed position and an open position via a hinge located near the first end such that the lid seals the opening in the closed position, the lid including a projection located near the second end, the projection extending generally downwardly into an interior of the cartridge.

14. The sensor-dispensing instrument of claim 13, wherein the projection forms at least one detent to assist in further sealing the cartridge.

15. The sensor-dispensing instrument of claim 1, wherein the lid seals the dispensing outlet in the closed position.

16. The sensor-dispensing instrument of claim 1, wherein the lid seals the cartridge opening in the closed position.

* * * * *